(12) United States Patent
Westbrook et al.

(10) Patent No.: US 7,897,361 B2
(45) Date of Patent: Mar. 1, 2011

(54) METHODS OF DIAGNOSING ALZHEIMER'S DISEASE

(76) Inventors: Jules Westbrook, Dublin (IE); Helen Byers, Cobham Surrey (GB); Malcolm Ward, Cobham Surrey (GB); Simon Lovestone, London (GB); Abdul Hye, London (GB); Stephen Lynham, London (GB); Richard Joubert, Niedernhausen (DE); Petra Prefot, Wiesbaden (DE); Karsten Kuhn, Hofheim (DE); Christian Baumann, Offenbad (DE); Juergen Schaefer, Lauterbach (DE); Thorsten Prinz, Hofheim (DE); Stefan Kienle, Frankfurt (DE)

( * ) Notice: Subject to any disclaimer, the term of this patent is extended or adjusted under 35 U.S.C. 154(b) by 0 days.

(21) Appl. No.: 11/664,076

(22) PCT Filed: Sep. 29, 2005

(86) PCT No.: PCT/GB2005/003756
§ 371 (c)(1),
(2), (4) Date: Oct. 16, 2007

(87) PCT Pub. No.: WO2006/035237
PCT Pub. Date: Apr. 6, 2006

(65) Prior Publication Data
US 2008/0070995 A1    Mar. 20, 2008

(30) Foreign Application Priority Data
Sep. 29, 2004   (GB) .................................. 0421639.6

(51) Int. Cl.
*C12Q 1/68* (2006.01)
*G01N 33/53* (2006.01)
*G01N 33/566* (2006.01)
*G01N 33/567* (2006.01)

(52) U.S. Cl. .......... 435/7.92; 435/7.1; 435/7.9; 436/501; 436/503

(58) Field of Classification Search .................. None
See application file for complete search history.

(56) References Cited

U.S. PATENT DOCUMENTS

2002/0174447 A1   11/2002   Greenspan et al.
2003/0131364 A1    7/2003   Duff
2003/0211622 A1   11/2003   Roberts

OTHER PUBLICATIONS

Schenk et al. J. Mol. Chem., 1995, vol. 38, No. 21, pp. 4141-4154.*
Tilleman, Kelly et al., "Differential expression of brain proteins in glycogen synthase kinase-3beta transgenic mice: A proteomics point of view", Proteomics, 2(1): 94-104 (2002).
Andreasen, Niels et al., "Cerebrospinal fluid beta-amyloid(1-42) in Alzheimer disease: Differences between early- and late-onset Alzheimer disease and stability during the course of disease", Archives of Neurology, 56(6): 673-680 (1999).
Kanai et al., "Longitudinal Study of Cerebrospinal Fluid Levels of Tau, ABeta1-40, and ABeta1-42(43) in Alzheimer's Disease: A Study in Japan", Annals of Neurology, 44(1): 17-26 (1998).

* cited by examiner

*Primary Examiner* — Olga N Chernyshev
(74) *Attorney, Agent, or Firm* — Dann, Dorfman, Herrell and Skillman, P.C.; Patrick J. Hagan

(57) ABSTRACT

Methods and compositions relating to Alzheimer's disease are provided. Specifically, proteins that are differentially expressed in the Alzheimer's disease state relative to their expression in the normal state are provided. Proteins associated with Alzheimer's disease are identified and described. Methods of diagnosis of Alzheimer's disease using the differentially expressed proteins are also provided, as are methods for the identification and therapeutic use of compounds for the prevention and treatment of Alzheimer's disease.

8 Claims, 20 Drawing Sheets

| Spot No. | Rank | p Value | Fold Difference | State Change | Protein I.D. | Accession No. | Search Log No. |
|---|---|---|---|---|---|---|---|
| 196 | 1 | 0.00030199 | 1.78 | ↑ AD | Desmoplakin (DP) (250/210 kDa paraneoplastic pemphingus antigen) | P15924 | 7495 |
| | | | | | Ig kappa chain C region | P01834 | 7542 |
| | | | | | Ig kappa chain V-II region TEW | P01617 | 7542 |
| | | | | | Serum amyloid P-component precursor (SAP) (9.5S alpha-1-glycoprotein) | P02743 | 7951 |
| 171 | 2 | 0.001255545 | 2.11 | ↑ AD | Ig kappa chain C region | P01834 | 5623 |
| | | | | | Serum albumin precursor | P02768 | 7954 |
| | | | | | Galectin-7 (Gal-7) (HKL-14) (PI7) (p53-induced protein 1) | P47929 | 5623 |
| 2 (old) | 3 | 0.001447694 | 13.75 | ↑ AD | Complement factor H precursor (H factor 1) | P08603 | 6672 |
| | | | | | Serum albumin precursor | P02768 | 6672 |
| | | | | | Alpha-2-macroglobulin precursor (Alpha-2-M) | P01023 | 6672 |
| | | | | | Ceruloplasmin precursor (EC 1.16.3.1) (Ferroxidase) | P00450 | 6672 |
| 184 | 4 | 0.005360087 | 2.43 | ↑ AD | Ig lambda chain C regions | P01842 | 7818 |
| | | | | | Ig lambda chain V-III region LOI | P80748 | 7818 |
| | | | | | Serum albumin precursor | P02768 | 7818 |
| | | | | | Complement factor H-related protein 2 precursor (FHR-2) | P36980 | 7818 |
| 177 (old) | 5 | 0.005382883 | 1.92 | ↑ AD | Ig lambda chain C regions | P01842 | 5627 |
| | | | | | Serum albumin precursor | P02768 | 7955 |
| | | | | | Ig lambda chain V-III region LOI | P80748 | 7955 |
| | | | | | Ig kappa chain C region | P01834 | 7955 |
| 4 | 6 | 0.005985336 | 8.83 | ↑ AD | Alpha-2-macroglobulin precursor (Alpha-2-M) | P01023 | 7827 |
| 170 | 7 | 0.01167553 | 1.98 | ↑ AD | | | |
| 13 | 8 | 0.015500401 | 4.23 | ↓ AD | Inter-alpha-trypsin inhibitor heavy chain H4 precursor (ITI heavy chain H4) | Q14624 | 7829 |
| | | | | | Ceruloplasmin precursor (EC 1.16.3.1) (Ferroxidase) | P00450 | 7829 |
| 165 (old) | 9 | 0.018305158 | 1.58 | ↓ AD | Serum albumin precursor | P02768 | 5625 |
| 164 | 10 | 0.020647469 | 2.03 | ↓ AD | Complement C4 precursor [Contains: C4a anaphylatoxin; C4b] | P01028 | 7821 |

Figure 6

| | | | | | |
|---|---|---|---|---|---|
| | | | Ig gamma-1 chain C region | P01857 | 7821 |
| 14 (old) | 11 | 0.025004429 | 10.82 | ↓ AD | Serum albumin precursor | P02768 | 6227 |
| | | | | | Histone H2B.a/g/h/k/l (H2B.1 A) (H2B/a) (H2B/g) (H2B/h) (H2B/k) (H2B/l) | P62807 | 6227 |
| 126 | 12 | 0.028979402 | 1.6 | ↓ AD | CD5 antigen-like precursor (SP-alpha) (CT-2) (IgM-associated peptide) | O43866 | 7493 |
| | | | | | Serum albumin precursor | P02768 | 7952 |
| | | | | | Ig mu chain C region | P01871 | 7952 |
| 176 | 13 | 0.029106689 | 1.75 | ↑ AD | Ig lambda chain C regions | P01842 | 7816 |
| | | | | | Serum albumin precursor | P02768 | 7816 |
| | | | | | Ig lambda chain V-III region LOI | P80748 | 7816 |
| 123 | 14 | 0.031441346 | 1.36 | ↑ AD | Serum albumin precursor | P02768 | 7462 |
| 1 | 15 | 0.034723104 | 3.32 | ↑ AD | Alpha-2-macroglobulin precursor (Alpha-2-M) | P01023 | 7823 |
| | | | | | Ig alpha-1 chain C region | P01876 | 7823 |

Figure 6 (continued)

| Band No. | Protein I.D. | Species | Accession No. | Gel MW (Da) | MW (Da) | pI | No. Peptides Matched | Percentage Coverage | Error (ppm) | Search Log No. | Peptide Matched |
|---|---|---|---|---|---|---|---|---|---|---|---|
| SP1_1C | Haptoglobin precursor | Human | P00738 | 19300 | 45177 | 6.13 | 5 | 9% | 16 | 5288 | |
| SP1_2C | Transthyretin | Human | gi|339685 | 18200 | 12835 | 5.33 | 8 | 87% | 223 | 5275 | |
| | Serum albumin precursor | Human | P02768 | 18200 | 69248 | 5.82 | 3 | 6% | 236 | 5274 | |
| | Complement C4 precursor | Human | P01028 | 18200 | 192650 | 6.65 | 1 | 0% | 296 | 5274 | GLEELQFSLGSK |
| | Fibrinogen alpha/alpha-E chain precursor | Human | P02671 | 18200 | 94914 | 5.7 | 1 | 3% | 224 | 5274 | EWTSDSGCPEAMDLGTLSGIGTLDGFR |
| SP1_3C | Chain A, Transthyretin | Human | gi|443295 | 14900 | 13753 | 5.35 | 10 | 92% | 102 | 5251 | |
| | Apolipoprotein A-IV precursor (Apo-AIV) | Human | P06727 | 14900 | 45343 | 5.28 | 2 | 10% | 100 | 5247 | |
| | Serum albumin precursor | Human | P02768 | 14900 | 69321 | 5.92 | 1 | 1% | 109 | 5247 | |
| SP1_4C | Transthyretin precursor | Human | P02766 | 14200 | 15877 | 5.52 | 5 | 60% | 170 | 5260 | |
| | Hemoglobin beta chain | Human | P02023 | 14200 | 15857 | 6.81 | 4 | 28% | 12 | 5260 | |
| | Serum albumin precursor | Human | P02768 | 14200 | 69321 | 5.92 | 4 | 7% | 7 | 5260 | |
| SP1_5C | Haptoglobin-related protein precursor | Human | P00739 | 12600 | 38983 | 6.42 | 5 | 10% | 102 | 5294 | |
| | Transthyretin precursor | Human | P02766 | 12600 | 15877 | 5.52 | 2 | 16% | 129 | 5294 | |
| | Serum albumin precursor | Human | P02768 | 12600 | 69321 | 5.92 | 4 | 10% | 120 | 5294 | |
| | Apolipoprotein C-III precursor (Apo-CIII) | Human | P02656 | 12600 | 10845 | 5.23 | 1 | 16% | 122 | 5294 | DALSSVQESQVAQQAR |
| | Hemoglobin alpha | Human | P01922 | 12600 | 15227 | 9.84 | 2 | 17% | 118 | 5294 | |
| | Hemoglobin beta chain | Human | P02023 | 12600 | 15857 | 6.81 | 1 | 15% | 131 | 5294 | SAVTALWGKVNVDEVGGEALGR |
| SP1_6C | Serum albumin precursor | Human | P02768 | 11600 | 69321 | 5.92 | 6 | 11% | 244 | 5280 | |
| | Apolipoprotein C-III precursor (Apo-CIII) | Human | P02656 | 11600 | 10845 | 5.23 | 3 | 37% | 244 | 5280 | |
| | Haptoglobin precursor | Human | P00738 | 11600 | 45177 | 6.13 | 2 | 6% | 233 | 5280 | |
| | Vitronectin precursor (Serum spreading factor) (S-protein) | Human | P04004 | 11600 | 54271 | 5.55 | 1 | 3% | 249 | 5280 | SIAQYWLGCPAPGHL |

Figure 7

| No | IPI Accession no | SWISS-PROT Accession no | Name | No of matched peptides | regulation (control / disease) | CV (%) |
|---|---|---|---|---|---|---|
| 1 | IPI00166866 | P01876 | MGC27165 PROTEIN | 2 | 0,38 | 7 |
| 2 | IPI00336074 | P01876 | IG ALPHA-1 CHAIN C REGION | 2 | 0,35 | 4 |
| 3 | IPI00423461 | P01842 | HYPOTHETICAL PROTEIN DKFZP686C02220 (FRAGMENT) | 2 | 0,35 | 24 |
| 4 | IPI00431645 | P00738 | HAPTOGLOBIN PRECURSOR | 1 | 0,33 | - |
| 5 | IPI00478493 | P00738 | HAPTOGLOBIN PRECURSOR | 1 | 0,34 | - |

Figure 8

```
  1 MFLKAVVLTL ALVAVAGARA EVSADQVATV MWDYFSQLSN NAKEAVEHLQ
 51 KSELTQQLNA LFQDKLGEVN TYAGDLQKKL VPFATELHER LAKDSEKLKE
101 EIGKELEELR ARLLPHANEV SQKIGDNLRE LQQRLEPYAD QLRTQVNTQA
151 EQLRRQLTPY AQRMERVLRE NADSLQASLR PHADELKAKI DQNVEELKGR
201 LTPYADEFKV KIDQTVEELR RSLAPYAQDT QEKLNHQLEG LTFQMKKNAE
251 ELKARISASA EELRQRLAPL AEDVRGNLKG NTEGLQKSLA ELGGHLDQQV
301 EEFRRRVEPY GENFNKALVQ QMEQLRQKLG PHAGDVEGHL SFLEKDLRDK
351 VNSFFSTFKE KESQDKTLSL PELEQQQEQQ QEQQQEQVQM LAPLES
```

Figure 9

```
   1 MRLLWGLIWA SSFFTLSLQK PRLLLFSPSV VHLGVPLSVG VQLQDVPRGQ
  51 VVKGSVFLRN PSRNNVPCSP KVDFTLSSER DFALLSLQVP LKDAKSCGLH
 101 QLLRGPEVQL VAHSPWLKDS LSRTTNIQGI NLLFSSRRGH LFLQTDQPIY
 151 NPGQRVRYRV FALDQKMRPS TDTITVMVEN SHGLRVRKKE VYMPSSIFQD
 201 DFVIPDISEP GTWKISARFS DGLESNSSTQ FEVKKYVLPN FEVKITPGKP
 251 YILTVPGHLD EMQLDIQARY IYGKPVQGVA YVRFGLLDED GKKTFFRGLE
 301 SQTKLVNGQS HISLSKAEFQ DALEKLNMGI TDLQGLRLYV AAAIIESPGG
 351 EMEEAELTSW YFVSSPFSLD LSKTKRHLVP GAPFLLQALV REMSGSPASG
 401 IPVKVSATVS SPGSVPEVQD IQQNTDGSGQ VSIPIIIPQT ISELQLSVSA
 451 GSPHPAIARL TVAAPPSGGP GFLSIERPDS RPPRVGDTLN LNLRAVGSGA
 501 TFSHYYYMIL SRGQIVFMNR EPKRTLTSVS VFVDHHLAPS FYFVAFYYHG
 551 DHPVANSLRV DVQAGACEGK LELSVDGAKQ YRNGESVKLH LETDSLALVA
 601 LGALDTALYA AGSKSHKPLN MGKVFEAMNS YDLGCGPGGG DSALQVFQAA
 651 GLAFSDGDQW TLSRKRLSCP KEKTTRKKRN VNFQKAINEK LGQYASPTAK
 701 RCCQDGVTRL PMMRSCEQRA ARVQQPDCRE PFLSCCQFAE SLRKKSRDKG
 751 QAGLQRALEI LQEEDLIDED DIPVRSFFPE NWLWRVETVD RFQILTLWLP
 801 DSLTTWEIHG LSLSKTKGLC VATPVQLRVF REFHLHLRLP MSVRRFEQLE
 851 LRPVLYNYLD KNLTVSVHVS PVEGLCLAGG GGLAQQVLVP AGSARPVAFS
 901 VVPTAAAAVS LKVVARGSFE FPVGDAVSKV LQIEKEGAIH REELVYELNP
 951 LDHRGRTLEI PGNSDPNMIP DGDFNSYVRV TASDPLDTLG SEGALSPGGV
1001 ASLLRLPRGC GEQTMIYLAP TLAASRYLDK TEQWSTLPPE TKDHAVDLIQ
1051 KGYMRIQQFR KADGSYAAWL SRDSSTWLTA FVLKVLSLAQ EQVGGSPEKL
1101 QETSNWLLSQ QQADGSFQDP CPVLDRSMQG GLVGNDETVA LTAFVTIALH
1151 HGLAVFQDEG AEPLKQRVEA SISKANSFLG EKASAGLLGA HAAAITAYAL
1201 SLTKAPVDLL GVAHNNLMAM AQETGDNLYW GSVTGSQSNA VSPTPAPRNP
1251 SDPMPQAPAL WIETTAYALL HLLLHEGKAE MADQASAWLT RQGSFQGGFR
1301 STQDTVIALD ALSAYWIASH TTEERGLNVT LSSTGRNGFK SHALQLNNRQ
1351 IRGLEEELQF SLGSKINVKV GGNSKGTLKV LRTYNVLDMK NTTCQDLQIE
1401 VTVKGHVEYT MEANEDYEDY EYDELPAKDD PDAPLQPVTP LQLFEGRRNR
1451 RRREAPKVVE EQESRVHYTV CIWRNGKVGL SGMAIADVTL LSGFHALRAD
1501 LEKLTSLSDR YVSHFETEGP HVLLYFDSVP TSRECVGFEA VQEVPVGLVQ
1551 PASATLYDYY NPERRCSVFY GAPSKSRLLA TLCSAEVCQC AEGKCPRQRR
1601 ALERGLQDED GYRMKFACYY PRVEYGFQVK VLREDSRAAF RLFETKITQV
1651 LHFTKDVKAA ANQMRNFLVR ASCRLRLEPG KEYLIMGLDG ATYDLEGHPQ
1701 YLLDSNSWIE EMPSERLCRS TRQRAACAQL NDFLQEYGTQ GCQV
```

Figure 10

| Spot no. | Protein Name | Acc. No. | Norm. Vol Control | CV (%) | Norm. Vol Disease | CV (%) | Expression ratio | T-test (p) | Detection ratio | Theoretical Mr | pI | Cover-age (%) |
|---|---|---|---|---|---|---|---|---|---|---|---|---|
| 174 | alpha-2-macroglobulin precursor | P01023 | 0,36604 | 52 | 0,14510 | 57 | 0,40 | 2,50852E-06 | 28/21 | 160796 Da | 5,95 | 13,8 |
| 178 | alpha-2-macroglobulin precursor | P01023 | 0,29348 | 53 | 0,12475 | 57 | 0,43 | 1,25521E-05 | 27/20 | 160796 Da | 5,95 | 11,7 |
| 232 | Inter-alpha-trypsin inhibitor heavy chain H4 precursor | Q14624 | 0,32468 | 81 | 0,14481 | 64 | 0,45 | 0,001793752 | 28/27 | 103358 Da | 6,51 | 25,6 |
| 712 | Complement C3 precursor | P01024 | 0,81225 | 74 | 0,36446 | 62 | 0,45 | 0,001371446 | 28/24 | 184967 Da | 6,00 | 14,9 |
| 712 | Clusterin precursor | P10909 | 0,81225 | 74 | 0,36446 | 62 | 0,45 | 0,001371446 | 28/24 | 50062 Da | 5,89 | 22,9 |
| 713 | Complement C3 precursor | P01024 | 3,45803 | 67 | 1,44590 | 63 | 0,42 | 9,67927E-05 | 29/29 | 184967 Da | 6,00 | 16,9 |
| 652 | Complement C4 precursor | P01028 | 0,18067 | 122 | 0,39844 | 69 | 2,21 | 0,003595593 | 24/25 | 192771 Da | 6,60 | 5,9 |
| 675 | Actin cytoplasmic 2 (Gamma/beta actin) | P63261 | 0,21268 | 89 | 0,45443 | 74 | 2,14 | 0,002107165 | 25/28 | 41793 Da | 5,31 | 49,1 |
| 702 | Haptoglobin precursor | P00738 | 0,09210 | 86 | 0,40084 | 115 | 4,35 | 0,002920373 | 20/25 | 43349 Da | 6,13 | 21,2 |
| 703 | Haptoglobin precursor | P00738 | 1,54479 | 95 | 4,64500 | 76 | 3,01 | 0,000171685 | 24/28 | 43349 Da | 6,13 | 23,9 |
| 706 | Haptoglobin precursor | P00738 | 1,00814 | 112 | 3,26743 | 89 | 3,24 | 0,000607583 | 21/28 | 43349 Da | 6,13 | 23,6 |
| 832 | Complement C4 precursor | P01028 | 0,24743 | 126 | 0,61914 | 88 | 2,50 | 0,003005256 | 28/28 | 192771 Da | 6,60 | 4,5 |

Figure 12

```
   1 MGKNKLLHPS LVLLLLVLLP TDASVSGKPQ YMVLVPSLLH TETTEKGCVL LSYLNETVTV
  61 SASLESVRGN RSLFTDLEAE NDVLHCVAFA VPKSSSNEEV MFLTVQVKGP TQEFKKRTTV
 121 MVKNEDSLVF VQTDKSIYKP GQTVKFRVVS MDENFHPLNE LIPLVYIQDP KGNRIAQWQS
 181 FQLEGGLKQF SFPLSSEPFQ GSYKVVVQKK SGGRTEHPFT VEEFVLPKFE VQVTVPKIIT
 241 ILEEEMNVSV CGLYTYGKPV PGHVTVSICR KYSDASDCHG EDSQAFCEKF SGQLNSHGCF
 301 YQQVKTKVFQ LKRKEYEMKL HTEAQIQEEG TVVELTGRQS SEITRTITKL SFVKVDSHFR
 361 QGIPFFGQVR LVDGKGVPIP NKVIFIRGNE ANYYSNATTD EHGLVQFSIN TTNVMGTSLT
 421 VRVNYKDRSP CYGYQWVSEE HEEAHHTAYL VFSPSKSFVH LEPMSHELPC GHTQTVQAHY
 481 ILNGGTLLGL KKLSFYYLIM AKGGIVRTGT HGLLVKQEDM KGHFSISIPV KSDIAPVARL
 541 LIYAVLPTGD VIGDSAKYDV ENCLANKVDL SFSPSQSLPA SHAHLRVTAA PQSVCALRAV
 601 DQSVLLMKPD AELSASSVYN LLPEKDLTGF PGPLNDQDDE DCINRHNVYI NGITYTPVSS
 661 TNEKDMYSFL EDMGLKAFTN SKIRKPKMCP QLQQYEMHGP EGLRVGFYES DVMGRGHARL
 721 VHVEEPHTET VRKYFPETWI WDLVVVNSAG VAEVGVTVPD TITEWKAGAF CLSEDAGLGI
 781 SSTASLRAFQ PFFVELTMPY SVIRGEAFTL KATVLNYLPK CIRVSVQLEA SPAFLAVPVE
 841 KEQAPHCICA NGRQTVSWAV TPKSLGNVNF TVSAEALESQ ELCGTEVPSV PEHGRKDTVI
 901 KPLLVEPEGL EKETTFNSLL CPSGGEVSEE LSLKLPPNVV EESARASVSV LGDILGSAMQ
 961 NTQNLLQMPY GCGEQNMVLF APNIYVLDYL NETQQLTPEV KSKAIGYLNT GYQRQLNYKH
1021 YDGSYSTFGE RYGRNQGNTW LTAFVLKTFA QARAYIFIDE AHITQALIWL SQRQKDNGCF
1081 RSSGSLLNNA IKGGVEDEVT LSAYITIALL EIPLTVTHPV VRNALFCLES AWKTAQEGDH
1141 GSHVYTKALL AYAFALAGNQ DKRKEVLKSL NEEAVKKDNS VHWERPQKPK APVGHFYEPQ
1201 APSAEVEMTS YVLLAYLTAQ PAPTSEDLTS ATNIVKWITK QQNAQGGFSS TQDTVVALHA
1261 LSKYGAATFT RTGKAAQVTI QSSGTFSSKF QVDNNNRLLL QQVSLPELPG EYSMKVTGEG
1321 CVYLQTSLKY NILPEKEEFP FALGVQTLPQ TCDEPKAHTS FQISLSVSYT GSRSASNMAI
1381 VDVKMVSGFI PLKPTVKMLE RSNHVSRTEV SSNHVLIYLD KVSNQTLSLF FTVLQDVPVR
1441 DLKPAIVKVY DYYETDEFAI AEYNAPCSKD LGNA
```

Figure 13

```
  1  MKPPRPVRTC SKVLVLLSLL AIHQTTTAEK NGIDIYSLTV DSRVSSRFAH TVVTSRVVNR
 61  ANTVQEATFQ MELPKKAFIT NFSMNIDGMT YPGIIKEKAE AQAQYSAAVA KGKSAGLVKA
121  TGRNMEQFQV SVSVAPNAKI TFELVYEELL KRRLGVYELL LKVRPQQLVK HLQMDIHIFE
181  PQGISFLETE STFMTNQLVD ALTTWQNKTK AHIRFKPTLS QQQKSPEQQE TVLDGNLIIR
241  YDVDRAISGG SIQIENGYFV HYFAPEGLTT MPKNVVFVID KSGSMSGRKI QQTREALIKI
301  LDDLSPRDQF NLIVFSTEAT QWRPSLVPAS AENVNKARSF AAGIQALGGT NINDAMLMAV
361  QLLDSSNQEE RLPEGSVSLI ILLTDGDPTV GETNPRSIQN NVREAVSGRY SLFCLGFGFD
421  VSYAFLEKLA LDNGGLARRI HEDSDSALQL QDFYQEVANP LLTAVTFEYP SNAVEEVTQN
481  NFRLLFKGSE MVVAGKLQDR GPDVLTATVS GKLPTQNITF QTESSVAEQE AEFQSPKYIF
541  HNFMERLWAY LTIQQLLEQT VSASDADQQA LRNQALNLSL AYSFVTPLTS MVVTKPDDQE
601  QSQVAEKPME GESRNRNVHS GSTFFKYYLQ GAKIPKPEAS FSPRRGWNRQ AGAAGSRMNF
661  RPGVLSSRQL GLPGPPDVPD HAAYHPFRRL AILPASAPPA TSNPDPAVSR VMNMKIEETT
721  MTTQTPAPIQ APSAILPLPG QSVERLCVDP RHRQGPVNLL SDPEQGVEVT GQYEREKAGF
781  SWIEVTFKNP LVWVHASPEH VVVTRNRRSS AYKWKETLFS VMPGLKMTMD KTGLLLLSDP
841  DKVTIGLLFW DGRGEGLRLL LRDTDRFSSH VGGTLGQFYQ EVLWGSPAAS DDGRRTLRVQ
901  GNDHSATRER RLDYQEGPPG VEISCWSVEL
```

Figure 14

```
1     MGPTSGPSLL LLLLTHLPLA LGSPMYSIIT PNILRLESEE TMVLEAHDAQ GDVPVTVTVH
61    DFPGKKLVLS SEKTVLTPAT NHMGNVTFTI PANREFKSEK GRNKFVTVQA TFGTQVVEKV
121   VLVSLQSGYL FIQTDKTIYT PGSTVLYRIF TVNHKLLPVG RTVMVNIENP EGIPVKQDSL
181   SSQNQLGVLP LSWDIPELVN MGQWKIRAYY ENSPQQVFST EFEVKEYVLP SFEVIVEPTE
241   KFYYIYNEKG LEVTITARFL YGKKVEGTAF VIFGIQDGEQ RISLPESLKR IPIEDGSGEV
301   VLSRKVLLDG VQNLRAEDLV GKSLYVSATV ILHSGSDMVQ AERSGIPIVT SPYQIHFTKT
361   PKYFKPGMPF DLMVFVTNPD GSPAYRVPVA VQGEDTVQSL TQGDGVAKLS INTHPSQKPL
421   SITVRTKKQE LSEAEQATRT MQALPYSTVG NSNNYLHLSV LRTELRPGET LNVNFLLRMD
481   RAHEAKIRYY TYLIMNKGRL LKAGRQVREP GQDLVVLPLS ITTDFIPSFR LVAYYTLIGA
541   SGQREVVADS VWVDVKDSCV GSLVVKSGQS EDRQPVPGQQ MTLKIEGDHG ARVVLVAVDK
601   GVFVLNKKNK LTQSKIWDVV EKADIGCTPG SGKDYAGVFS DAGLTFTSSS GQQTAQRAEL
661   QCPQPAARRR RSVQLTEKRM DKVGKYPKEL RKCCEDGMRE NPMRFSCQRR TRFISLGEAC
721   KKVFLDCCNY ITELRRQHAR ASHLGLARSN LDEDIIAEEN IVSRSEFPES WLWNVEDLKE
781   PPKNGISTKL MNIFLKDSIT TWEILAVSMS DKKGICVADP FEVTVMQDFF IDLRLPYSVV
841   RNEQVEIRAV LYNYRQNQEL KVRVELLHNP AFCSLATTKR RHQQTVTIPP KSSLSVPYVI
901   VPLKTGLQEV EVKAAVYHHF ISDGVRKSLK VVPEGIRMNK TVAVRTLDPE RLGREGVQKE
961   DIPPADLSDQ VPDTESETRI LLQGTPVAQM TEDAVDAERL KHLIVTPSGC GEQNMIGMTP
1021  TVIAVHYLDE TEQWEKFGLE KRQGALELIK KGYTQQLAFR QPSSAFAAFV KRAPSTWLTA
1081  YVVKVFSLAV NLIAIDSQVL CGAVKWLILE KQKPDGVFQE DAPVIHQEMI GGLRNNNEKD
1141  MALTAFVLIS LQEAKDICEE QVNSLPGSIT KAGDFLEANY MNLQRSYTVA IAGYALAQMG
1201  RLKGPLLNKF LTTAKDKNRW EDPGKQLYNV EATSYALLAL LQLKDFDFVP PVVRWLNEQR
1261  YYGGGYGSTQ ATFMVFQALA QYQKDAPDHQ ELNLDVSLQL PSRSSKITHR IHWESASLLR
1321  SEETKENEGF TVTAEGKGQG TLSVVTMYHA KAKDQLTCNK FDLKVTIKPA PETEKRPQDA
1381  KNTMILEICT RYRGDQDATM SILDISMMTG FAPDTDDLKQ LANGVDRYIS KYELDKAFSD
1441  RNTLIIYLDK VSHSEDDCLA FKVHQYFNVE LIQPGAVKVY AYYNLEESCT RFYHPEKEDG
1501  KLNKLCRDEL CRCAEENCFI QKSDDKVTLE ERLDKACEPG VDYVYKTRLV KVQLSNDFDE
1561  YIMAIEQTIK SGSDEVQVGQ QRTFISPIKC REALKLEEKK HYLMWGLSSD FWGEKPNLSY
1621  IIGKDTWVEH WPEEDECQDE ENQKQCQDLG AFTESMVVFG CPN
```

Figure 15

```
1    MMKTLLLFVG  LLLTWESGQV  LGDQTVSDNE  LQEMSNQGSK  YVNKEIQNAV  NGVKQIKTLI
61   EKTNEERKTL  LSNLEEAKKK  KEDALNETRE  SETKLKELPG  VCNETMMALW  EECKPCLKQT
121  CMKFYARVCR  SGSGLVGRQL  EEFLNQSSPF  YFWMNGDRID  SLLENDRQQT  HMLDVMQDHF
181  SRASSIIDEL  FQDRFFTREP  QDTYHYLPFS  LPHRRPHFFF  PKSRIVRSLM  PFSPYEPLNF
241  HAMFQPFLEM  IHEAQQAMDI  HFHSPAFQHP  PTEFIREGDD  DRTVCREIRH  NSTGCLRMKD
301  QCDKCREILS  VDCSTNNPSQ  AKLRRELDES  LQVAERLTRK  YNELLKSYQW  KMLNTSSLLE
361  QLNEQFNWVS  RLANLTQGED  QYYLRVTTVA  SHTSDSDVPS  GVTEVVVKLF  DSDPITVTVP
421  VEVSRKNPKF  METVAEKALQ  EYRKKHREE
```

Figure 16

```
   1  MRLLWGLIWA SSFFTLSLQK PRLLLFSPSV VHLGVPLSVG VQLQDVPRGQ VVKGSVFLRN
  61  PSRNNVPCSP KVDFTLSSER DFALLSLQVP LKDAKSCGLH QLLRGPEVQL VAHSPWLKDS
 121  LSRTTNIQGI NLLFSSRRGH LFLQTDQPIY NPGQRVRYRV FALDQKMRPS TDTITVMVEN
 181  SHGLRVRKKE VYMPSSIFQD DFVIPDISEP GTWKISARFS DGLESNSSTQ FEVKKYVLPN
 241  FEVKITPGKP YILTVPGHLD EMQLDIQARY IYGKPVQGVA YVRFGLLDED GKKTFFRGLE
 301  SQTKLVNGQS HISLSKAEFQ DALEKLNMGI TDLQGLRLYV AAAIIESPGG EMEEAELTSW
 361  YFVSSPFSLD LSKTKRHLVP GAPFLLQALV REMSGSPASG IPVKVSATVS SPGSVPEVQD
 421  IQQNTDGSGQ VSIPIIIPQT ISELQLSVSA GSPHPAIARL TVAAPPSGGP GFLSIERPDS
 481  RPPRVGDTLN LNLRAVGSGA TFSHYYYMIL SRGQIVFMNR EPKRTLTSVS VFVDHHLAPS
 541  FYFVAFYYHG DHPVANSLRV DVQAGACEGK LELSVDGAKQ YRNGESVKLH LETDSLALVA
 601  LGALDTALYA AGSKSHKPLN MGKVFEAMNS YDLGCGPGGG DSALQVFQAA GLAFSDGDQW
 661  TLSRKRLSCP KEKTTRKKRN VNFQKAINEK LGQYASPTAK RCCQDGVTRL PMMRSCEQRA
 721  ARVQQPDCRE PFLSCCQFAE SLRKKSRDKG QAGLQRALEI LQEEDLIDED DIPVRSFFPE
 781  NWLWRVETVD RFQILTLWLP DSLTTWEIHG LSLSKTKGLC VATPVQLRVF REFHLHLRLP
 841  MSVRRFEQLE LRPVLYNYLD KNLTVSVHVS PVEGLCLAGG GGLAQQVLVP AGSARPVAFS
 901  VVPTAAAAVS LKVVARGSFE FPVGDAVSKV LQIEKEGAIH REELVYELNP LDHRGRTLEI
 961  PGNSDPNMIP DGDFNSYVRV TASDPLDTLG SEGALSPGGV ASLLRLPRGC GEQTMIYLAP
1021  TLAASRYLDK TEQWSTLPPE TKDHAVDLIQ KGYMRIQQFR KADGSYAAWL SRDSSTWLTA
1081  FVLKVLSLAQ EQVGGSPEKL QETSNWLLSQ QQADGSFQDP CPVLDRSMQG GLVGNDETVA
1141  LTAFVTIALH HGLAVFQDEG AEPLKQRVEA SISKANSFLG EKASAGLLGA HAAAITAYAL
1201  SLTKAPVDLL GVAHNNLMAM AQETGDNLYW GSVTGSQSNA VSPTPAPRNP SDPMPQAPAL
1261  WIETTAYALL HLLLHEGKAE MADQASAWLT RQGSFQGGFR STQDTVIALD ALSAYWIASH
1321  TTEERGLNVT LSSTGRNGFK SHALQLNNRQ IRGLEEELQF SLGSKINVKV GGNSKGTLKV
1381  LRTYNVLDMK NTTCQDLQIE VTVKGHVEYT MEANEDYEDY EYDELPAKDD PDAPLQPVTP
1441  LQLFEGRRNR RRREAPKVVE EQESRVHYTV CIWRNGKVGL SGMAIADVTL LSGFHALRAD
1501  LEKLTSLSDR YVSHFETEGP HVLLYFDSVP TSRECVGFEA VQEVPVGLVQ PASATLYDYY
1561  NPERRCSVFY GAPSKSRLLA TLCSAEVCQC AEGKCPRQRR ALERGLQDED GYRMKFACYY
1621  PRVEYGFQVK VLREDSRAAF RLFETKITQV LHFTKDVKAA ANQMRNFLVR ASCRLRLEPG
1681  KEYLIMGLDG ATYDLEGHPQ YLLDSNSWIE EMPSERLCRS TRQRAACAQL NDFLQEYGTQ
1741  GCQV
```

Figure 17

```
1    MEEEIAALVI DNGSGMCKAG FAGDDAPRAV FPSIVGRPRH QGVMVGMGQK DSYVGDEAQS
61   KRGILTLKYP IEHGIVTNWD DMEKIWHHTF YNELRVAPEE HPVLLTEAPL NPKANREKMT
121  QIMFETFNTP AMYVAIQAVL SLYASGRTTG IVMDSGDGVT HTVPIYEGYA LPHAILRLDL
181  AGRDLTDYLM KILTERGYSF TTTAEREIVR DIKEKLCYVA LDFEQEMATA ASSSSLEKSY
241  ELPDGQVITI GNERFRCPEA LFQPSFLGME SCGIHETTFN SIMKCDVDIR KDLYANTVLS
301  GGTTMYPGIA DRMQKEITAL APSTMKIKII APPERKYSVW IGGSILASLS TFQQMWISKQ
361  EYDESGPSIV HRKCF
```

Figure 18

```
1    MSALGAVIAL  LLWGQLFAVD  SGNDVTDIAD  DGCPKPPEIA  HGYVEHSVRY  QCKNYYKLRT
61   EGDGVYTLND  KKQWINKAVG  DKLPECEADD  GCPKPPEIAH  GYVEHSVRYQ  CKNYYKLRTE
121  GDGVYTLNNE  KQWINKAVGD  KLPECEAVCG  KPKNPANPVQ  RILGGHLDAK  GSFPWQAKMV
181  SHHNLTTGAT  LINEQWLLTT  AKNLFLNHSE  NATAKDIAPT  LTLYVGKKQL  VEIEKVVLHP
241  NYSQVDIGLI  KLKQKVSVNE  RVMPICLPSK  DYAEVGRVGY  VSGWGRNANF  KFTDHLKYVM
301  LPVADQDQCI  RHYEGSTVPE  KKTPKSPVGV  QPILNEHTFC  AGMSKYQEDT  CYGDAGSAFA
361  VHDLEEDTWY  ATGILSFDKS  CAVAEYGVYV  KVTSIQDWVQ  KTIAEN
```

Figure 19

METHODS OF DIAGNOSING ALZHEIMER'S DISEASE

FIELD OF THE INVENTION

The present invention relates to methods and compositions relating to Alzheimer's disease. Specifically, the present invention identifies and describes proteins that are differentially expressed in the Alzheimer's disease state relative to their expression in the normal state and, in particular, identifies and describes proteins associated with Alzheimer's disease. Further, the present invention provides methods of diagnosis of Alzheimer's disease using the differentially expressed proteins. Still further, the present invention provides methods for the identification and therapeutic use of compounds for the prevention and treatment of Alzheimer's disease.

BACKGROUND OF THE INVENTION

Dementia is one of the major public health problems of the elderly, and in our ageing populations the increasing numbers of patients with dementia is imposing a major financial burden on health systems around the world. More than half of the patients with dementia have Alzheimer's disease (AD). The prevalence and incidence of AD have been shown to increase exponentially. The prevalence for AD in Europe is 0.3% for ages 60-69 years, 3.2% for ages 70-79 years, and 10.8% for ages 80-89 years (Rocca, Hofman et al. 1991). The survival time after the onset of AD is approximately from 5 to 12 years (Friedland 1993).

Alzheimer's disease (AD), the most common cause of dementia in older individuals, is a debilitating neurodegenerative disease for which there is currently no cure. It destroys neurons in parts of the brain, chiefly the hippocampus, which is a region involved in coding memories. Alzheimer's disease gives rise to an irreversible progressive loss of cognitive functions and of functional autonomy. The earliest signs of AD may be mistaken for simple forgetfulness, but in those who are eventually diagnosed with the disease, these initial signs inexorably progress to more severe symptoms of mental deterioration. While the time it takes for AD to develop will vary from person to person, advanced signs include severe memory impairment, confusion, language disturbances, personality and behaviour changes, and impaired judgement. Persons with AD may become non-communicative and hostile. As the disease ends its course in profound dementia, patients are unable to care for themselves and often require institutionalisation or professional care in the home setting. While some patients may live for years after being diagnosed with AD, the average life expectancy after diagnosis is eight years.

In the past, AD could only be definitively diagnosed by brain biopsy or upon autopsy after a patient died. These methods, which demonstrate the presence of the characteristic plaque and tangle lesions in the brain, are still considered the gold standard for the pathological diagnoses of AD. However, in the clinical setting brain biopsy is rarely performed and diagnosis depends on a battery of neurological, psychometric and biochemical tests, including the measurement of biochemical markers such as the ApoE and tau proteins or the beta-amyloid peptide in cerebrospinal fluid and blood.

Biomarkers may possibly possess the key in the next step for diagnosing AD and other dementias. A biological marker that fulfils the requirements for the diagnostic test for AD would have several advantages. An ideal biological marker would be one that identifies AD cases at a very early stage of the disease, before there is degeneration observed in the brain imaging and neuropathological tests. A biomarker could be the first indicator for starting treatment as early as possible, and also very valuable in screening the effectiveness of new therapies, particularly those that are focussed on preventing the development of neuropathological changes. A biological marker would also be useful in the follow-up of the development of the disease.

Markers related to pathological characteristics of AD; plaques and tangles (Aβ and tau) have been the most extensively studied. The most promising has been from studies of CSF concentration of Aβ(1-40), Aβ(1-42) and tau or the combination of both proteins in AD. Many studies have reported a decrease in Aβ(1-42) in CSF, while the total Aβ protein or Aβ(1-40) concentration remain unchanged (Ida, Hartmann et al. 1996; Kanai, Matsubara et al. 1998; Andreasen, Hesse et al. 1999).

SUMMARY OF THE INVENTION

Broadly, the present invention relates to methods and compositions for the diagnosis of Alzheimer's disease. More specifically, the present invention identifies and describes proteins that are differentially expressed in the Alzheimer's disease state relative to their expression in the normal state.

In a first aspect, the invention provides a method of diagnosing Alzheimer's disease in a subject, the method comprising detecting one or more of a differentially expressed protein identified by the methods described herein in a tissue sample or body fluid sample from said subject. Preferably, the method is an in vitro method.

In all aspects, the methods of the present invention may also be used in relation to pre-Alzheimer's stages such as mild cognitive impairment (MCI) as well as advanced Alzheimer's disease.

In another aspect, the present invention provides a method of determining the nature or degree of Alzheimer's disease in a human or animal subject, the method comprising detecting one or more of a differentially expressed protein identified by the methods described herein in a tissue sample or body fluid sample from said subject. Thus, the methods of the present invention encompass methods of monitoring the progress of Alzheimer's disease or of disease progression from MCI to Alzheimer's disease. Also encompassed are prognostic methods, for example prognosis of likely progression from MCi to Alzheimer's disease, or prognosis of likely duration or severity of Alzheimer's disease.

In a preferred embodiment the method comprises:
  (a) establishing a paradigm in which at least one protein is differentially expressed in relevant tissue or body fluid sample from, or representative of, subjects having differential levels of Alzheimer's disease;
  (b) obtaining a sample of the tissue or body fluid sample from the subject;
  (c) determining the presence, absence or degree of expression of the differentially expressed protein or proteins in the sample; and
  (d) relating the determination to the nature or degree of the Alzheimer's disease by reference to a previous correlation between such a determination and clinical information.

In one embodiment, the progression of the disorder may be tracked by using the methods of the invention to determine the severity of the disorder, e.g. global dementia severity). In another embodiment, the duration of the disorder up to the point of assessment may be determined using the methods of the invention. For example, expression of an Ig lambda chain C region (see spot 177, FIG. 6) may correlate with global dementia severity. Expression of a serum albumin precursor (see spot 165, FIG. 6) may show a negative correlation with the duration of the disease.

This method allows the type of Alzheimer's disease of a patient to be correlated to different types to prophylactic or therapeutic treatment available in the art, thereby enhancing the likely response of the patient to the therapy.

In some embodiments, more than one protein is differentially expressed, providing a multi-protein fingerprint of the nature or degree of the Alzheimer's disease. Preferably, at least four proteins are differentially expressed.

Conveniently, the patient sample used in the methods of the invention can be a tissue sample or body fluid sample such as a blood, plasma, serum or urine sample. Use of body fluids such as those listed is preferred because they can be more readily obtained from a subject. This has clear advantages in terms of cost, ease, speed and subject wellbeing. Blood, blood products such as plasma, and urine are particularly preferred.

The step of detecting the differentially expressed protein may be preceded by a depletion step to remove the most abundant proteins from the sample, as described below.

Preferably, at least one of the differentially expressed proteins is a protein shown in FIG. 6, FIG. 7 or FIG. 12. In preferred embodiments, the differentially expressed protein is apolipoprotein A-IV precursor, apolipoprotein C-III precursor, transthyretin, galectin 7, complement C4 precursor, alpha-2-macroglobulin precursor, Ig alpha-1 chain C, histone 2B, Ig lambda chain C region, fibrinogen gamma chain precursor, complement factor H, inter-alpha-trypsin heavy chain H4 precursor, complement C3 precursor, clusterin precursor, gamma or beta actin, haptoglobin precursor or the serum albumin precursor isoform found in spot ID no 2, 14, 15, 123, 165, 176 or 184 of FIG. 6 or fragments thereof. Preferred fragments are a C-terminal fragment of Apo-AIV or a C4 alpha region of complement C4 precursor Lacking the anaphylatoxin domain. For example, the fragment may comprise amino acid residues 270-309 of apolipoprotein A-IV; residues 1446-1744 of complement C4, or may be an N-terminal fragment of apolipoprotein A-IV which migrates as a polypeptide of 10-16 kD or a polypeptide of 28 kD in SDS-PAGE, or a fragment of any of the proteins in FIG. 7 with a molecular weight of 6430, 14640, 27147 or 14646 Da. Other preferred fragments comprise the areas indicated in bold in FIGS. 9, 10, and 13 to 19.

Preferred fragments are less than 50, less than 100, less than 150 less than 200, less than 250, less than 300, less than 350, less than 400, less than 500, less than 600, less than 700, less then 800, less than 900, less than 1000, less than 1100, less than 1200, less than 1300, less than 1400, less than 1500, less than 1600, less than 1700, less than 1800, less than 1900 or less than 2000 amino acids in length.

The expression of certain differentially expressed proteins may be increased in subjects with Alzheimer's disease as compared to control subjects. The expression of other differentially expressed proteins may be decreased in subjects with Alzheimer's disease as compared to control subjects. FIGS. 6, 8 and 12 indicate whether the expression of the proteins disclosed therein is increased or decreased in Alzheimer's versus control subjects. It is thus clear from the figures whether an increase or decrease in expression is indicative of the disease state for all the proteins listed therein. Including the preferred proteins listed above.

Preferably, a differentially expressed protein shows a fold difference in expression of at least 1.5, at least 1.6, at least 1.7, at least 1.8, at least 1.9, at least 2.0, at least 2.5, at least 3, at least 3.5, at least 4, at least 5, at least 10 or more between the level found in patients with Alzheimer's versus control subjects.

The differentially expressed protein may be detected using an antibody specific to that protein, for example in an ELISA assay or Western blotting. Alternatively, the differentially expressed protein may be detected by, amongst others, 2D gel electrophoresis or mass spectrometry techniques including LS/MS/MS, MALDI-TOF or SELDI-TOF. The sample may be immobilised on a solid support for analysis.

In one embodiment, a diagnosis may be made solely on the basis of the pattern of spots on a 2D gel prepared from a subject sample. The pattern of spots obtained from Alzheimer's disease or MCI subjects may be compared directly with the pattern obtained from control subject samples, without the need for identifying individual proteins.

In one embodiment, an antibody sandwich technique where antibodies specific for one or more of the biomarkers is added and the immobilised antibodies capture the biomarker protein. The captured proteins are then detected using a second antibody that may be directly labelled with a signal generating agent (enzyme, fluorescent tag, radiolabel etc.) or may be detected using further amplification (labelled secondary antibody, streptavidin/biotin systems with enzyme, fluorophore, radiolabel etc.). Other immunological methods may include one-dimensional or two-dimensional gel elctrophoresis of patient samples followed by transfer to a solid surface using techniques such as Western blotting and subsequent detection using antibodies specific for the AD biomarkers.

In an alternative embodiment, autoantibodies to the biomarkers may be detected by using the Western blotting approach described above using either samples from a patient or representative of AD and then detecting the presence of antibodies specific for the biomarker that are present in the blood of AD patients but not in controls.

The method may further comprise determining an effective therapy for treating the Alzheimer's disease.

In a further aspect, the present invention provides a method of treatment by the use of an agent that will restore the expression of one or more differentially expressed proteins in the Alzheimer's disease state towards that found in the normal state in order to prevent the development or progression of Alzheimer's disease. Preferably, the expression of the protein is restored to that of the normal state.

In a further aspect, the present invention provides a method whereby the pattern of differentially expressed proteins in a tissue sample or body fluid sample or urine of an individual with Alzheimer's disease is used to predict the most appropriate and effective therapy to alleviate the Alzheimer's disease.

Also provided is a method of screening an agent to determine its usefulness in treating a Alzheimer's disease, the method comprising:

(a) obtaining a sample of relevant tissue taken from, or representative of, a subject having Alzheimer's disease symptoms, who or which has been treated with the agent being screened;

(b) determining the presence, absence or degree of expression of the differentially expressed protein or proteins in the tissue from, or representative of, the treated subject; and, (c) selecting or rejecting the agent according to the extent to which it changes the expression, activity or amount of the differentially expressed protein or proteins in the treated subject having Alzheimer's disease symptoms.

Optionally, the method may further comprise, prior to step (a), the step of establishing a paradigm in which at least one protein is differentially expressed in relevant tissue from, or representative of, subjects having Alzheimer's disease symptoms and normal subjects.

Preferably, the agent is selected if it converts the expression of the differentially expressed protein towards that of a normal subject. More preferably, the agent is selected if it converts the expression of the protein or proteins to that of the normal subject.

Also provided is a method of screening an agent to determine its usefulness in treating Alzheimer's disease, the method comprising:
(a) obtaining over time samples of relevant tissue or body fluid taken from, or representative of, a subject having Alzheimer's disease symptoms, who or which has been treated with the agent being screened;
(b) determining the presence, absence or degree of expression of a differentially expressed protein or proteins in said samples; and,
(c) determining whether the agent affects the change over time in the expression of the differentially expression protein in the treated subject having Alzheimer's disease symptoms.

Optionally, the method may further comprise, prior to step (a), the step of establishing a paradigm in which at least one protein is differentially expressed in relevant tissue or body fluid from, or representative of, subjects having Alzheimer's disease symptoms and normal subjects; and/or
establishing that expression of said differentially expressed protein diverges over time in subjects having Alzheimer's disease symptoms and normal subjects.

Samples taken over time may be taken at intervals of weeks, months or years. For example, samples may be taken at monthly, two-monthly, three-monthly, four-monthly, six-monthly, eight-monthly or twelve-monthly intervals.

A change in expression over time may be an increase or decrease in expression, compared to the initial level of expression in samples from the subject and/or compared to the level of expression in samples from normal subjects. The agent is selected if it slows or stops the change of expression over time.

In the screening methods described above, subjects having differential levels of protein expression comprise:
(a) normal subjects and subjects having Alzheimer's disease symptoms; and,
(b) subjects having Alzheimer's disease symptoms which have not been treated with the agent and subjects Alzheimer's disease which have been treated with the agent.

In alternative embodiments, the subjects having differential levels of protein expression comprise:
(a) normal subjects who have and have not been treated with the agent; and one or both of
(b) subjects having mild cognitive impairment who have and have not been treated with the agent; and
(c) subjects having Alzheimer's disease symptoms who have and have not been treated with the agent.

Preferably, the differential levels of protein expression are not observed in normal subjects who have and have not been treated with the agent.

The subjects having Alzheimer's disease symptoms are preferably human subjects with Alzheimer's disease.

Alternatively, the subjects having Alzheimer's disease symptoms may be an animal model such as mutant amyloid precursor protein (APP) transgenic mice, presenilin-1 (PS-1) transgenic mice, and/or double transgenic APP/PS-1 transgenic mice.

The tissue or body fluid samples may be, for example, brain tissue, blood, plasma, serum, saliva or cerebro-spinal fluid samples.

In one embodiment, the paradigm is established using two-dimensional (2D) gel electrophoresis carried out on the relevant tissue or a protein-containing extract thereof.

In another embodiment, the paradigm is established using SELDI analysis of the relevant tissue or a protein-containing extract thereof. Preferably, the tissue or extract is immobilised on a solid support, for example a chip.

Conveniently, a depletion step may be performed prior to 2D gel electrophoresis or SELDI analysis, to remove the most abundant proteins from the samples and reduce background.

The method may further comprise the step of isolating a differentially expressed protein identified in the method, and optionally the step of characterising the isolated protein.

Preferably, at least one of the differentially expressed proteins is a protein shown in FIG. 6, FIG. 7, FIG. 8 or FIG. 12 or a rodent equivalent thereof. In preferred embodiments, the differentially expressed protein is apolipoprotein A-IV precursor, apolipoprotein C-III precursor, transthyretin, galectin 7, complement C4 precursor, complement factor H, S100 calcium binding protein or ceruloplasmin, inter-alpha-trypsin heavy chain H4 precursor, complement C3 precursor, clusterin precursor, gamma or beta actin, haptoglobin precursor or fragments thereof. Preferred fragments are a C-terminal fragment of Apo-AIV or a C4 alpha region of complement C4 precursor lacking the anaphylatoxin domain. For example, the fragment may comprise amino acid residues 270-309 of apolipoprotein A-IV; residues 1446-1744 of complement C4.

Preferred fragments will comprise one or more of the sequences highlighted in FIGS. 9, 10 and 13-19.

In a further aspect, the invention provides a method of making a pharmaceutical composition which comprises having identified an agent using the method described above, the further step of manufacturing the agent and formulating it with an acceptable carrier to provide the pharmaceutical composition.

In a further aspect, the invention provides a method of identifying a protein which is differentially expressed in relevant tissue or body fluid sample from subjects with mild cognitive impairment and/or subjects with Alzheimer's disease and normal subjects, comprising:
i) immobilising a tissue sample or body fluid sample or protein-containing extract thereof on a solid support
ii) analysing the immobilised proteins by surface enhanced laser desorption time of flight mass spectroscopy
iii) comparing the spectra obtained to detect differences in protein expression between Alzheimer's subjects and normal subjects.

Also provided is protein which is differentially expressed in relevant tissue from, or representative of subjects having differential levels of Alzheimer's disease symptoms and which is as obtainable by the methods described herein or by two-dimensional gel electrophoresis carried out on said tissue or a protein-containing extract thereof, the method comprising:
(a) providing non-linear immobilized pH gradient (ILG) strips of acrylamide polymer 3 mm×180 mm;
(b) rehydrating the IPG strips in a cassette containing 25 ml. of an aqueous solution of urea (8M), 3-[(cholamidopropyl)dimethylammonio]-1-propanesulphonate (CHAPS, 2% w/v), 0.5% IPG Pharmalyte and a trace of Bromophenol Blue;
(c) emptying the cassette of liquid, transferring the strips to an electrophoretic tray fitted with humid electrode wicks, electrodes and sample cups, covering the strips and cups with low viscosity paraffin oil;

(d) applying 200 micrograms of an aqueous solution of dried, powdered material of the relevant body tissue in urea (8M), CHAPS (4% w/v), Tris (40 mM), 0.5% IPG Pharmalyte and a trace of Bromophenol Blue to the sample cups, at the cathodic end of the IPG strips;

(e) carrying out isoelectric focusing on the gel at S1 500V step-n-hold (s/h) for 1 h; S2 500V s/h for 2 h; S3 1000V gradient (G) for 1 h; S4 1000V s/h for 2 h; S5 8000V G for 2 h and S6 8000V s/h for a time effective to enable the proteins to migrate in the strips to their pI-dependent final positions;

(f) equilibrating the strips within the tray with 100 ml of an aqueous solution containing Tris-HCl (50 mM) pH 6.8, urea (6M), glycerol (30% v/v), SDS (2% w/v) and DTT (10 mg/ml);

(g) replacing this solution by 100 ml. of an aqueous solution containing Tris-HCl (50 mM) pH 8.8, urea (6M), glycerol (30% v/v), SDS (2% w/v), iodoacetamide (25 mg/ml) and a trace of Bromophenol Blue and incubating for 20 minutes;

(h) providing a vertical gradient slab gel 160×200×1.5 mm of acrylamide/piperazine-diacrylyl cross-linker (9-16% T/2.6% C), polymerised in the presence of TEMED (0.5% w/v), ammonium persulphate (0.1% w/v) and sodium thiosulphate (5 mM), in Tris-HCl (0.375M) pH 8.8 as leading buffer;

(i) over-layering the gel with sec-butanol for about 2 hours, removing the overlay and replacing it with water;

(j) cutting the IPG gel strips to a size suitable for the second dimensional electrophoresis, removing 6 mm from the anode end and 14 mm from the cathode end;

(k) over-layering the slab gel with an aqueous solution of agarose (0.5% w/v) and Tris-glycine-SDS (25 mM-198 mM-0.1% w/v) as leading buffer, heated to 70° C. and loading the IPG gel strips onto the slab gel through this over-layered solution;

(l) running the second dimensional electrophoresis at a constant current of 40 mA at 8-12° C. for 5 hours; and (m) washing the gel.

This invention is based, in part, on systematic search strategies involving sensitive detection of proteins by 2D-electrophoresis. To aid the identification of differentially expressed protein a standard marker set of proteins such as those available from Genomic Solutions may be run on an extra lane to 2D electrophoresis.

The examples presented below demonstrate the successful use of the experimental paradigms of the invention to identify target proteins associated with Alzheimer's disease.

DEFINITIONS

"Differential expression", as used herein, refers to at least one recognisable difference in tissue or body fluid protein expression. It may be a quantitatively measurable, semi-quantitatively estimatable or qualitatively detectable difference in tissue protein expression. Thus, a differentially expressed protein (herein DEP) may be strongly expressed in tissue in the normal state and less strongly expressed or not expressed at all in tissue in the Alzheimer's disease state. Conversely, it may be strongly expressed in tissue in the Alzheimer's disease state and less strongly expressed or not expressed at all in the normal state. Further, expression may be regarded as differential if the protein undergoes any recognisable change between the two states under comparison.

The term "paradigm" means a prototype example, test model or standard.

Wherever a differentially expressible protein is used in the screening procedure, it follows that there must have been at some time in the past a preliminary step of establishing a paradigm by which the differential expressibility of the protein was pre-determined. Once the paradigm has been established, it need not be re-established on every occasion that a screening procedure is carried out. The term "establishing a paradigm" is to be construed accordingly.

"Relevant tissue" means any tissue involved in brain function, in particular tissue involved in Alzheimer's disease.

"Tissue/Body fluid . . . representative of . . . subjects" means any tissue or body fluid in which the above-mentioned biological change can be simulated for laboratory purposes and includes, for example, a primary cell culture or cell line derived ultimately from relevant tissue.

The term "subjects" includes human and animal subjects.

The treatments referred to above can comprise the administration of one or more drugs or foodstuffs, and/or other factors such as diet or exercise.

The differentially expressed proteins (DEPs) include "fingerprint proteins", "target proteins" or "pathway proteins".

The term "fingerprint protein", as used herein, means a DEP, the expression of which can be used, alone or together with other DEPs, to monitor or assess the condition of a patient suspected of suffering from Alzheimer's disease. Since these proteins will normally be used in combination, especially a combination of four or more, they are conveniently termed "fingerprint proteins", without prejudice to the possibility that on occasions they may be used singly or along with only one or two other proteins for this purpose. Such a fingerprint protein or proteins can be used, for example, to diagnose a particular type of Alzheimer's disease and thence to suggest a specific treatment for it.

The term "diagnosis", as used herein, includes the provision of any information concerning the existence, non-existence or probability of the disorder in a patient. It further includes the provision of information concerning the type or classification of the disorder or of symptoms which are or may be experienced in connection with it. This may include, for example, diagnosis of the severity of the disorder. It encompasses prognosis of the medical course of the disorder, for example its duration, severity and the course of progression from MCI to Alzheimer's disease.

Currently disease status is assessed by duration of disease from inception to present (longer duration equals more severe disease) and clinical assessment measures. These assessment measures include clinical tests for memory and other cognitions, clinical tests for function (abilities of daily living) and clinical assessments of global severity. Trials of potential therapies in AD are currently evaluated against these measures. The FDA and other medicines approval bodies require as part of these assessments measures of both cognition and global function. The Global Dementia Scale is one such measure of global function. It is assessed by rater assessment of severity including cognition and function against a standardised set of severity criteria.

The term "target protein", as used herein, means a DEP, the level or activity of which can be modulated by treatment to alleviate Alzheimer's disease. Modulation of the level or activity of the target protein in a patient may be achieved, for example, by administering the target protein, another protein or gene which interacts with it or an agent which counteracts or reduces it, for example an antibody to the protein, competitive inhibitor of the protein or an agent which acts in the process of transcription or translation of the corresponding gene.

The term "alleviate", as used herein, in relation to Alzheimer's disease means any form of reducing one or more undesired symptoms or effects thereof. Any amelioration of Alzheimer's disease of the patient falls within the term "alleviation". Amelioration may also include slowing down the progression of the disease.

Alternatively or additionally, the DEPs can interact with at least one other protein or with a gene involved in the regulation of brain function. Such other proteins are termed herein "pathway proteins" (PPs). The term is applied to the protein with which the DEP interacts, not to the DEP itself, although a pathway protein can be another DEP.

By way of example, embodiments of the present invention will now be described in more detail with reference to the accompanying figures.

BRIEF DESCRIPTION OF THE FIGURES

FIG. 6 shows differentially expressed proteins identified by 2D gel analysis and mass spectroscopy.

FIG. 7 shows differentially expressed proteins identified by SELDI and LC/MS/MS.

FIG. 8 shows differentially expressed proteins identified by qPST.

FIG. 9 shows the sequence coverage (indicated in bold) obtained for apolipoprotein A-IV (P06727) in the 14.6 kDa band isolated on the Q10 SAX2 SELDI chip. C-terminal residues 270-396 are underlined. The amino acid sequence is SEQ ID NO: 1.

FIG. 10 shows sequence coverage (indicated in bold) obtained for Complement C4 precursor (P01028) in 2DE spot 164. The amino acid sequence is SEQ ID NO: 2.

FIG. 12 lists the differentially expressed spots identified by the pre-depletion analysis. Column 3 gives the accession number for the human protein, column 4 the mean normalised spot volume in the control samples, column 6 the mean normalised spot volume in the disease samples, column 8 the mean normalised spot volume in the disease sample divided by that in the control sample, column 9 the significance (p-value) of the difference in spot volumes compared by Student's t-test, column 10 the number of gels in the control group in which the spot was detected. CV is coefficient of variation.

FIG. 13 shows sequence coverage (indicated in bold) obtained for alpha-2 macroglobulin (P01023) in the pre-depletion analysis. The signal sequence is underlined. The amino acid sequence is SEQ ID NO: 3.

FIG. 14 shows sequence coverage (indicated in bold) obtained for inter-alpha trypsin inhibitor heavy chain H4 precursor (Q14624) in the pre-depletion analysis. The signal sequence is underlined. The amino acid sequence is SEQ ID NO: 4.

FIG. 15 shows sequence coverage (indicated in bold) obtained for complement C3 precursor (P01024) in the pre-depletion analysis. The signal sequence is underlined. The amino acid sequence is SEQ ID NO: 5.

FIG. 16 shows sequence coverage (indicated in bold) obtained for clusterin precursor (P10909) in the pre-depletion analysis. The signal sequence is underlined. The amino acid sequence is SEQ ID NO: 6.

FIG. 17 shows sequence coverage (indicated in bold for spot 832 and bold italic for spot 652) obtained for complement C4 precursor (P01028) in the pre-depletion analysis. The signal sequence is underlined. The amino acid sequence is SEQ ID NO: 7.

FIG. 18 shows sequence coverage (indicated in bold) obtained for gamma actin (P63261) in the pre-depletion analysis. The signal sequence is underlined. The amino acid sequence is SEQ ID NO: 8.

FIG. 19 shows sequence coverage (indicated in bold) obtained for haptoglobin precursor (P00738) in the pre-depletion analysis. The signal sequence is underlined. The amino acid sequence is SEQ ID NO: 9.

DETAILED DESCRIPTION

Figure 1:
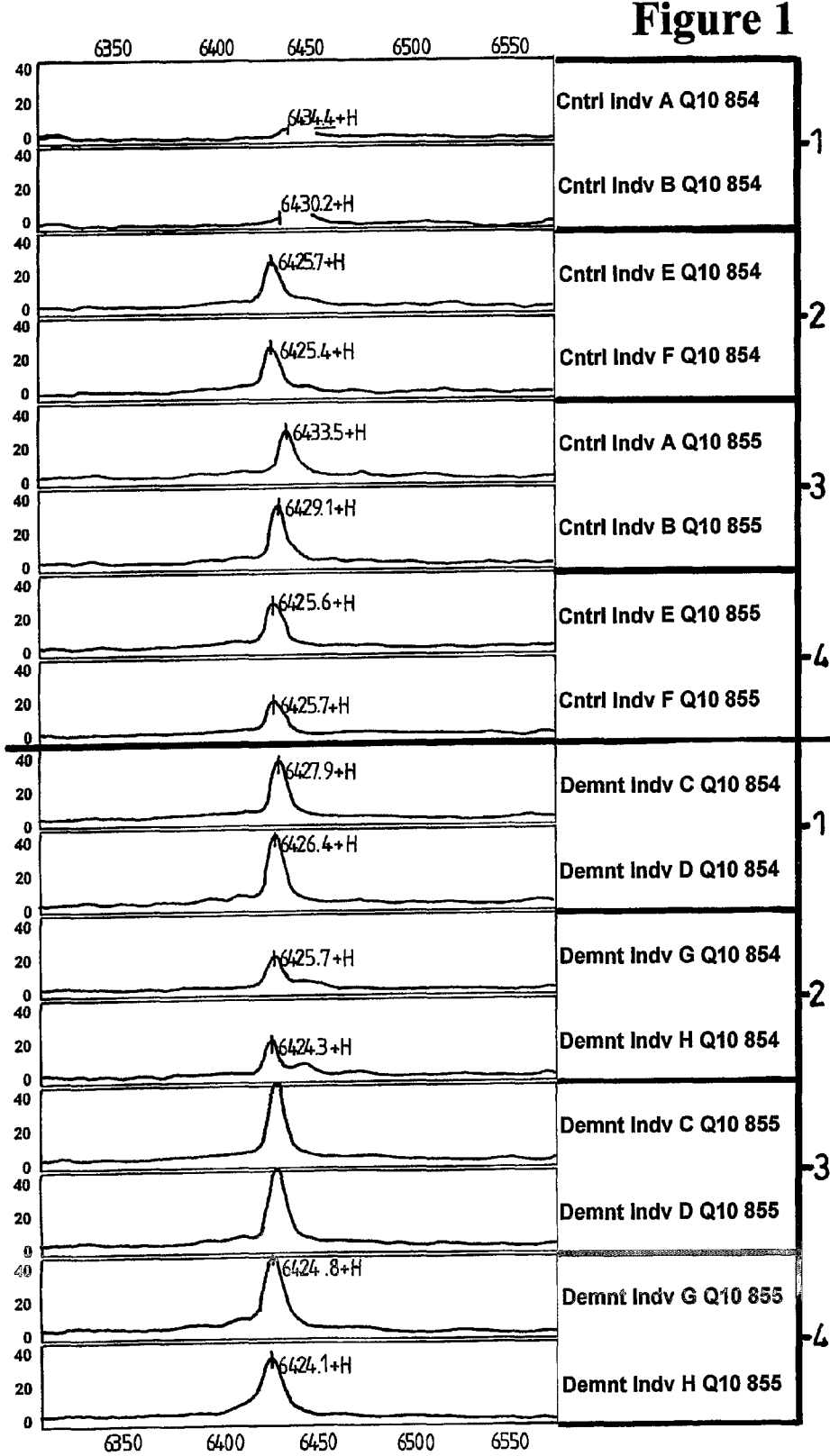
FIG. 1 shows spectra for the 6430 Da peak identified by SELDI analysis in normal (top) and Alzheimer's disease (bottom) subjects.

Methods and compositions for the treatment of Alzheimer's disease. Proteins termed 'target proteins' and/or fingerprint proteins are described which are differentially expressed in Alzheimer's disease states relative to their expression in normal states. Methods for the identification of such fingerprint and target proteins are also described.

'Differential expression' as used herein indicates that a protein is present at different levels in samples from normal and diseased subjects.

Also described below are methods for prognostic and diagnostic evaluation of Alzheimer's disease states and for the identification of subjects exhibiting a predisposition to Alzheimer's disease.

1. Identification of Differentially Expressed and Pathway Proteins

In one embodiment, the present invention concerns methods for the identification of proteins which are involved in Alzheimer's disease. Such proteins may represent proteins which are differentially expressed in Alzheimer's disease states relative to their expression in normal states. Such differentially expressed proteins may represent 'target' or 'fingerprint' proteins.

Methods for the identification of such proteins are described in Section 1. Methods for the further characterisation of such differentially expressed proteins and for their identification as target and/or fingerprint proteins are presented below in Section 1.1.

'Differential expression', as used herein, refers to both qualitative as well as quantitative differences in protein expression. Thus a differentially expressed protein may qualitatively have its expression activated or completely inactivated in normal versus Alzheimer's disease state. Such a qualitatively regulated protein will exhibit an expression pattern within a given tissue, cell type or body fluid sample which is detectable in either control or Alzheimer's disease subject, but not detectable in both. Alternatively, such a qualitatively regulated protein will exhibit an expression pattern within a given tissue, cell type or body fluid sample, which is detectable in either control or Alzheimer's disease subjects but not detectable in both. 'Detectable', as used herein, refers to a protein expression pattern, which are detectable using techniques described herein.

Alternatively, a differentially expressed protein may have its expression modulated, i.e. quantitatively increased or decreased, in normal versus Alzheimer's disease states. The degree to which expression differs in normal versus Alzheimer's disease states need only be large enough to be visualised via standard characterisation techniques, such as silver staining of 2D-electrophoretic gels. Other such standard characterisation techniques by which expression differences may be visualised are well known to those skilled in the art. These include successive chromatographic separations of fractions and comparisons of the peaks, capillary electrophoresis, separations using micro-channel networks, including on a micro-chip, SELDI analysis and qPST analysis.

Chromatographic separations can be carried out by high performance liquid chromatography as described in Pharmacia literature, the chromatogram being obtained in the form of a plot of absorbance of light at 280 nm against time of separation. The material giving incompletely resolved peaks is then re-chromatographed and so on.

Capillary electrophoresis is a technique described in many publications, for example in the literature "Total CE Solutions" supplied by Beckman with their P/ACE 5000 system. The technique depends on applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electroosmotic flow (EOF) of the sample, the positive ions move fastest, followed by uncharged material and negatively charged ions. Thus, proteins are separated essentially according to charge on them.

Micro-channel networks function somewhat like capillaries and can be formed by photcablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form micro-channels. The micro-channel material achieves a separation based on EOF, as for capillary electrophoresis. It is adaptable to micro-chip form, each chip having its own sample injector, separation column and electrochemical detector: see J. S. Rossier et al., 1999, Electrophoresis 20: pages 727-731.

Surface enhanced laser desorption ionisation time of flight mass spectrometry (SELDI-TOF-MS) combined with ProteinChip technology can also provide a rapid and sensitive means of profiling proteins and is used as an alternative to 2D gel electrophoresis in a complementary fashion. The ProteinChip system consists of aluminium chips to which protein samples can be selectively bound on the surface chemistry of the chip (eg. anionic, cationic, hydrophobic, hydrophilic etc). Bound proteins are then co-crystallised with a molar excess of small energy-absorbing molecules. The chip is then analysed by short intense pulses of N2 320 nm UV laser with protein separation and detection being by time of flight mass spectrometry. Spectral profiles of each group within an experiment are compared and any peaks of interest can be further analysed using techniques as described below to establish the identity of the protein.

Quantitative protein sequence tag (qPST) technology may also be used to detect differentially expressed proteins. Briefly, the proteins in the samples for comparison are labelled with a stable isotope tag. A different isotope is used for each sample. The proteins are enzymatically cleaved and the labelled peptides in each sample are quantified by mass spectrometry. In this way, expression of equivalent proteins in the different samples can be compared directly by comparing the intensities of their respective isotopic peaks.

Detection of differentially expressed proteins may be preceded by a depletion step to remove the most abundant proteins from the sample. The large majority of the protein composition of serum/plasma consists of just a few proteins. For example, albumin, which is present at a concentration of 35-50 mg/ml, represents approximately 54% of the total protein content with IgG adding other 16%. In contrast, proteins changing in response to disease, for example as a result of tissue leakage, may circulate at 10 ng/ml. This vast dynamic range of protein concentrations represents a major analytical challenge and to overcome the problem, a multiple affinity depletion column can be used to remove the most highly abundant proteins (eg the 5, 6, 7, 8, 9 or 10 most highly abundant proteins). This enables the detection of changes in lower abundance ranges because more starting material can be used and there is less interference from the highly abundant molecules. Such a depletion strategy can be applied before any detection method.

Differentially expressed proteins may be further described as target proteins and/or fingerprint proteins. 'Fingerprint proteins', as used herein, refer to a differentially expressed protein whose expression pattern may be utilised as part of a prognostic or diagnostic Alzheimer's disease evaluation or which, alternatively, may be used in methods for identifying compounds useful for the treatment of Alzheimer's disease. A fingerprint protein may also have characteristics of a target protein or a pathway protein.

'Target protein', as used herein, refers to a differentially expressed protein involved in Alzheimer's disease such that modulation of the level or activity of the protein may act to prevent the development of Alzheimer's disease. A target protein may also have the characteristics of a fingerprint protein or a pathway protein.

1.1 Characterisation of Differentially Expressed Proteins

Differentially expressed proteins, such as those identified via the methods discussed above, may be further characterised by using, for example, methods such as those discussed herein. Such proteins will be referred to herein as 'identified proteins'.

Analyses such as those described herein, yield information regarding the biological function of the identified proteins. An assessment of the biological function of the differentially expressed proteins, in addition, will allow for their designation as target and/or fingerprint proteins.

Specifically, any of the differentially expressed proteins whose further characterisation indicates that a modulation of the proteins expressed or a modulation of the proteins activity may ameliorate Alzheimer's disease will be designated 'target proteins', as defined above, in Section 1.

Any of the differentially expressed proteins whose expression pattern contributes to a protein 'fingerprint' profile correlative of Alzheimer's disease, will be designated a 'fingerprint protein'. 'Fingerprint profiles' will be more fully discussed below. It should be noted that each of the target proteins may also function as fingerprint proteins.

A variety of techniques can be utilised to further characterise the identified proteins. First, the corresponding nucleotide sequence of the identified protein may be obtained by utilising standard techniques well known to those of skill in the art, may, for example, be used to reveal homologies to one or more known sequence motifs which may yield information regarding the biological function of the identified protein.

Secondly, the biological function of the identified proteins may be more directly assessed by utilising relevant in vivo and in vitro systems. In vivo systems may include, but are not limited to, animal systems which naturally exhibit Alzheimer's disease-like symptoms and/or pathology, or ones which have been engineered to exhibit such symptom and/or pathology. Further, such systems may include systems for the further characterisation of Alzheimer's disease, and may include, but are not limited to, naturally occurring and transgenic animal systems.

In vitro systems may include cell lines derived from such animals or Alzheimer's disease subjects. Animal models may be used to generate cell lines, containing one or more cell types involved in Alzheimer's disease, that can be used as cell culture models for this disorder. While primary cultures derived from the transgenic animals of the invention may be utilised, the generation of continuous cell lines is preferred. For examples of techniques which may be used to derive a continuous cell line from the transgenic animals, see Small, et al., 1985, Mol. Cell. Biol. 5: 642-648.

Preferred transgenic animal models of Alzheimer's disease include mice overexpressing glycogen synthase kinase (GSK) (see Lucas et al (2001) EMBO J. 20, p 27-39), mice overexpressing mutant alleles of APP or PS1 and double (APP/PS1) transgenic mouse models overexpressing mutant alleles of both APP and PS1. Double transgenic mice resulting from a cross between a mutant APP line Tg2576 and a mutant PS1M146L transgenic line is reported in Holcomb et al., Nat. Med. 1998 January; 4(1):97-100).

In further characterising the biological function of the identified proteins, the expression of these proteins may be modulated within the in vivo and/or in vitro systems, i.e. either overexpressed or underexpressed in, for example, transgenic animals and/or cell lines, and its subsequent effect on the system then assayed. Alternatively, the activity of the identified protein may be modulated by either increasing or decreasing the level of activity in the in vivo and/or in vitro system of interest, and its subsequent effect then assayed.

The information obtained through such characterisations may suggest relevant methods for the treatment of Alzheimer's disease using the protein of interest. For example, treatment may include a modulation of protein expression and/or protein activity. Characterisation procedures such as those described herein may indicate where such modulation should involve an increase or a decrease in the expression or activity of the protein of interest. Such methods of treatment are discussed below in Section 4.

2. Differentially Expressed Proteins

Identified proteins, which include differentially expressed proteins such as those identified in Section 1 above, are described herein. Specifically, the amino acid sequences of such identified proteins are described. Further, antibodies directed against the identified protein, and cell- and animal-based models by which the identified proteins may be further characterised and utilised are also discussed in this Section.

2.1 Antibodies Specific for Differentially Expressed or Pathway Proteins

The present invention also relates to methods for the production of antibodies capable of specifically recognising one or more differentially expressed or pathway protein epitopes. Such antibodies may include, but are not limited to, polyclonal antibodies, monoclonal antibodies (mAbs), humanised or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be utilised as part of Alzheimer's disease treatment methods, and/or may be used as part of diagnostic techniques whereby patients may be tested for abnormal levels of fingerprint, target, or pathway gene proteins, or for the presence of abnormal forms of such proteins.

For the production of antibodies to a differentially expressed or pathway protein, various host animals may be immunised by injection with a differentially expressed or pathway protein, or a portion thereof. Such host animals may include, but are not limited to, rabbits, mice and rats, to name but a few. Various adjuvants may be used to increase the immunological response, depending on the host species, including active substances such as lysolecithin, Pluronic polyols, polyanions, peptides, oil emulsions, keyhole limpet hemocyamin, dinitrophenol, and potentially useful human adjuvant such as BCG bacille Calmette-Fuerin) and *Corynebacterium parvum*.

Polyclonal antibodies are heterogeneous populations of antibody molecules derived from the sera of animals immunised with an antigen, such as target proteins, or an antigenic functional derivative thereof. For the production of polyclonal antibodies, host animals such as those described above, may be immunised by injection with differentially expressed or pathway protein supplemented with adjuvants as also described above.

Monoclonal antibodies, which are homogeneous populations of antibodies to a particular antigen, may be obtained by any technique, which provides for the production of antibody molecules by continuous cell lines in culture. These include, but are not limited to, the hybridoma technique of Kohler and Milstein (1975, Nature 256; 495-497; and U.S. Pat. No. 4,376,110), the human β-cell hybridoma technique (Kosbor, et al., 1983, Immunology Today 4: 72; Cole, et al., 1983, Proc. Natl. Acad. Sci. USA 80; 2026-2030), and the EBV-hybridoma technique (Cole, et al., 1985, Monoclonal Antibodies and Cancer Therapy, Alan R. Liss Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of 'chimeric antibodies' (Morrison, et al., 1984, Proc. Natl. Acad. Sci. 81: 6851-6855; Neuberger, et al., 1984, Nature 312: 604-608; Takeda, et al., 1985, Nature 314: 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine in mAb and a human immunoglobulin constant region.

Alternatively, techniques described for the production of single chain antibodies (U.S. Pat. No. 4,946,778; Bird, 1988, Science 242: 423-426; Huston, et al., 1988, Proc. Natl. Acad. Sci. USA 85: 5879-5883; and Ward, et al., 1989, Nature 334: 544-546) can be adapted to produce differentially expressed or pathway protein-single chain antibodies. Single chain antibodies are formed by linking the heavy and light chain fragments of the Fv region via an amino acid bridge, resulting in a single chain polypeptide.

Antibody fragments, which recognise specific epitopes, may be generated by known techniques. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternative, Fab expression libraries may be constructed (Huse, et al., 1989, Science 246: 1275-1281) to allow rapid and easy identification of monoclonal Fab fragments with the desired specificity.

3 Assays for Amelioration of Alzheimer's Disease Symptoms

The differentially expressed proteins described herein may used to test compounds for the ability to prevent or ameliorate Alzheimer's disease.

Such compounds may be tested in human subjects in clinical trials. Any compound which restores the expression of a differentially expressed protein or proteins towards the normal level may be of potential use in treating Alzheimer's disease, i.e. reducing Alzheimer's disease symptoms or slowing the progression of Alzheimer's disease.

With regard to intervention, any treatments that restore or partially restore marker protein expression to normal levels should be considered as candidates for Alzheimer's disease therapeutic intervention. Dosages of test agents may be determined by deriving dose-response curves, as discussed in Section 6 below.

Similarly, any treatments that can prevent the development of Alzheimer's disease or prevent progression to levels of more advanced Alzheimer's disease should be considered as candidates for the Alzheimer's disease therapeutic intervention.

In addition, animal models of Alzheimer's disease, such as those described above, may be used to identify compounds capable of treating Alzheimer's disease symptoms. Such animal models may be used as test substrates for the identification of drugs, pharmaceuticals, therapies and interventions which may be effective in treating such disorders. The response of the animals to the exposure may be monitored by assessing the expression of the marker proteins and comparing it to that of wild-type mice.

Protein expression patterns may be utilised in conjunction with animal model systems to assess the ability of a compound to ameliorate Alzheimer's disease symptoms, or prevent the progression of Alzheimer's disease. For example, the expression pattern of one or more fingerprint proteins may form part of a fingerprint profile, which may then be used in such an assessment. Fingerprint profiles may be characterised for Alzheimer's disease states within the animal model systems. Subsequently, these known fingerprint profiles may be compared to ascertain the effect a test compound has to modify such fingerprint profiles, and to cause the profile to more closely resemble that of a more desirable fingerprint. For example, administration of a compound may cause the fingerprint profile of an Alzheimer's disease model system to more closely resemble the control system, or may prevent further changes in fingerprint profile. Administration of a compound may, alternatively, cause the fingerprint profile of a control system to begin to mimic an Alzheimer's disease state, which may, for example, be used in further characterising the compound of interest, or may be used in the generation of additional animal models.

4. Compounds and Methods for Treatment of Alzheimer's Disease

Described below are methods and compositions whereby Alzheimer's disease symptoms may be ameliorated or the progression of Alzheimer's disease slowed or halted. It is possible that Alzheimer's disease symptoms may be brought about, at least in part, by an abnormal level of target protein, or by the presence of a target protein exhibiting an abnormal activity. As such, the reduction in the level and/or activity of such target protein would bring about the amelioration Alzheimer's disease symptoms. Techniques for the reduction of target protein gene expression levels or target protein activity levels are discussed in Section 4.1.

Alternatively, it is possible that Alzheimer's disease symptoms may be brought about, at least in part, by the absence or reduction of the level of target protein expression, or a reduction in the level of a target protein's activity. As such, an increase in the level of target protein gene expression and/or the activity of such proteins would bring about the amelioration Alzheimer's disease symptoms. Techniques for increasing target protein gene expression levels or target protein activity levels are discussed in Section 4.2.

4.1 Compounds that Inhibit Expression, Synthesis or Activity of Target Proteins

As discussed above, target proteins involved in Alzheimer's disease may cause such disorders via an increased level of target protein activity. A variety of techniques may be utilised to inhibit the expression, synthesis, or activity of such target genes and/or proteins.

For example, compounds which exhibit inhibitory activity, may be used in accordance with the invention to prevent mild cognitive impairment or Alzheimer's disease symptoms. Such molecules may include, but are not limited to, peptides (such as, for example, peptides representing soluble extracellular portions of target protein transmembrane receptors), phosphopeptides, small organic or inorganic molecules, or antibodies (including, for example, polyclonal, monoclonal, humanised, anti-idiotypic, chimeric or single chain antibodies, and FAb, F(ab')$_2$ and FAb expression library fragments, and epitope-binding fragments thereof). Techniques for determination of effective doses and administration of such compounds are described below, in Section 6.1. Inhibitory antibody techniques are further described below, in Section 4.1.2.

Further, antisense, siRNA and ribozyme molecules, which inhibit expression of the target protein gene, may also be used in accordance with the invention to inhibit the aberrant target protein gene activity. Such techniques are described below, in Section 4.1.1; triple helix molecules may be utilised in inhibiting the aberrant target protein gene activity.

4.1.1 Inhibitory Antisense, Ribozyme and Triple Helix Approaches

Antisense, ribozyme and triple helix molecules may be designed to reduce or inhibit either wild type, or if appropriate, mutant target protein gene activity. Techniques for the production and use of such molecules are well known to those of skill in the art.

Antisense RNA and DNA molecules act to directly block the translation of mRNA by hybridising to targeted mRNA and preventing protein translation. With respect to antisense DNA, oligodeoxy-ribonucleotides derived from the translation initiation site, e.g. between the −10 and +10 regions of the target gene nucleotide sequence of interest, are preferred.

Ribozymes are enzymatic RNA molecules capable of catalysing the specific cleavage of RNA. (For a review, see Rossi, J., 1994, Current Biology 4: 469-471). The mechanism of ribozyme action involves sequence specific hybridisation of the ribozyme molecule to complementary target RNA, followed by a endonucleolytic cleavage. The composition of ribozyme molecules must include one or more sequences complementary to the target protein mRNA, and must include the well known catalytic sequence responsible for mRNA cleavage. For this sequence, see U.S. Pat. No. 5,093,246. As such, within the scope of the invention are engineered hammerhead motif ribozyme molecules that specifically and efficiently catalyse endonucleolytic cleavage of RNA sequences encoding target proteins.

Specific ribozyme cleavage sites within any potential RNA target are initially identified by scanning the molecule of interest for ribozyme cleavage sites which include the following sequences, GUA, GUU and GUC. Once identified, short TNA sequences of between 15 and 20 ribonucleotides corresponding to the region of the target protein gene, containing the cleavage site may be evaluated for predicted structural features, such as secondary structure, that may render the oligonucleotide sequence unsuitable. The suitability of candidate sequences may also be evaluated by testing their accessibility to hybridise with complementary oligonucleotides, using ribonuclease protection assays.

RNA interference (RNAi) is a process of sequence-specific, post-transcriptional gene silencing in animals and plants, initiated by double-stranded RNA (dsRNA) that is homologous in sequence to the silenced gene. RNAi is mediated by short double-stranded RNA molecules (small interfering RNAs or siRNAs). siRNAs may be introduced into a cell as short RNA oligonucleotides of 10-15 bp, or as longer dsRNAs which are subsequently cleaved to produce siRNAs. The RNA may be introduced into the cell as RNA, or may be transcribed from a DNA or RNA vector.

siRNA molecules may be synthesized using standard solid or solution phase synthesis techniques which are known in the art. Alternatively, siRNA molecules or longer dsRNA molecules may be made recombinantly by transcription of a nucleic acid sequence, preferably contained within a vector as described below.

Another alternative is the expression of a short hairpin RNA molecule (shRNA) in the cell. shRNAs are more stable than synthetic siRNAs. A shRNA consists of short inverted repeats separated by a small loop sequence. One inverted repeat is complimentary to the gene target. The shRNA is then processed into an siRNA which degrades the target gene mRNA and suppresses expression. shRNAs can produced within a cell by transfecting the cell with a DNA construct encoding the shRNA sequence under control of a RNA polymerase III promoter, such as the human H1 or 7SK promoter. Alternatively, the shRNA may be synthesised exogenously and introduced directly into the cell. Preferably, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementary to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesised in an alternating 5'-3',3'-5' manner, such that they base pair with first one strand of a duplex and then the other, eliminating the necessity for a sizeable stretch of either purines or pyrimidines to be present on one strand of a duplex.

Anti-sense RNA and DNA, siRNAs, ribozyme and triple helix molecules of the invention may be prepared by any method known in the art for the synthesis of DNA and RNA molecules. They include techniques for chemically synthesising oligodeoxyribonucleotides and oligo-ribonucleotides well known in the art such as, for example, solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors, which incorporate suitable RNA polymerase promoters such as the T7 or SP6 polymerase promoters. Alternatively, antisense cDNA constructs that synthesise antisense RNA constitutively inducibly, depending on the promoter used, can be introduced stably into cell lines.

4.1.2 Antibodies for the Inhibition of Target Protein

Antibodies that are both specific for target protein and interfere with its activity may be used to inhibit target protein function. Where desirable, antibodies specific for mutant target protein, which interferes with the activity of such mutant target product, may also be used. Such antibodies may be generated, using standard techniques described in Section 2. above, against the proteins themselves or against peptides corresponding to portions of the proteins. The antibodies include, but are not limited to, polyclonal, monoclonal, Fab fragments, single chain antibodies, chimeric antibodies, etc.

In instances where the target gene protein is intracellular and whole antibodies are used, internalising antibodies may be preferred. However, lipofectin or liposomes may be used to deliver the antibody or a fragment of the Fab region, which binds to the target protein epitope into cells. Where fragments of the antibody are used, the smallest inhibitory fragment, which binds to the target protein's binding domain, is preferred. For example, peptides having an amino acid sequence corresponding to the domain of the variable region of the antibody that binds to the target protein may be used. Such peptides may be synthesised chemically or produced via recombinant DNA technology using methods well known in the art (e.g. see Creighton, 1983, supra; and Sambrook et al, 1989, supra).

Alternatively, single chain neutralising antibodies, which bind to intracellular target protein epitopes, may also be administered. Such single chain antibodies may be administered, for example, by expressing nucleotide sequences encoding single-chain antibodies within the target cell populating by utilising, for example, techniques such as those described in Marasco et al (Marasco, W. et al, 1993, Proc. Natl. Acad. Sci. USA, 90: 7889-7893).

In instances where the target protein is extracellular, or is a transmembrane protein, any of the administration techniques described below, in Section 6, which are appropriate for peptide administration may be utilised to effectively administer inhibitory target protein antibodies to their site of action.

4.2 Methods for Restoring Target Protein Activity

Target proteins that cause Alzheimer's disease may be underexpressed in Alzheimer's disease disorder situations.

Alternatively, the activity of target protein may be diminished, leading to the development of Alzheimer's disease symptoms. Described in this Section are methods whereby the level of target protein may be increased to levels wherein Alzheimer's disease symptoms are prevented or ameliorated. The level of target protein activity may be increased, for example, by either increasing the level of target protein present or by increasing the level of active target protein which is present.

For example, a target protein, at a level sufficient to ameliorate Alzheimer's disease symptoms may be administered to a patient exhibiting such symptoms. Any of the techniques discussed below, in Section 6, may be utilised for such administration. One of skill in the art will readily know how to determine the concentration of effective, non-toxic doses of the normal target protein, utilising techniques such as those described below.

Further, patients may be treated by gene replacement therapy. One or more copies of a normal target protein gene or a portion of the gene that directs the production of a normal target protein with target protein gene function, may be inserted into cells, using vectors which include, but are not limited to, adenovirus, adeno-associated virus, and retrovirus vectors, in addition to other particles that introduce DNA into cells, such as liposomes. Additionally, techniques such as those described above may be utilised for the introduction of normal target protein gene sequences into human cells.

Cells, preferably autologous cells, containing normal target protein gene sequences may then be introduced or reintroduced into the patient at positions which allow for the prevention or amelioration of Alzheimer's disease symptoms. Such cell replacement techniques may be preferred, for example, when the target protein is a secreted, extracellular protein.

Additionally, antibodies may be administered which specifically bind to a target protein and by binding, serve to, either directly or indirectly, activate the target protein function. Such antibodies can include, but are not limited to, polyclonal, monoclonal, FAb fragments, single chain antibodies, chimeric antibodies and the like. The antibodies may be generated using standard techniques such as those described above, in Section 2.3, and may be generated against the protein themselves or against proteins corresponding to portions of the proteins. The antibodies may be administered, for example, according to the techniques described above.

5. Pharmaceutical Preparations and Methods of Administration

The identified compounds, nucleic acid molecules and cells that affect target protein expression, synthesis and/or activity can be administered to a patient at therapeutically effective doses to prevent or to treat or to ameliorate Alzheimer's disease. A therapeutically effective dose refers to that amount of the compound sufficient to result in amelioration of symptoms Alzheimer's disease, or alternatively, to that amount of a nucleic acid molecule sufficient to express a concentration of protein which results in the amelioration of such symptoms.

5.1 Effective Dose

Toxicity and therapeutic efficacy of such compounds can be determined by standard pharmaceutical procedures in cell cultures or experimental animals, e.g. for determining by $ED_{50}$ (the dose therapeutically effective in 50% of the population) and by determining the $ED_{50}$ of any side-effects (toxicity—TD50). The dose ratio between toxic and therapeutic effects is the therapeutic index and it can be expressed as the ratio $TD_{50}/ED_{50}$. Compounds, which exhibit large therapeutic indices, are preferred. While compounds that exhibit toxic side effects may be used, care should be taken to design a delivery system that targets such compounds to the site of affected tissue in order to minimise potential damage to uninfected cells and, thereby, reduce side effects.

The data obtained from the animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilised.

5.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral and rectal administration.

For oral administration, the pharmaceutical compositions may take the form of, for example, tablets or capsules prepared by conventional means with pharmaceutically acceptable excipients such as binding agents (e.g. pre-gelatinised maize starch, polyvinylpyrrolidone or hydroxypropyl methyl-cellulose); fillers (e.g. lactose, microcrystalline cellulose or calcium hydrogen phosphate); lubricants (e.g. magnesium, stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of, e.g. gelatin, for use in an inhaler or insufflator may be formulated containing a powder mix of the compound and a suitable powder base such as lactose or starch.

The compounds may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stablising and/or dispersing agents. Alternatively, the active ingredient may be in powder form for constitution with a suitable vehicle, e.g. sterile pyrogen-free water, before use.

The compounds may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation, for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

The compositions may, if desired, be presented in a pack or dispenser device, which may contain one or more unit dosage forms containing the active ingredient. The pack may, for example, comprise metal or plastic foil, such as blister pack. The pack or dispenser device may be accompanied by instructions for administration.

6. Diagnosis of Alzheimer's Disease

A variety of methods may be employed for the diagnosis of Alzheimer's disease, monitoring progression of mild cognitive impairment and Alzheimer's disease, the predisposition to Alzheimer's disease, and for monitoring the efficacy of any Alzheimer's disease compounds during, for example, clinical trials and for monitoring patients undergoing clinical evaluation for the treatment of Alzheimer's disease. The differentially expressed and fingerprint proteins can also be used to define the nature or degree of Alzheimer's disease to aid in the identification and/or selection of treatments for the disorder.

Alzheimer's disease is characterised by a progressive, insidious onset, two or more deficits in cognitive function, and the absence of any other illnesses that could account for the dementia In addition to memory loss, there may be disorientation, poor attention span, and language impairment. There is likely to be a decline in the activity of daily living, and possibly also impaired perception and personality changes. Behavioural symptoms include delusions, aggression, agitation, anger, wandering, hallucinations, and sleep disturbance.

A simple test assessing orientation, registration, calculations and attention, recall, language, and visual-spatial function may be used for an initial diagnosis.

Structural imaging by standard CT or MRI may also be used. Typically a non-contrast head CT scan suffices, but MRI is preferred for those who have hypertension or diabetes, who are at risk for cerebral vascular disease.

Alzheimer's disease may be confirmed histologically by autopsy or brain biopsy showing neurofibrillary tangles and senile plaques.

Identifying individuals at risk from Alzheimer's disease may involve diagnosis of mild cognitive impairment (MCI). (MCI) may be a transitional state between normal aging and dementia. There are different types of MCI. There may be cognitive impairment in multiple areas of cognitive function, in addition to memory. In some cases, memory is normal but some other domain of cognitive function is abnormal.

Amnestic MCI appears to be a risk state for the development of Alzheimer's disease. Amnestic impairment is defined by subjective memory complaints. These patients have poor memory performance for their age and education on formal testing when compared to age-matched peers. General cognitive functions and the ability to perform the activities of daily living should be entirely normal. The amnestic type of MCI is associated with hippocampal atrophy, neurofibrillary tangles in the medial temporal lobes, and elevated levels of Tau in the cerebrospinal fluid (CSF).

Methods for diagnosing Alzheimer's disease or predisposition to Alzheimer's disease may also, for example, utilise reagents such as the differentially expressed and fingerprint proteins described above, and antibodies directed against differentially expressed, as described above. Specifically, such reagents may be used for the detection of either an over- or an under-abundance of target protein relative to the normal state.

The methods described herein may be performed, for example, by utilising pre-packaged diagnostic kits comprising at least one specific differentially expressed/finger print protein or anti-differentially expressed/fingerprint protein antibody reagent described herein, which may be conveniently used, e.g. in clinical settings, to diagnose patients exhibiting Alzheimer's disease symptoms.

Any cell type, tissue or body fluid in which the fingerprint protein is expressed may be utilised in the diagnostics described herein. Examples of suitable samples types include cell samples, tissue samples, and fluid samples such as blood, urine, serum, saliva, cerebrospinal fluid or plasma.

Among the methods which can be utilised herein, are methods for monitoring the efficacy of compounds in clinical trials for the treatment of Alzheimer's disease. Such compounds can, for example, be compounds such as those described above, in Section 4. Such a method comprises detecting, in a patient sample, a protein, which is differentially expressed in the Alzheimer's disease state relative to its expression in a normal state.

During clinical trials, for example, the expression of a single differentially expressed protein, or alternatively, a fingerprint pattern of a cell involved in Alzheimer's disease can be determined in the presence or absence of the compound being tested. The efficacy of the compound can be followed by comparing the expression data obtained to the corresponding known expression patterns in a normal state. Compounds exhibiting efficacy are those which alter the protein expression and/or the fingerprint pattern to more closely resemble that of the normal state, or which stabilise protein expression and/or the fingerprint pattern i.e. prevent progression of the disease.

The detection of the protein differentially expressed in the Alzheimer's disease state relative to their expression in a normal state can also be used for monitoring the efficacy of potential compounds for the treatment of Alzheimer's disease during clinical trials. During clinical trials, for example, the level and/or activity of the differentially expressed protein can be determined in relevant cells and/or tissues and/or body fluids in the presence or absence of the compound being tested. The efficacy of the compound can be followed by comparing the protein level and/or activity data obtained to the corresponding known levels/activities for the cells and/or tissues and/or body fluids in a normal state. Compounds exhibiting efficacy are those which alter the pattern of the cell and/or tissue sample and/or body fluid from an Alzheimer's disease subject to more closely resemble that of the normal state or which stabilise the pattern i.e. prevent progression of the disease.

EXPERIMENTAL

Subjects

The study population is derived from a large, longitudinally assessed, community based population of people with AD (NINCDS-ADRDA probable), other dementias and normal elderly persons. Samples are available on over 1000 subjects, all whom have detailed clinical assessment. Clinical research data includes systematic diagnostic, cognitive and behavioural assessments. Approximately 50 ml blood (4×10 ml in BD vacutainer K3E 15% tubes and 1×10 ml in exetainer) is drawn from each subject. Subjects have had no food or fluid intake for more than 2 hours prior to collection. One BD vacutainer K3E (plasma) and exetainer (serum) is used for proteomics study. The serum/plasma samples collected for proteomics are spun at 3000 rpm for 8 min within 2 h of collection.

Analysis

Serum/plasma samples were lysed and rehydrated in a 2D lysis buffer consisting of 8M Urea, 2% w/v CHAPS, 0.5% IPG Pharmalyte (pH 3-10; Amersham Biotech, UK. The lysed samples were then subjected to isoelectrofocusing 18 cm 3-10 NL Immobiline pH gradient strips. IPG electrofocusing of the rehydrated strips was carried out for 16 h using the following protocol: S1 500V step-n-hold (s/h; i.e. the electric current applied to the strip is gradually increased in steps holding at particular settings for the times indicated) for 1 h; S2 500V s/h for 2 h; S3 1000V gradient (G) for 1 h; S4 1000V s/h for 2 h; S5 8000V G for 2 h and a final step S6 8000V s/h for 8 h with the IPGphor™.

Electrofocused IPG strips were then equilibrated in a SDS equilibration buffer (50 mM Tris-HCl pH8.8, 6M urea, 30% (v/v) glycerol, 2% SDS, and trace amount of bromophenol blue) with 10 mg/ml dithiothreitol (DTT) for 20 min, followed by 20 min step with 25 mg/ml Iodoacetamide. The equilibrated strips were then separated on a 10% acrylamide second dimension electrophoresis gel using the Ettan Dalt II system.

Following the electrophoresis the gels were placed in separate staining boxes and fixed using 40% ethanol/10% acetic acid for 1 h at room temperature and then stained according to Hochstrasse protocol (Table 1). Gel analysis was performed using the Melanie 3 software and Mann and Whitney rank sum test and False Discovery Rate statistical analysis was carried out to compare subject groups.

TABLE 1

Hochstrasse staining protocol

| Staining step | Time |
|---|---|
| Fix 40% ethanol/10% acetic acid | 1 h |
| Soak in 5% ethanol/5% acetic acid | 3 hr or overnight |
| Wash in water | 5 min |
| Soak in 0.5M Sodium acetate, 1% gluteraldehyde | 1.5 h |
| Wash | 4 × 15 min |
| Soak in 0.05% Naphthalene sulphonic acid | 2 × 30 min |
| Rinse in water | 4 × 15 min |
| Silver stain (12 g silver, 20 ml ammonium hydroxide and 3 ml 10M sodium hydroxide) | 25 min |
| Wash | 4 × 4 min |
| Develop (0.005% citric acid and 0.1% formaldehyde) | As required |
| Stop solution (5% tris and 2% acetic acid) | 1-2 h |
| Storage solution (35% ethanol and 5% glycerol) | |

Sample preparation In-gel reduction, alkylation and digestion (with trypsin) was performed prior to subsequent analysis by mass spectrometry. Cysteine residues were reduced with DTT and derivatized by treatment with iodoacetamide to form stable carbamidcmethyl (CAM) derivatives. Trypsin digestion was carried out overnight at room temperature after an initial 1 hr incubation at 37° C.

MALDI-TOF Mass Spectrometry

The digested sample (3 µl) was desalted and concentrated using ZipTipC18 microtips (Millipore). Peptides were eluted in 4 µl 50% acetonitrile/0.1% trifluoroacetic acid. 0.5 µl was then loaded onto a target plate with 0.5 µl matrix (α-Cyano-4-hydroxy-cinnamic acid). Peptide mass fingerprints were acquired using a Voyager De-Pro, MALDI-TOF mass spectrometer (Applied Biosystems). The mass spectra were acquired in reflectron mode with delayed extraction. An autolytic tryptic peptide of mass 2163.0569 Da was then used to lock mass the acquired spectra, to achieve a mass accuracy of better than 30 ppm.

LC/MS/MS

Peptides were extracted from the gel pieces by a series of acetonitrile and aqueous washes. The extract was pooled with the initial supernatant and lyophilised. Each sample was then resuspended in 6 µL of 50 mM ammonium bicarbonate and analysed by LC/MS/MS. Chromatographic separations were performed using an Ultimate LC system (Dionex, UK). Peptides were resolved by reverse phase chromatography on a 75 µm C18 PepMap column. A gradient of acetonitrile in 0.05% formic acid was delivered to elute the peptides at a flow rate of 200 nl/min. Peptides were ionised by eLectrospray ionisation using a Z-spray source fitted to a QTOFmicro (Waters Corporation). The instrument was set to run in automated switching mode, selecting precursor ions based on their intensity, for sequencing by collision-induced fragmentation. The MS/MS analyses were conducted using collision energy profiles that were chosen based on the m/z and the charge state of the peptide.

Results

Analysis of all control group (n=50) and case group (n=50) 2D gel images and subjecting them to statistical analysis. A total of 16 protein spots show a significant result (p<0.05) (see FIG. 6).

The results shown in FIG. 6 are unambiguous matches as they are based on exact matching of multiple MS/MS spectra. The sequence of selected proteins showing the peptide coverage obtained is given in FIGS. 8 to 10.

Class Prediction Using Peptide Fingerprinting

A class prediction analysis was performed in order to determine whether the pattern of peptide spots on 2DGE could predict caseness as determined clinically. Support Vector Machines (SVM), a supervised machine learning algorithm for prediction of class set in a group based upon a training set of data[13], was used. SVM is most typically used in microarray analyses. However the statistical challenges are similar for proteomics and SVM has previously been used as a class prediction model for various proteomic studies[14,15]. Using GeneSpring (Silicon Genetics) the original 25 cases and 25 controls were designated as a training set and then the replication 25 cases and 25 controls designated as a test set. All identified proteins were used as possible identifiers and with the parameters Polynomial Dot Product Order 1 and Diagonal Scaling Factor 1; 34 of the 50 test-samples were correctly identified as being either cases or controls. Sensitivity was 56% and specificity 80% using SVM analysis of 2DGE data alone.

Identification of Peptides that Differentiate Between Cases and Controls

The normalised spot optical density in both the initial set of cases and controls and the replication set was compared. Mean differences between patients and controls at each spot were compared using the Wilcoxen rank-sum (Mann-Whitney) tests. The p-values for the nul hypothesis of no mean differences were saved, sorted by increasing value and ranked. A false discovery rate index (FDR) was computed as the ratio of the rank number and the theoretical probability (which is the rank number divided by the total number of spots). Fifteen spots were identified to have a FDR of less than 0.50 These were then identified using LC-MS/MS (FIG. 6).

Correlation of Peptide Spots with Clinical Parameters

Although the cases and controls were similarly aged it was possible that the observed peptide or spot differences were due to an association with age, gender or APOE genotype. A correlation analysis was thus performed for the 15 spots that differed between cases and controls in all 100 subjects with age, gender and APOE genotype. Data was first scaled to unit variance so as to standardise the scales upon which the variables were compared (i.e. each value was divided by the standard deviation of all the values for that particular variable). The Pearson correlation coefficient was then calculated. Cases with missing values were excluded pairwise. There were no strong correlations of any spot with age, gender or APOE. Two spots weakly correlated with age, two with gender and one with APOE genotype.

An ideal biomarker would not only be different between cases and controls but would be a marker of disease progression. The 15 spots showing case-control differences in all 50 cases were thus correlated with duration of dementia and severity as measured by MMSE and GDS. Two spots correlated moderately and significantly with measures of disease progression and global dementia severity ($r^2$=0.29 with spot 177) and duration of disease ($r^2$=−0.29 with spot 166). Thus, one peptide—an Ig lambda chain C region (spot 177) correlates with global dementia severity. The other marker of disease progression examined, duration, shows a negative correlation with albumin (Spot 165).

Pre-Depletion Analysis

In these experiments, human plasma samples were depleted to remove the 6 most abundant proteins before the 2D gel electrophoresis step.

Methods 60 human plasma samples (30 Controls and 30 disease subjects) were depleted using a removal column from Agilent. The samples were separated by 2D electrophoresis (pH 3-10 NL, 10% SDS-PAGE, 75 μg protein load). Gels were silver-stained, scanned (8 bit, 200 dpi) and quantitatively analysed with Progenesis. To pick gel plugs from preparative gels, several control samples were mixed together and 3 gels run (2 gels with 205 μg protein load and 1 gel with 350 μg protein load). The same strategy was used with disease samples to run preparative gels. Protein spots were then destained, trypsinated and polypeptides were spotted onto MALDI target with Spot handling workstations (GE Amersham Biosciences). Peptide profiles generated were analysed with Ms-Fit programme in combination with the Swiss-Prot database.

Results

Gel images of proteins extracted from control and disease samples were analysed with Progenesis (v2005). Each group (Control and Disease) were based on 29 analytical gels. Spot detection, matching were performed with Progenesis, then the spot data were exported to Excel and a macro developed in-house was used to calculate coefficient of variation (CV %), T-Test and Regulation facto or change.

Figure 11:
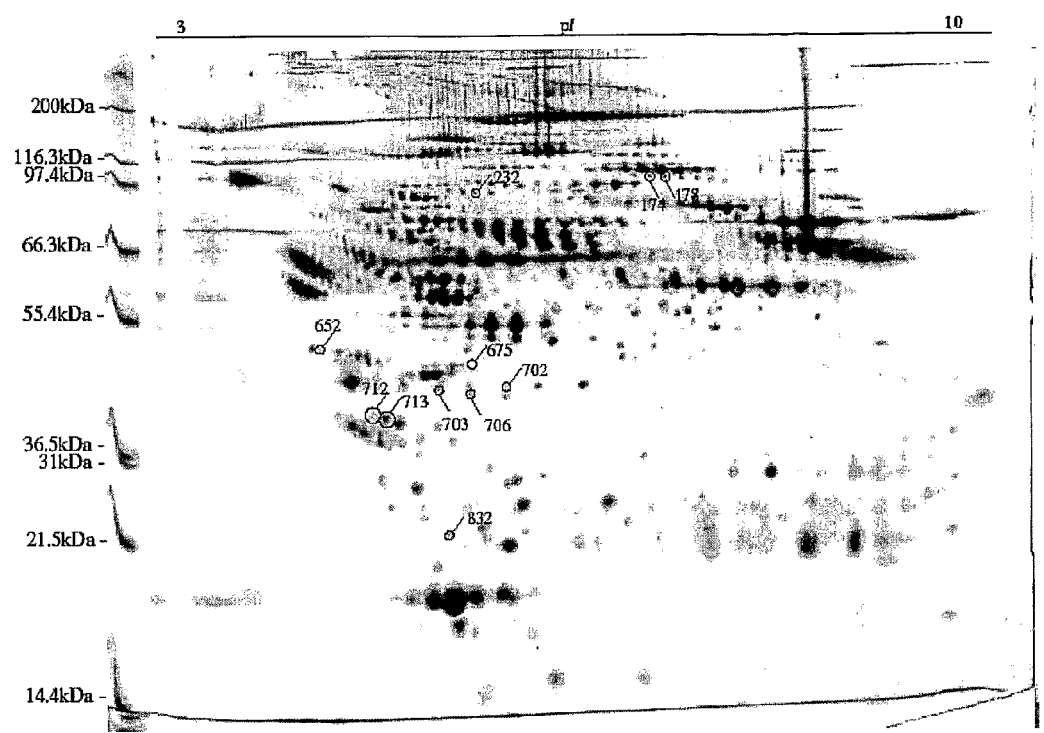
FIG. 11 shows a 2D gel obtained from the pre-depletion analysis. The differentially expressed spots are circled.

11 spots were selected for analysis based on the following selection criteria: spots have to be found within at least 60% of gels, 2-fold up/down regulation and p value<0.005. FIG. 11 displays the location of these 11 spots in the reference gel. This image corresponds to the 2D profile of proteins extracted from a control sample. The normalised volumes of the 11 spots detected in gels was analysed and is given in FIG. 12.

All protein spots were picked from 3 to 6 different preparative gels and submitted to MS analyses. All protein spots were successfully identified as shown in FIG. 12. In the down regulated spots, we found two spots of alpha-2-macroglobulin precursor (174; 178), one spot of inter-alpha-trypsin inhibitor heavy chain H4 precursor (232), one spot of a mix of complement C3 precursor with clusterin precursor (712) as indicated in grey in FIG. 12 and one spot of complement C3 precursor (713). In the up regulated spots, we found two spots of complement C4 precursor (652; 832), one spot of actin (675) and three spots of haptoglobin precursor (702; 703; 706).

To estimate the coverage of proteins identified and to discriminate the different chains or isoforms, for each spot, a common list of peptide masses was established. This list regroups all peptide masses matched corresponding to the same spot picked in 3 to 6 preparative gels. The amino acids belonging to the peptides matched are underlined in FIGS. 13 to 19.

Discussion

The 11 spots analysed identified 7 regulated proteins between control- and disease samples, namely alpha-2-macroglobulin, inter-alpha-trypsin inhibitor heavy chain H4, complement C3, complement C4, actin cytoplasmic and haptoglobin.

Alpha-2-macroglobulin protein is able to inhibit all four classes of proteinases by a unique "trapping" mechanism. The observed molecular weight of the gel spots (~100 kDa, FIG. 11, spots 174; 178), matched by PMF, cover mainly the N-terminus of the protein (FIG. 14). The protein identified may thus correspond to a fragment of the full-length sequence of alpha-2-macroglobulin. As spots identified as alpha-2-macroglobulin belong to the same chain of spots (FIG. 11), it is possible that the difference between the two spots may be due to a post-translation modification.

There are two isoforms of inter-alpha-trypsin inhibitor heavy chain H4. Isoform 1 has 930 amino-acids and isoform 2 has 914 amino-acids. This protein is cleaved by plasma kallikrein to yield 100 kDa and a 35 kDa fragments. The resulting 100 kDa fragment is further converted to a 70 kDa fragment. The masses matched by PMF cover the sequence up to amino acid (aa) 688. This sequence corresponds to isoform 1 and may include the 70 kDa fragment and a short potentially active peptide. In this case, there is good agreement between the theoretical molecular weight and pI (74 kDa and 6.04 respectively) and the observed ones from the gel spot (see FIG. 11, spot 232).

Complement C3 precursor plays a central role in the activation of the complement system. This protein contains two chains (alpha and beta). We identified peptide masses covering the sequence from aa 714 to aa 1360 (FIG. 15), which corresponds to the alpha chain of complement C3. The theoretical molecular weight and pI of the alpha chain (115 kDa and 5.55 respectively) are not in agreement with the observed ones from the gel spots (see FIG. 11, spots 712, 713). The alpha chain is processed into different fragments. It appears that a temporary peptide appearing during the activation of complement system. As spots identified as complement C3 belong to the same chain of spots (FIG. 11), it is possible that the difference is due to a post-translational modification.

Complement C4 plays a central role in the activation of the classical pathway of the complement system. This protein contains three chains (alpha, beta and gamma). We identified peptide masses covering the alpha and beta chains for spot 832 and only alpha chain for spot 652 (FIG. 17). The theoretical molecular weights and pIs of these chains differ from the observed ones from the gel spots (see FIG. 11, spots 652;

832). As for complement C3, clusterin precursor protein contains two chains (alpha and beta). We identified peptide masses covering the alpha and beta chains (FIG. 16). The theoretical molecular weight and pI of clusterin (50 kDa and 5.89 respectively) are in agreement with those from the gel (FIG. 11, spot 712). It appears the full-length protein was identified.

Surface Enhanced Laser Desorption Ionisation Time of Flight Mass Spectrometry [SELDI-TOF-MS].

SELDI-TOF-MS and ProteinChip technology were combined to identify protein peaks differing between Alzheimer's and control subjects, followed by extraction of material from the chips to allow further characterisation of the material and identification of the components present.

METHOD (SELDI Analysis)

The SELDI analysis comprises of a comparison of AD cases and control samples and data has been obtained for both a set of individual samples as well as a pooled set of samples. In each case spectral profiles of sera from control and AD cases were compared.

A). Analysis of a Set of Individuals

Control and AD sera from individuals were run on Q10-SAX2 chips:
n=4 control
n=4 AD Serum samples were prepared fresh by diluting 20 µl serum with 30 µl SELDI lysis buffer. Five microlitres of sample were spotted onto each spot as necessary.

The chips were processed using the following protocol:

Chip Preparation

A hydrophobic ring is drawn around each spot using a PAP pen and the PAP allowed to dry thoroughly by placing chip on the SELDI machine for up to 25 minutes.

Sample Preparation

Serum diluted in SELDI lysis buffer using a 40:60 ratio (40 µL serum+60 µL lysis buffer). Typically, this dilution will render the sample at a 20 mg/mL to 30 mg/mL concentration. Therefore, using a 5 µL aliquot of the lysis buffer sample will enable between 100 µg to 150 µg protein to be loaded on each spot.

Samples are vortexed and incubated on ice until ready to use, then briefly centrifuged samples immediately before use (30 secs, 14,000 rpm).

Chip Equilibration

The chip is placed in a 15 mL Falcon tube and 10-15 mL 100 mM Tris buffer pH 9 at room temperature added, then mixed on a rotary mixer for 5 minutes. The procedure is repeated twice.

Sample Application

After the last equilibration step, the chip is removed and dried carefully with soft tissue. 5 µL of sample is pipetted onto each spot, the chip is placed in a sealed humidity chamber and placed on a shaker for 30 minutes.

Chip Washing

After incubation, the sample is carefully removed from each spot and the chip replaced in the Falcon tube. 10-15 mL 100 mM Tris buffer pH 9 is added, and the Falcon tube mixed on a rotary mixer and for 5 minutes. This is repeat four more times, then the chip washed twice in double distilled water.

Chip Drying

After the last wash step, the chip is removed and dried carefully with soft tissue, then left to air-dry at room temperature for 25 minutes.

SPA Application

2×0.6 µL saturated SPA matrix (freshly made) is pipette onto each spot. The first application is allowed to dry before applying the second 0.6 µL aliquot. The SPA is then left to dry for up to 10 minutes on the SELDI machine.

The chips are then read on the SELDI machine.

The following criteria were applied for data analysis:

Clustering criteria: 5 s/n; 100% spectra; 0.3% mass; 2 s/n; add est. peaks.

Normalisation: Total ion count between 3,000 and 30,000 Da only.

Results

Spot to spot reproducibility between loadings of the same sample was very good. Good correlation was achieved.

Figure 2:
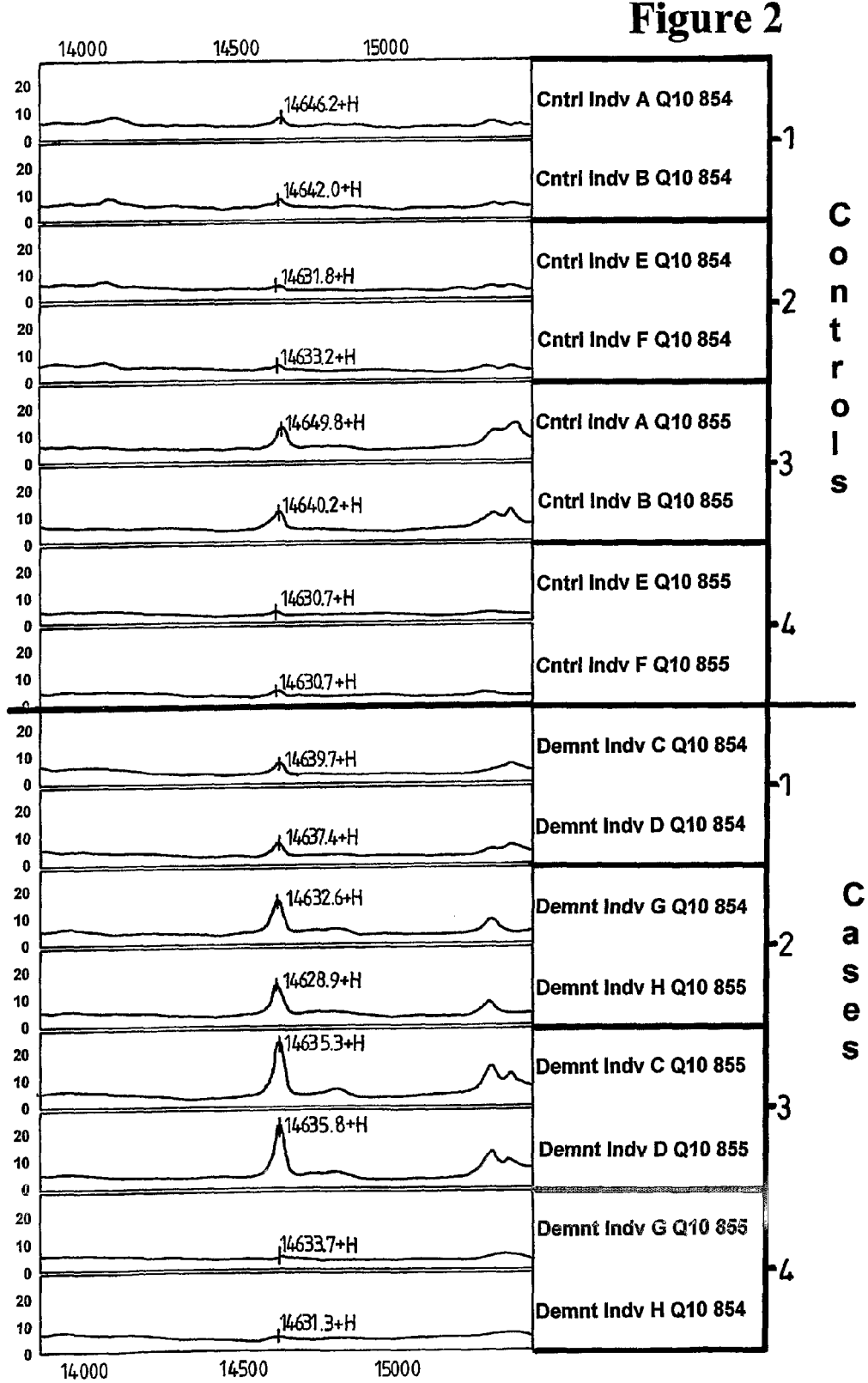
FIG. 2 shows spectra for the 14640 Da peak identified by SELDI analysis in normal (top) and Alzheimer's disease (bottom) subjects.
Figure 3:
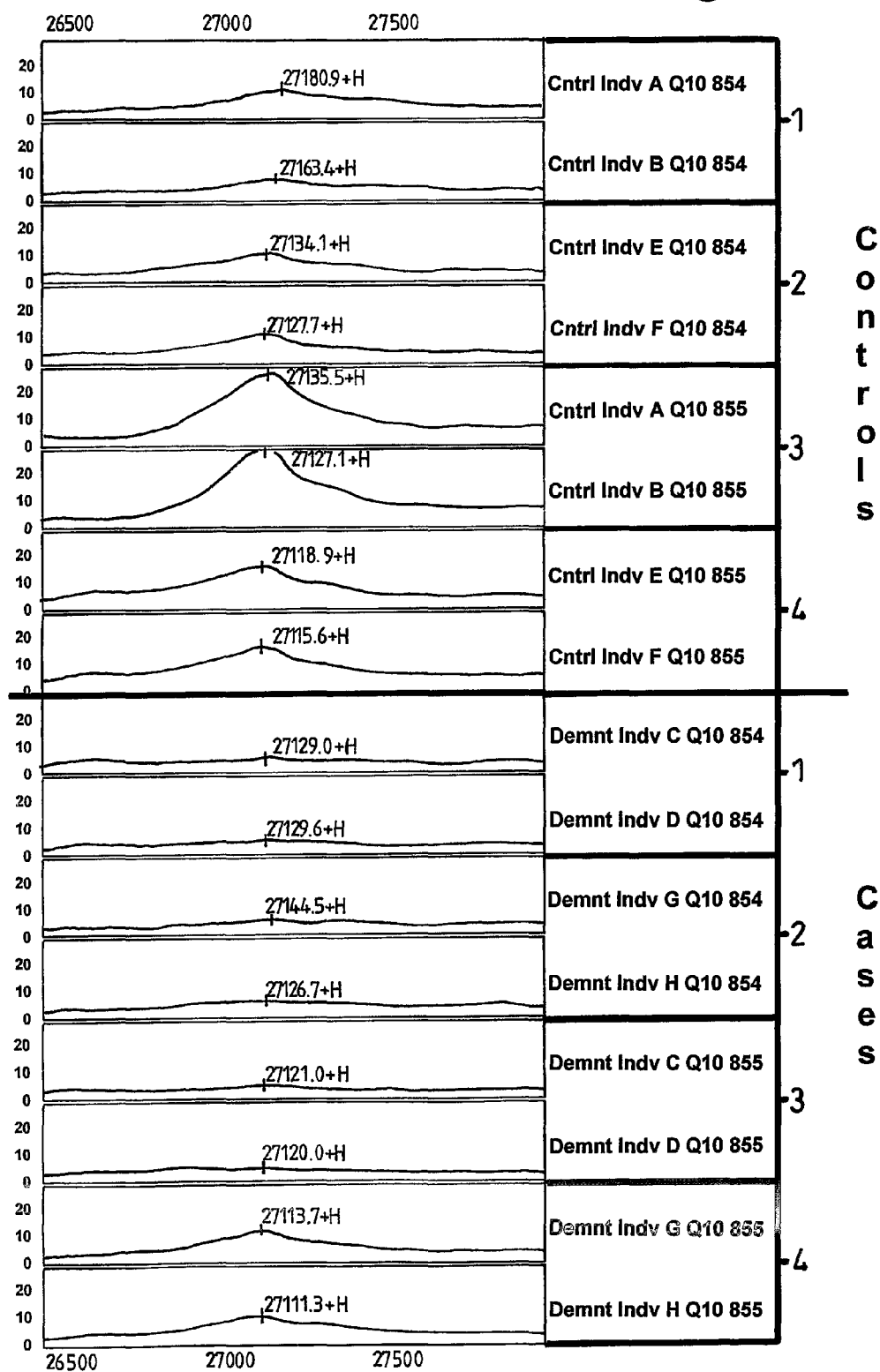
FIG. 3 shows spectra for the 27147 Da peak identified by SELDI analysis in normal (top) and Alzheimer's disease (bottom) subjects.

Patient to patient variability in both control and dementia groups was observed. This may be due to differences in protein amount as well as idiosyncratic differences. Using very stringent clustering, 3 peaks were found to be statistically significant (p=0.05) and these were visually verified to check validity. The three peaks of interest (see FIGS. 1-3) are as follows:

| | |
|---|---|
| Mr 6,430 Da abundance in AD | 1.62 fold increase in p = 0.027 |
| Mr 14,640 Da abundance in AD | 2.29 fold increase in p = 0.036 |
| Mr 27,147 Da abundance in AD | 2.82 fold increase in p = 0.004574 |

B) Analysis of Pooled Sets

A set of pooled samples were analysed using exactly the same methods and criteria as described above. Here, however, we analysed 3 pooled AD samples versus 3 pooled controls where each pool contains serum from at least 25 individuals. In this manner we have encompassed samples from over 75 individuals with AD and compared them against a control cohort representing 75 number of individuals. Pooled groups are described as: AD Pool 1, 2 and 3 comprising of 25, 25 and 25 unique individuals respectively. Similarly, the pooled controls are described as: Control Pool 1, 2 and 3 comprising of 25, 25 and 25 unique individuals respectively.

Results

Using very stringent clustering, 1 peak was found to be statistically significant (p=0.05) and this was visually verified to check validity.

Figure 4:
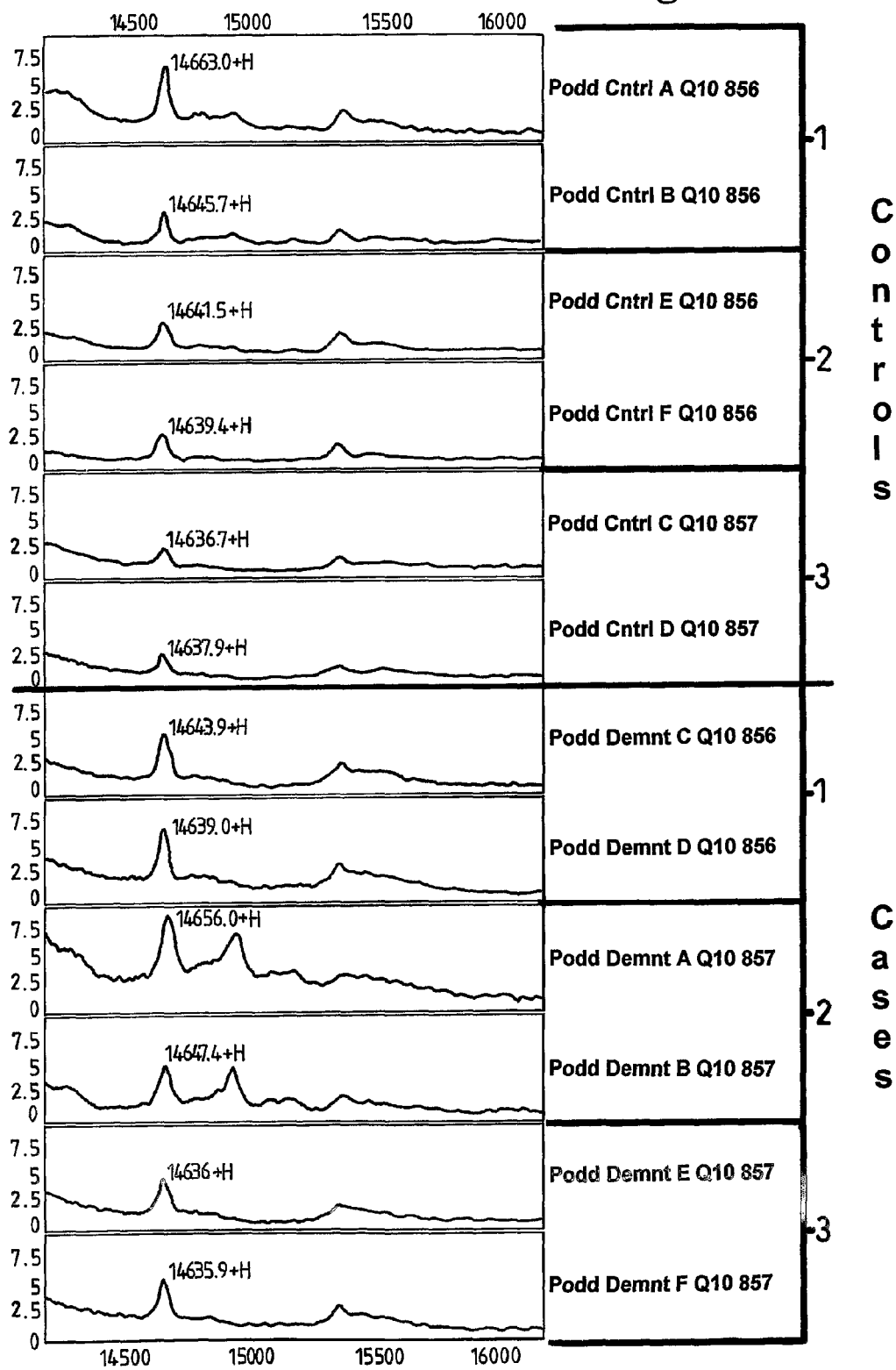
FIG. 4 shows spectra for the 14646 Da peak identified by SELDI analysis in pooled normal (top) and Alzheimer's disease (bottom) subjects.

The peak of interest (see FIG. 4) is as follows:

| | |
|---|---|
| Mr 14,646 Da abundance in AD | 1.72 fold increase in p = 0.037 |

SELDI Peak Identification Strategy

The differentially expressed proteins identified by SELDI analysis were further analysed by SDS-PAGE. Bands corresponding to the MW of differentially expressed proteins were excised for analysis by mass spectroscopy.

Figure 5:
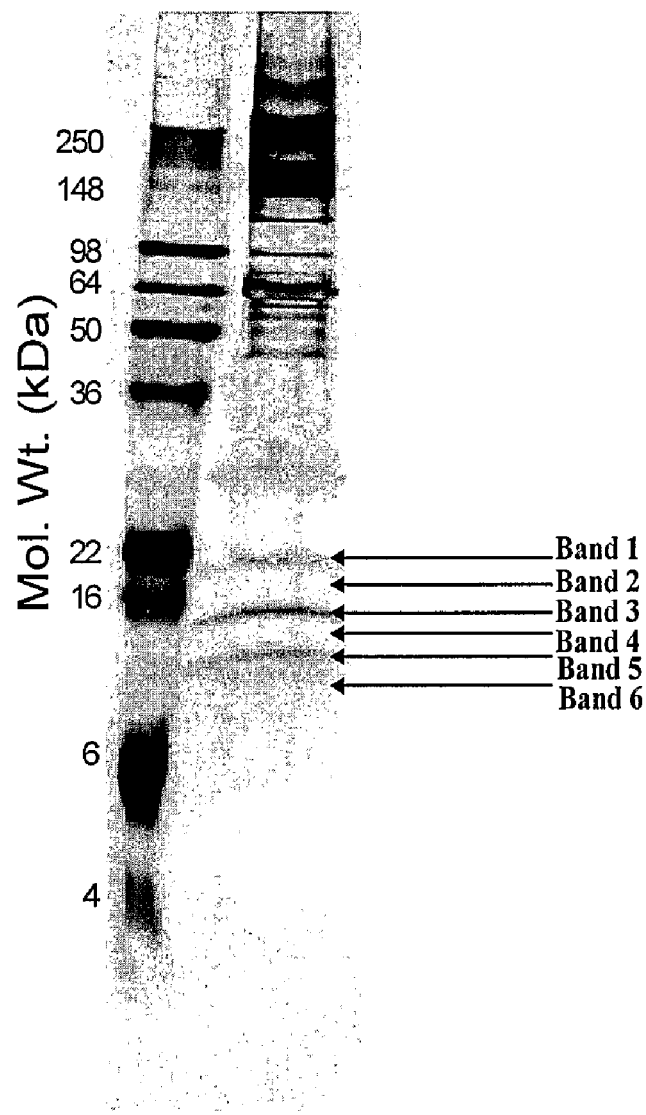
FIG. 5 shows a silver stained gel obtained from material extracted from the chips used for SELDI analysis. The bands (1-6) excised and analysed by LC/MS/MS are indicated by arrows.

Material was extracted from chips Q10 854 & 855 ("individual" samples) by boiling for 10 minutes in Laemmli buffer and control and disease spots were pooled into separate Eppendorf tubes. Extracted material was separated using SDS-PAGE (18%, tris-glycine, Novex) and the gel was initially stained with Colloidal Coomassie Blue (CCB) but no bands were visualised. Subsequently the same gel was re-stained using modified (MS-compatible) silver stain (FIG. 5).

Six bands, between 11 and 20 kDa, were visualised and these were excised from the 1st control lane for analysis by LC/MS/MS as described above.

Identified proteins are shown in FIG. 7.

Further Analysis of Identified Proteins

Apolipoprotein A-IV

Sequence coverage obtained for apolipoprotein A-IV (P06727) is shown in FIG. 9 for the 14.6 kDa band isolated on the Q10 SAX2 SELDI chip The molecular weight of the biomarker of interest observed within the SELDI profiling experiments was determined to be 14640+/−6 Da. The 14.6 kDa species is thought to be a fragment of ApoA-IV based on the facts that the intact protein should be observed at higher mass (45 kDa) and that the peptides observed in the LC/MS/MS analysis only represented the C-terminal region of the protein. The observed molecular weight is in good agreement with the average molecular weight of 14636 Da predicted for residues 270-396 of the sequence defined for apolipoprotein A-IV within the Swiss Prot database entry P06727.

Both authentic full length apolipoprotein A-IV and a C-terminal fragment of apolipoprotein A-IV comprising of residues 270-396 may thus represent serum biomarkers of Alzheimer's disease.

Complement C4 Precursor

Sequence coverage obtained for Complement C4 precursor (P01028) in 2DE spot 164 is shown in FIG. 10. Spot 164 was identified on the basis of several peptides indicated in underlined bold and this defines the protein in Spot 164 as a C-Terminal fragment extending from residues 1466-1744.

Quantitative Protein Sequence Tag (qPST) Analysis 10 disease samples and 10 control samples were individually immunodepleted for the 6 most highly abundant proteins. 2 pools consisting of either the disease or the control samples were generated and applied to the qPST procedure (precleavage with CNBr, labelling with dimethylglycine, trypsination and fractionation by strong cation exchange). The obtained SCX fractions were analysed by LC-MS and LC-MSMS using the QTOF-II instrument following the standard approach (LC-MS and LC-MSMS by three different data acquisition methods)

Results

Identification of Proteins

As stated above, three different MSMS acquisition strategies were employed:

1. Data Dependent Analysis to obtain as many as possible peptide ID's (1 mass window).

2. Data acquisition by an 'include list' containing regulated pairs, ie peptides whose intensity varied between disease and control samples (regulation criteria: $\geq 2/\geq 0.5$)

3. Data acquisition by an 'include list' containing non-paired MS-signals.

Taking all results from these three approaches into account and correcting them for redundancy, 88 protein IDs were obtained.

Directed Searching for Regulated Proteins by Include List (Pairs with a Regulation $\geq 2.0/\geq 0.5$) MSMS Strategy and Crossmatching:

8 peptides were identified which could be crossmatched to regulations. These 8 peptides represent five proteins (the peptide grouping to obtain protein ID's was achieved by the ProteinProphet algorithm).

The ID's of these five proteins are shown in FIG. 8.

The 2 peptides which represent protein 1 also occur in Ig alpha-1 chain C region, so that the protein ID's 1 and 2 in fact represent one ID (Ig alpha-1 chain C region).

The hypothetical protein DKFZP686C02220 is a unique one (in fact, one peptide is unique, the second one can occur in several proteins). This protein has typical signatures of immunoglobulins (regarding InterPro entries), and the second peptide also occurs in Ig alpha-2 chain C region.

The proteins 4 and 5 represent one protein ID (haptoglobin precursor) because both peptides occur also in haptoglobin precursor, but the corresponding peptides were grouped as individual proteins by the algorithm used.

Validation of APO-AIV Fragments Using Western Blotting

Western blotting has been undertaken to confirm that the 14.6 kDa species was a fragment of APO-AIV.

Plasma samples were diluted 1:10 with double distilled water and assayed using a Bradford dye-binding method (diluted samples permit handling of suitably sized aliquot volumes).

SDS-PAGE was carried out using 20 µg sample per lane (2 µg if sample is a denatured primary or secondary antibody) on 16% acrylamide gels, 1.5 mm thick, 10 wells (NOVEX) for 1 hr 80 V; 1½ hrs 125 V. This was followed by Western Blotting onto nitrocellulose membrane at 50 V for 1½ hrs. The blots were probed with the following antibodies:

Anti-ApoA-IV (N-terminal specific), Santa Cruz Biotechnology, Inc.

Anti-ApoA-IV (C-terminal specific), Santa Cruz Biotechnology, Inc.

Both antibodies are affinity purified goat polyclonals raised against a peptide mapping near the amino (N-terminal) or carboxy (C-terminal) terminus of ApoA-IV of human origin. These antibodies were chosen since probing for the N- and C-terminals should increase the chance of detection of the ApoA-IV protein and/or fragments.

Several bands were found that appear to be ApoA-IV specific and also discriminatory for AD. These bands do not appear in the secondary antibody-only control blot for control or AD samples.

Bands 3-6 which are observed in the 10-16 kDa region are discriminatory for AD bands 3-6, but also appear to align with bands in the denatured ApoA-IV antibody lanes. It has also been observed that bands 3-6 are much stronger on blots where the N-terminal specific anti-ApoA-IV antibody has been used.

Two other key bands are observed. Band 1 is observed at approximately 45 kDa and appears to correspond to the full length mature APO-AIV protein. Band 2 is observed at approximately 28 kDa and appears to be an N-terminal fragment of APO-AIV.

Complement Factor H Validation.

Methods

Sample Dilution

Plasma samples were diluted to 1 in 8 in Phosphate buffered saline (PBS). An equal volume of Laemmli 2× sample buffer was added and then boiled for 10 min until use.

Western Blot

SDS gel electrophoresis was performed using the Fisher Scientific 36 well, 1.5 mm gels (all solutions were purchased from National Diagnostics). Samples were separated on a 10% resolving gel with a 4% stacking gel (all solutions were purchased from National Diagnostics). Samples (20 µl) were separated initially for 30 min at 110V and then for 60 min at 150V until the dye front just began to enter the running buffer.

The gel was transferred to PVDF (Amersham Biosciences) using a Semi-dry transblot (Bio-Rad) for 45 min at 15V. The membrane was then blocked in 5% milk made in PBS-Tween and probed with Complement factor H primary antibody (Abcam, UK) overnight at 4° C. The bands were detected with a chemiluminescence Western detection kit (ECL+, Amersham Biosciences) and the membranes were scanned using Storm fluorescence scanner (Amersham Biosciences).

An immunoreactive band was observed at 139 kDa (CfH) and the optical density was quantified using the Image Quant (Amersham Biosciences) software. Analysis was by non-parametric Mann-Whitney using the SPSS package.

Results

Western blot data was acquired from plasma from 128 people with NINCDS-ADRDA probable AD and 78 normal healthy elderly controls. Cases with AD had a 32% increase in CFH (Mann-Whitney; table 2)

TABLE 2

| Diagnosis | Number | Mean CFH | SD | SEM |
|---|---|---|---|---|
| Controls | 128 | 65.6 | 65.5 | 5.8 |
| Probable AD | 78 | 96.0 | 96.8 | 11.0 |

There was a gender difference with a relatively higher CFH value in females overall relatives to males (p=0.05). However CFH was higher in cases with AD relative to controls even when considering genders separately (p<0.01; table 3)

TABLE 3

| Females only | Number | Mean CFH | SEM |
|---|---|---|---|
| Controls | 78 | 73.0 | 8.9 |
| Probable AD | 64 | 102.7 | 13.0 |
| Total | 142 | 86.4 | 7.7 |

A receiver operator curve (ROC) analysis showed that CFH performs better than chance as a diagnostic test.

The references mentioned herein are all expressly incorporated by reference.

REFERENCES

Andreasen, N., C. Hesse, et al. (1999). "Cerebrospinal fluid beta-amyloid(1-42) in Alzheimer disease: differences between early- and late-onset Alzheimer disease and stability during the course of disease." *Arch Neurol* 56(6): 673-80.

Bosman, G. J., I. G. Bartholomeus, et al. (1991). "Erythrocyte membrane characteristics indicate abnormal cellular aging in patients with Alzheimer's disease." *Neurobiol Aging* 12(1): 13-8.

Friedland, R. P. (1993). "Epidemiology, education, and the ecology of Alzheimer's disease." *Neurology* 43(2): 246-9.

Ida, N., T. Hartmann, et al. (1996). "Analysis of heterogeneous A4 peptides in human cerebrospinal fluid and blood by a newly developed sensitive Western blot assay." *J Biol Chem* 271(37): 22908-14.

Kanai, M., E. Matsubara, et al. (1998). "Longitudinal study of cerebrospinal fluid levels of tau, A beta1-40, and A beta1-42(43) in Alzheimer's disease: a study in Japan." *Ann Neurol* 44(1): 17-26.

Kawarabayashi, T., L. H. Younkin, et al. (2001). "Age-dependent changes in brain, CSF, and plasma amyloid (beta) protein in the Tg2576 transgenic mouse model of Alzheimer's disease." *J Neurosci* 21(2): 372-81.

Kosaka, T., M. Imagawa, et al. (1997). "The beta APP717 Alzheimer mutation increases the percentage of plasma amyloid-beta protein ending at A beta42(43)." *Neurology* 48(3): 741-5.

Kuo, Y. M., T. A. Kokjohn, et al. (2000). "Elevated abeta42 in skeletal muscle of Alzheimer disease patients suggests peripheral alterations of AbetaPP metabolism." *Am J Pathol* 156(3): 797-805.

Lindner, M. D., D. D. Gordon, et al. (1993). "Increased levels of truncated nerve growth factor receptor in urine of mildly demented patients with Alzheimer's disease." *Arch Neurol* 50(10): 1054-60.

Pirttila, T., S. Mattinen, et al. (1992). "The decrease of CD8-positive lymphocytes in Alzheimer's disease." *J Neurol Sci* 107(2): 160-5.

Rocca, W. A., A. Hofman, et al. (1991). "Frequency and distribution of Alzheimer's disease in Europe: a collaborative study of 1980-1990 prevalence findings. The EURODEM-Prevalence Research Group." *Ann Neurol* 30(3): 381-90.

Scheuner, D., C. Eckman, et al. (1996). "Secreted amyloid beta-protein similar to that in the senile plaques of Alzheimer's disease is increased in vivo by the presenilin 1 and 2 and APP mutations linked to familial Alzheimer's disease." *Nat Med* 2(8): 864-70.

Ueno, I., T. Sakai, et al. (2000). "Analysis of blood plasma proteins in patients with Alzheimer's disease by two-dimensional electrophoresis, sequence homology and immunodetection." *Electrophoresis* 21(9): 1832-45.

The invention claimed is:

1. A method of diagnosing Alzheimer's disease in a subject, the method comprising detecting a differentially expressed protein, said protein being clusterin precursor protein (Swiss-PROT Accession number (SPN) P10909), in a sample of blood or plasma from said subject, wherein a decrease in the expression of said clusterin precursor protein compared to the expression of said protein in a control subject is indicative of Alzheimer's disease in the subject undergoing diagnosis.

2. A method according to claim 1, wherein the clusterin precursor protein is detected in the sample using (i) an antibody specific to said clusterin precursor protein; (ii) via detection of an autoantibody specific to said clusterin precursor protein, or by mass spectrometry.

3. A method according to claim 1, wherein the clusterin precursor protein is detected using 2D gel electrophoresis.

4. A method according to claim 2 wherein the sample is immobilised on a solid support.

5. A method according to claim 1, wherein said sample is a blood sample.

6. A method according to claim 1, further comprising detecting said clusterin precursor protein in combination with detection of an increase or decrease of the expression level of at least one other differentially expressed protein biomarker of Alzheimer's disease selected from the group consisting of the following proteins or a fragment thereof: apolipoprotein A-IV precursor (SPN P06727), as determined by an increase in the expression thereof, apolipoprotein C-III precursor (SPN P02656), as determined by an increase in the expression thereof, transthyretin (SPN P02766), as determined by an increase in the expression thereof, galectin 7 (SPN P47929), as determined by an increase in the expression thereof, complement C4 precursor (SPN P01028), as determined by an increase in the expression thereof, complement factor H (SPN P08603), as determined by an increase in the expression thereof, S100 calcium binding protein or ceruloplasmin precursor (SPN P00450), as determined by an increase in the expression thereof, histone H2B. a/g/h/k/l (SPN P62807), as determined by a decrease in the expression thereof, Ig lambda chain C region (SPN P01842), as determined by an increase in the expression thereof, inter-alpha-trypsin inhibitor heavy chain H4 precursor (SPN Q14624), as determined by an increase in the expression thereof, complement C3 precursor (SPN P01024), as determined by a decrease in the expression thereof, gamma/beta actin (SPN P63261), as determined by an increase in the expression thereof, haptoglobin precursor (SPN P00738), as determined by an increase in the expression thereof, alpha-2-macroglobulin (SPN P01023), as determined by an increase in the pression thereof and the serum albumin precursor isoform (SPN P02768), as determined by an increase in the expression thereof, said determination(s) being in comparison to the expression of the same protein(s) in a control subject.

7. A method according to claim 6 which comprises detecting more than one differentially expressed protein.

8. A method according to claim 7 which comprises detecting four or more differentially expressed proteins.

* * * * *

UNITED STATES PATENT AND TRADEMARK OFFICE
CERTIFICATE OF CORRECTION

| | | |
|---|---|---|
| PATENT NO. | : 7,897,361 B2 | Page 1 of 1 |
| APPLICATION NO. | : 11/664076 | |
| DATED | : March 1, 2011 | |
| INVENTOR(S) | : Jules Westbrook et al. | |

It is certified that error appears in the above-identified patent and that said Letters Patent is hereby corrected as shown below:

Title Page; item (76);

Page 1, under "Inventors", 6th listed inventor, change "Stephen Lynham" to "Steven Lynham"; and 10th listed inventor, change city of residence from "Offenbad" to "Offenbach".

Signed and Sealed this
Twenty-seventh Day of September, 2011

David J. Kappos
*Director of the United States Patent and Trademark Office*

SEQUENCE LISTING

```
<160> NUMBER OF SEQ ID NOS: 9

<210> SEQ ID NO 1
<211> LENGTH: 396
<212> TYPE: PRT
<213> ORGANISM: Homo Sapiens

<400> SEQUENCE: 1

Met Phe Leu Lys Ala Val Val Leu Thr Leu Ala Leu Val Ala Val Ala
1               5                   10                  15

Gly Ala Arg Ala Glu Val Ser Ala Asp Gln Val Ala Thr Val Met Trp
                20                  25                  30

Asp Tyr Phe Ser Gln Leu Ser Asn Asn Ala Lys Glu Ala Val Glu His
            35                  40                  45

Leu Gln Lys Ser Glu Leu Thr Gln Gln Leu Asn Ala Leu Phe Gln Asp
        50                  55                  60

Lys Leu Gly Glu Val Asn Thr Tyr Ala Gly Asp Leu Gln Lys Lys Leu
65                  70                  75                  80

Val Pro Phe Ala Thr Glu Leu His Glu Arg Leu Ala Lys Asp Ser Glu
                85                  90                  95
```

```
Lys Leu Lys Glu Glu Ile Gly Lys Glu Leu Glu Glu Leu Arg Ala Arg
            100                 105                 110

Leu Leu Pro His Ala Asn Glu Val Ser Gln Lys Ile Gly Asp Asn Leu
        115                 120                 125

Arg Glu Leu Gln Gln Arg Leu Glu Pro Tyr Ala Asp Gln Leu Arg Thr
    130                 135                 140

Gln Val Asn Thr Gln Ala Glu Gln Leu Arg Arg Gln Leu Thr Pro Tyr
145                 150                 155                 160

Ala Gln Arg Met Glu Arg Val Leu Arg Glu Asn Ala Asp Ser Leu Gln
                165                 170                 175

Ala Ser Leu Arg Pro His Ala Asp Glu Leu Lys Ala Lys Ile Asp Gln
            180                 185                 190

Asn Val Glu Glu Leu Lys Gly Arg Leu Thr Pro Tyr Ala Asp Glu Phe
        195                 200                 205

Lys Val Lys Ile Asp Gln Thr Val Glu Glu Leu Arg Arg Ser Leu Ala
210                 215                 220

Pro Tyr Ala Gln Asp Thr Gln Glu Lys Leu Asn His Gln Leu Glu Gly
225                 230                 235                 240

Leu Thr Phe Gln Met Lys Lys Asn Ala Glu Glu Leu Lys Ala Arg Ile
                245                 250                 255

Ser Ala Ser Ala Glu Glu Leu Arg Gln Arg Leu Ala Pro Leu Ala Glu
            260                 265                 270

Asp Val Arg Gly Asn Leu Lys Gly Asn Thr Glu Gly Leu Gln Lys Ser
        275                 280                 285

Leu Ala Glu Leu Gly Gly His Leu Asp Gln Gln Val Glu Glu Phe Arg
    290                 295                 300

Arg Arg Val Glu Pro Tyr Gly Glu Asn Phe Asn Lys Ala Leu Val Gln
305                 310                 315                 320

Gln Met Glu Gln Leu Arg Gln Lys Leu Gly Pro His Ala Gly Asp Val
                325                 330                 335

Glu Gly His Leu Ser Phe Leu Glu Lys Asp Leu Arg Asp Lys Val Asn
            340                 345                 350

Ser Phe Phe Ser Thr Phe Lys Glu Lys Glu Ser Gln Asp Lys Thr Leu
        355                 360                 365

Ser Leu Pro Glu Leu Glu Gln Gln Gln Glu Gln Gln Gln Glu Gln Gln
    370                 375                 380

Gln Glu Gln Val Gln Met Leu Ala Pro Leu Glu Ser
385                 390                 395

<210> SEQ ID NO 2
<211> LENGTH: 1744
<212> TYPE: PRT
<213> ORGANISM: Homo Sapiens

<400> SEQUENCE: 2

Met Arg Leu Leu Trp Gly Leu Ile Trp Ala Ser Ser Phe Phe Thr Leu
  1               5                  10                  15

Ser Leu Gln Lys Pro Arg Leu Leu Leu Phe Ser Pro Ser Val Val His
                20                  25                  30

Leu Gly Val Pro Leu Ser Val Gly Val Gln Leu Gln Asp Val Pro Arg
            35                  40                  45

Gly Gln Val Val Lys Gly Ser Val Phe Leu Arg Asn Pro Ser Arg Asn
        50                  55                  60

Asn Val Pro Cys Ser Pro Lys Val Asp Phe Thr Leu Ser Ser Glu Arg
65                  70                  75                  80
```

-continued

```
Asp Phe Ala Leu Leu Ser Leu Gln Val Pro Leu Lys Asp Ala Lys Ser
                85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
        115                 120                 125

Gly Ile Asn Leu Leu Phe Ser Ser Arg Arg Gly His Leu Phe Leu Gln
    130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
    210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
    290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

Leu Asp Leu Ser Lys Thr Lys Arg His Leu Val Pro Gly Ala Pro Phe
    370                 375                 380

Leu Leu Gln Ala Leu Val Arg Glu Met Ser Gly Ser Pro Ala Ser Gly
385                 390                 395                 400

Ile Pro Val Lys Val Ser Ala Thr Val Ser Ser Pro Gly Ser Val Pro
                405                 410                 415

Glu Val Gln Asp Ile Gln Gln Asn Thr Asp Gly Ser Gly Gln Val Ser
            420                 425                 430

Ile Pro Ile Ile Ile Pro Gln Thr Ile Ser Glu Leu Gln Leu Ser Val
        435                 440                 445

Ser Ala Gly Ser Pro His Pro Ala Ile Ala Arg Leu Thr Val Ala Ala
    450                 455                 460

Pro Pro Ser Gly Gly Pro Gly Phe Leu Ser Ile Glu Arg Pro Asp Ser
465                 470                 475                 480

Arg Pro Pro Arg Val Gly Asp Thr Leu Asn Leu Asn Leu Arg Ala Val
                485                 490                 495

Gly Ser Gly Ala Thr Phe Ser His Tyr Tyr Tyr Met Ile Leu Ser Arg
            500                 505                 510
```

```
Gly Gln Ile Val Phe Met Asn Arg Glu Pro Lys Arg Thr Leu Thr Ser
            515                 520                 525

Val Ser Val Phe Val Asp His His Leu Ala Pro Ser Phe Tyr Phe Val
        530                 535                 540

Ala Phe Tyr Tyr His Gly Asp His Pro Val Ala Asn Ser Leu Arg Val
545                 550                 555                 560

Asp Val Gln Ala Gly Ala Cys Glu Gly Lys Leu Glu Leu Ser Val Asp
            565                 570                 575

Gly Ala Lys Gln Tyr Arg Asn Gly Glu Ser Val Lys Leu His Leu Glu
        580                 585                 590

Thr Asp Ser Leu Ala Leu Val Ala Leu Gly Ala Leu Asp Thr Ala Leu
        595                 600                 605

Tyr Ala Ala Gly Ser Lys Ser His Lys Pro Leu Asn Met Gly Lys Val
610                 615                 620

Phe Glu Ala Met Asn Ser Tyr Asp Leu Gly Cys Gly Pro Gly Gly Gly
625                 630                 635                 640

Asp Ser Ala Leu Gln Val Phe Gln Ala Ala Gly Leu Ala Phe Ser Asp
            645                 650                 655

Gly Asp Gln Trp Thr Leu Ser Arg Lys Arg Leu Ser Cys Pro Lys Glu
        660                 665                 670

Lys Thr Thr Arg Lys Lys Arg Asn Val Asn Phe Gln Lys Ala Ile Asn
        675                 680                 685

Glu Lys Leu Gly Gln Tyr Ala Ser Pro Thr Ala Lys Arg Cys Cys Gln
        690                 695                 700

Asp Gly Val Thr Arg Leu Pro Met Met Arg Ser Cys Glu Gln Arg Ala
705                 710                 715                 720

Ala Arg Val Gln Gln Pro Asp Cys Arg Glu Pro Phe Leu Ser Cys Cys
            725                 730                 735

Gln Phe Ala Glu Ser Leu Arg Lys Lys Ser Arg Asp Lys Gly Gln Ala
        740                 745                 750

Gly Leu Gln Arg Ala Leu Glu Ile Leu Gln Glu Asp Leu Ile Asp
        755                 760                 765

Glu Asp Asp Ile Pro Val Arg Ser Phe Phe Pro Glu Asn Trp Leu Trp
        770                 775                 780

Arg Val Glu Thr Val Asp Arg Phe Gln Ile Leu Thr Leu Trp Leu Pro
785                 790                 795                 800

Asp Ser Leu Thr Thr Trp Glu Ile His Gly Leu Ser Leu Ser Lys Thr
            805                 810                 815

Lys Gly Leu Cys Val Ala Thr Pro Val Gln Leu Arg Val Phe Arg Glu
        820                 825                 830

Phe His Leu His Leu Arg Leu Pro Met Ser Val Arg Arg Phe Glu Gln
        835                 840                 845

Leu Glu Leu Arg Pro Val Leu Tyr Asn Tyr Leu Asp Lys Asn Leu Thr
        850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
            885                 890                 895

Val Ala Phe Ser Val Val Pro Thr Ala Ala Ala Val Ser Leu Lys
        900                 905                 910

Val Val Ala Arg Gly Ser Phe Glu Phe Pro Val Gly Asp Ala Val Ser
        915                 920                 925

Lys Val Leu Gln Ile Glu Lys Glu Gly Ala Ile His Arg Glu Glu Leu
```

-continued

```
             930                 935                 940
Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Phe Asn Ser
                965                 970                 975

Tyr Val Arg Val Thr Ala Ser Asp Pro Leu Asp Thr Leu Gly Ser Glu
                980                 985                 990

Gly Ala Leu Ser Pro Gly Gly Val Ala Ser Leu Leu Arg Leu Pro Arg
                995                 1000                1005

Gly Cys Gly Glu Gln Thr Met Ile Tyr Leu Ala Pro Thr Leu Ala Ala
            1010                1015                1020

Ser Arg Tyr Leu Asp Lys Thr Glu Gln Trp Ser Thr Leu Pro Pro Glu
1025                1030                1035                1040

Thr Lys Asp His Ala Val Asp Leu Ile Gln Lys Gly Tyr Met Arg Ile
                1045                1050                1055

Gln Gln Phe Arg Lys Ala Asp Gly Ser Tyr Ala Ala Trp Leu Ser Arg
            1060                1065                1070

Asp Ser Ser Thr Trp Leu Thr Ala Phe Val Leu Lys Val Leu Ser Leu
            1075                1080                1085

Ala Gln Glu Gln Val Gly Gly Ser Pro Glu Lys Leu Gln Glu Thr Ser
            1090                1095                1100

Asn Trp Leu Leu Ser Gln Gln Gln Ala Asp Gly Ser Phe Gln Asp Pro
1105                1110                1115                1120

Cys Pro Val Leu Asp Arg Ser Met Gln Gly Gly Leu Val Gly Asn Asp
                1125                1130                1135

Glu Thr Val Ala Leu Thr Ala Phe Val Thr Ile Ala Leu His His Gly
            1140                1145                1150

Leu Ala Val Phe Gln Asp Glu Gly Ala Glu Pro Leu Lys Gln Arg Val
            1155                1160                1165

Glu Ala Ser Ile Ser Lys Ala Asn Ser Phe Leu Gly Glu Lys Ala Ser
            1170                1175                1180

Ala Gly Leu Leu Gly Ala His Ala Ala Ala Ile Thr Ala Tyr Ala Leu
1185                1190                1195                1200

Ser Leu Thr Lys Ala Pro Val Asp Leu Leu Gly Val Ala His Asn Asn
                1205                1210                1215

Leu Met Ala Met Ala Gln Glu Thr Gly Asp Asn Leu Tyr Trp Gly Ser
            1220                1225                1230

Val Thr Gly Ser Gln Ser Asn Ala Val Ser Pro Thr Pro Ala Pro Arg
            1235                1240                1245

Asn Pro Ser Asp Pro Met Pro Gln Ala Pro Ala Leu Trp Ile Glu Thr
1250                1255                1260

Thr Ala Tyr Ala Leu Leu His Leu Leu Leu His Glu Gly Lys Ala Glu
1265                1270                1275                1280

Met Ala Asp Gln Ala Ser Ala Trp Leu Thr Arg Gln Gly Ser Phe Gln
            1285                1290                1295

Gly Gly Phe Arg Ser Thr Gln Asp Thr Val Ile Ala Leu Asp Ala Leu
            1300                1305                1310

Ser Ala Tyr Trp Ile Ala Ser His Thr Thr Glu Glu Arg Gly Leu Asn
            1315                1320                1325

Val Thr Leu Ser Ser Thr Gly Arg Asn Gly Phe Lys Ser His Ala Leu
            1330                1335                1340

Gln Leu Asn Asn Arg Gln Ile Arg Gly Leu Glu Glu Glu Leu Gln Phe
1345                1350                1355                1360
```

```
Ser Leu Gly Ser Lys Ile Asn Val Lys Val Gly Gly Asn Ser Lys Gly
            1365                1370                1375

Thr Leu Lys Val Leu Arg Thr Tyr Asn Val Leu Asp Met Lys Asn Thr
        1380                1385                1390

Thr Cys Gln Asp Leu Gln Ile Glu Val Thr Val Lys Gly His Val Glu
    1395                1400                1405

Tyr Thr Met Glu Ala Asn Glu Asp Tyr Glu Asp Tyr Glu Tyr Asp Glu
1410                1415                1420

Leu Pro Ala Lys Asp Asp Pro Asp Ala Pro Leu Gln Pro Val Thr Pro
1425                1430                1435                1440

Leu Gln Leu Phe Glu Gly Arg Arg Asn Arg Arg Arg Glu Ala Pro
                1445                1450                1455

Lys Val Val Glu Glu Gln Glu Ser Arg Val His Tyr Thr Val Cys Ile
            1460                1465                1470

Trp Arg Asn Gly Lys Val Gly Leu Ser Gly Met Ala Ile Ala Asp Val
        1475                1480                1485

Thr Leu Leu Ser Gly Phe His Ala Leu Arg Ala Asp Leu Glu Lys Leu
    1490                1495                1500

Thr Ser Leu Ser Asp Arg Tyr Val Ser His Phe Glu Thr Glu Gly Pro
1505                1510                1515                1520

His Val Leu Leu Tyr Phe Asp Ser Val Pro Thr Ser Arg Glu Cys Val
                1525                1530                1535

Gly Phe Glu Ala Val Gln Glu Val Pro Val Gly Leu Val Gln Pro Ala
            1540                1545                1550

Ser Ala Thr Leu Tyr Asp Tyr Tyr Asn Pro Glu Arg Arg Cys Ser Val
        1555                1560                1565

Phe Tyr Gly Ala Pro Ser Lys Ser Arg Leu Leu Ala Thr Leu Cys Ser
    1570                1575                1580

Ala Glu Val Cys Gln Cys Ala Glu Gly Lys Cys Pro Arg Gln Arg Arg
1585                1590                1595                1600

Ala Leu Glu Arg Gly Leu Gln Asp Glu Asp Gly Tyr Arg Met Lys Phe
                1605                1610                1615

Ala Cys Tyr Tyr Pro Arg Val Glu Tyr Gly Phe Gln Val Lys Val Leu
            1620                1625                1630

Arg Glu Asp Ser Arg Ala Ala Phe Arg Leu Phe Glu Thr Lys Ile Thr
        1635                1640                1645

Gln Val Leu His Phe Thr Lys Asp Val Lys Ala Ala Ala Asn Gln Met
    1650                1655                1660

Arg Asn Phe Leu Val Arg Ala Ser Cys Arg Leu Arg Leu Glu Pro Gly
1665                1670                1675                1680

Lys Glu Tyr Leu Ile Met Gly Leu Asp Gly Ala Thr Tyr Asp Leu Glu
                1685                1690                1695

Gly His Pro Gln Tyr Leu Leu Asp Ser Asn Ser Trp Ile Glu Glu Met
            1700                1705                1710

Pro Ser Glu Arg Leu Cys Arg Ser Thr Arg Gln Arg Ala Ala Cys Ala
        1715                1720                1725

Gln Leu Asn Asp Phe Leu Gln Glu Tyr Gly Thr Gln Gly Cys Gln Val
    1730                1735                1740

<210> SEQ ID NO 3
<211> LENGTH: 1474
<212> TYPE: PRT
<213> ORGANISM: Homo Sapiens

<400> SEQUENCE: 3
```

```
Met Gly Lys Asn Lys Leu Leu His Pro Ser Leu Val Leu Leu Leu
 1               5                  10                  15
Val Leu Leu Pro Thr Asp Ala Ser Val Ser Gly Lys Pro Gln Tyr Met
             20                  25                  30
Val Leu Val Pro Ser Leu Leu His Thr Glu Thr Glu Lys Gly Cys
             35                  40                  45
Val Leu Leu Ser Tyr Leu Asn Glu Thr Val Thr Val Ser Ala Ser Leu
             50                  55                  60
Glu Ser Val Arg Gly Asn Arg Ser Leu Phe Thr Asp Leu Glu Ala Glu
 65              70                  75                  80
Asn Asp Val Leu His Cys Val Ala Phe Ala Val Pro Lys Ser Ser Ser
                 85                  90                  95
Asn Glu Glu Val Met Phe Leu Thr Val Gln Val Lys Gly Pro Thr Gln
                100                 105                 110
Glu Phe Lys Lys Arg Thr Thr Val Met Val Lys Asn Glu Asp Ser Leu
             115                 120                 125
Val Phe Val Gln Thr Asp Lys Ser Ile Tyr Lys Pro Gly Gln Thr Val
             130                 135                 140
Lys Phe Arg Val Val Ser Met Asp Glu Asn Phe His Pro Leu Asn Glu
145                 150                 155                 160
Leu Ile Pro Leu Val Tyr Ile Gln Asp Pro Lys Gly Asn Arg Ile Ala
                165                 170                 175
Gln Trp Gln Ser Phe Gln Leu Glu Gly Gly Leu Lys Gln Phe Ser Phe
             180                 185                 190
Pro Leu Ser Ser Glu Pro Phe Gln Gly Ser Tyr Lys Val Val Val Gln
             195                 200                 205
Lys Lys Ser Gly Gly Arg Thr Glu His Pro Phe Thr Val Glu Glu Phe
210                 215                 220
Val Leu Pro Lys Phe Glu Val Gln Val Thr Val Pro Lys Ile Ile Thr
225                 230                 235                 240
Ile Leu Glu Glu Glu Met Asn Val Ser Val Cys Gly Leu Tyr Thr Tyr
                245                 250                 255
Gly Lys Pro Val Pro Gly His Val Thr Val Ser Ile Cys Arg Lys Tyr
                260                 265                 270
Ser Asp Ala Ser Asp Cys His Gly Glu Asp Ser Gln Ala Phe Cys Glu
             275                 280                 285
Lys Phe Ser Gly Gln Leu Asn Ser His Gly Cys Phe Tyr Gln Gln Val
             290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Glu Gly Thr Val Val Glu Leu Thr
                325                 330                 335
Gly Arg Gln Ser Ser Glu Ile Thr Arg Thr Ile Thr Lys Leu Ser Phe
             340                 345                 350
Val Lys Val Asp Ser His Phe Arg Gln Gly Ile Pro Phe Phe Gly Gln
             355                 360                 365
Val Arg Leu Val Asp Gly Lys Gly Val Pro Ile Pro Asn Lys Val Ile
             370                 375                 380
Phe Ile Arg Gly Asn Glu Ala Asn Tyr Tyr Ser Asn Ala Thr Thr Asp
385                 390                 395                 400
Glu His Gly Leu Val Gln Phe Ser Ile Asn Thr Thr Asn Val Met Gly
                405                 410                 415
Thr Ser Leu Thr Val Arg Val Asn Tyr Lys Asp Arg Ser Pro Cys Tyr
                420                 425                 430
```

```
Gly Tyr Gln Trp Val Ser Glu Glu His Glu Ala His His Thr Ala
        435                 440                 445
Tyr Leu Val Phe Ser Pro Ser Lys Ser Phe Val His Leu Glu Pro Met
    450                 455                 460
Ser His Glu Leu Pro Cys Gly His Thr Gln Thr Val Gln Ala His Tyr
465                 470                 475                 480
Ile Leu Asn Gly Gly Thr Leu Leu Gly Leu Lys Lys Leu Ser Phe Tyr
                485                 490                 495
Tyr Leu Ile Met Ala Lys Gly Gly Ile Val Arg Thr Gly Thr His Gly
            500                 505                 510
Leu Leu Val Lys Gln Glu Asp Met Lys Gly His Phe Ser Ile Ser Ile
        515                 520                 525
Pro Val Lys Ser Asp Ile Ala Pro Val Ala Arg Leu Leu Ile Tyr Ala
    530                 535                 540
Val Leu Pro Thr Gly Asp Val Ile Gly Asp Ser Ala Lys Tyr Asp Val
545                 550                 555                 560
Glu Asn Cys Ile Ala Asn Lys Val Asp Leu Ser Phe Ser Pro Ser Gln
                565                 570                 575
Ser Leu Pro Ala Ser His Ala His Leu Arg Val Thr Ala Ala Pro Gln
            580                 585                 590
Ser Val Cys Ala Leu Arg Ala Val Asp Gln Ser Val Leu Leu Met Lys
        595                 600                 605
Pro Asp Ala Glu Leu Ser Ala Ser Ser Val Tyr Asn Leu Leu Pro Glu
    610                 615                 620
Lys Asp Leu Thr Gly Phe Pro Gly Pro Leu Asn Asp Gln Asp Asp Glu
625                 630                 635                 640
Asp Cys Ile Asn Arg His Asn Val Tyr Ile Asn Gly Ile Thr Tyr Thr
                645                 650                 655
Pro Val Ser Ser Thr Asn Glu Lys Asp Met Tyr Ser Phe Leu Glu Asp
            660                 665                 670
Met Gly Leu Lys Ala Phe Thr Asn Ser Lys Ile Arg Lys Pro Lys Met
        675                 680                 685
Cys Pro Gln Leu Gln Gln Tyr Glu Met His Gly Pro Glu Gly Leu Arg
    690                 695                 700
Val Gly Phe Tyr Glu Ser Asp Val Met Gly Arg Gly His Ala Arg Leu
705                 710                 715                 720
Val His Val Glu Glu Pro His Thr Glu Thr Val Arg Lys Tyr Phe Pro
                725                 730                 735
Glu Thr Trp Ile Trp Asp Leu Val Val Val Asn Ser Ala Gly Val Ala
            740                 745                 750
Glu Val Gly Val Thr Val Pro Asp Thr Ile Thr Glu Trp Lys Ala Gly
        755                 760                 765
Ala Phe Cys Leu Ser Glu Asp Ala Gly Leu Gly Ile Ser Ser Thr Ala
    770                 775                 780
Ser Leu Arg Ala Phe Gln Pro Phe Phe Val Glu Leu Thr Met Pro Tyr
785                 790                 795                 800
Ser Val Ile Arg Gly Glu Ala Phe Thr Leu Lys Ala Thr Val Leu Asn
                805                 810                 815
Tyr Leu Pro Lys Cys Ile Arg Val Ser Val Gln Leu Glu Ala Ser Pro
            820                 825                 830
Ala Phe Leu Ala Val Pro Val Glu Lys Glu Gln Ala Pro His Cys Ile
        835                 840                 845
Cys Ala Asn Gly Arg Gln Thr Val Ser Trp Ala Val Thr Pro Lys Ser
```

```
                850                 855                 860
Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
                900                 905                 910

Glu Thr Thr Phe Asn Ser Leu Leu Cys Pro Ser Gly Gly Glu Val Ser
                915                 920                 925

Glu Glu Leu Ser Leu Lys Leu Pro Pro Asn Val Val Glu Glu Ser Ala
                930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
                980                 985                 990

Thr Gln Gln Leu Thr Pro Glu Val Lys Ser Lys Ala Ile Gly Tyr Leu
                995                 1000                1005

Asn Thr Gly Tyr Gln Arg Gln Leu Asn Tyr Lys His Tyr Asp Gly Ser
     1010                1015                1020

Tyr Ser Thr Phe Gly Glu Arg Tyr Gly Arg Asn Gln Gly Asn Thr Trp
1025                1030                1035                1040

Leu Thr Ala Phe Val Leu Lys Thr Phe Ala Gln Ala Arg Ala Tyr Ile
                1045                1050                1055

Phe Ile Asp Glu Ala His Ile Thr Gln Ala Leu Ile Trp Leu Ser Gln
                1060                1065                1070

Arg Gln Lys Asp Asn Gly Cys Phe Arg Ser Ser Gly Ser Leu Leu Asn
                1075                1080                1085

Asn Ala Ile Lys Gly Gly Val Glu Asp Glu Val Thr Leu Ser Ala Tyr
                1090                1095                1100

Ile Thr Ile Ala Leu Leu Glu Ile Pro Leu Thr Val Thr His Pro Val
1105                1110                1115                1120

Val Arg Asn Ala Leu Phe Cys Leu Glu Ser Ala Trp Lys Thr Ala Gln
                1125                1130                1135

Glu Gly Asp His Gly Ser His Val Tyr Thr Lys Ala Leu Leu Ala Tyr
                1140                1145                1150

Ala Phe Ala Leu Ala Gly Asn Gln Asp Lys Arg Lys Glu Val Leu Lys
                1155                1160                1165

Ser Leu Asn Glu Glu Ala Val Lys Lys Asp Asn Ser Val His Trp Glu
     1170                1175                1180

Arg Pro Gln Lys Pro Lys Ala Pro Val Gly His Phe Tyr Glu Pro Gln
1185                1190                1195                1200

Ala Pro Ser Ala Glu Val Glu Met Thr Ser Tyr Val Leu Leu Ala Tyr
                1205                1210                1215

Leu Thr Ala Gln Pro Ala Pro Thr Ser Glu Asp Leu Thr Ser Ala Thr
                1220                1225                1230

Asn Ile Val Lys Trp Ile Thr Lys Gln Gln Asn Ala Gln Gly Gly Phe
                1235                1240                1245

Ser Ser Thr Gln Asp Thr Val Val Ala Leu His Ala Leu Ser Lys Tyr
     1250                1255                1260

Gly Ala Ala Thr Phe Thr Arg Thr Gly Lys Ala Ala Gln Val Thr Ile
1265                1270                1275                1280
```

Gln Ser Ser Gly Thr Phe Ser Ser Lys Phe Gln Val Asp Asn Asn Asn
                    1285                1290                1295

Arg Leu Leu Leu Gln Gln Val Ser Leu Pro Glu Leu Pro Gly Glu Tyr
            1300                1305                1310

Ser Met Lys Val Thr Gly Glu Gly Cys Val Tyr Leu Gln Thr Ser Leu
        1315                1320                1325

Lys Tyr Asn Ile Leu Pro Glu Lys Glu Glu Phe Pro Phe Ala Leu Gly
            1330                1335                1340

Val Gln Thr Leu Pro Gln Thr Cys Asp Glu Pro Lys Ala His Thr Ser
1345                1350                1355                1360

Phe Gln Ile Ser Leu Ser Val Ser Tyr Thr Gly Ser Arg Ser Ala Ser
                1365                1370                1375

Asn Met Ala Ile Val Asp Val Lys Met Val Ser Gly Phe Ile Pro Leu
            1380                1385                1390

Lys Pro Thr Val Lys Met Leu Glu Arg Ser Asn His Val Ser Arg Thr
            1395                1400                1405

Glu Val Ser Ser Asn His Val Leu Ile Tyr Leu Asp Lys Val Ser Asn
        1410                1415                1420

Gln Thr Leu Ser Leu Phe Phe Thr Val Leu Gln Asp Val Pro Val Arg
1425                1430                1435                1440

Asp Leu Lys Pro Ala Ile Val Lys Val Tyr Asp Tyr Tyr Glu Thr Asp
                1445                1450                1455

Glu Phe Ala Ile Ala Glu Tyr Asn Ala Pro Cys Ser Lys Asp Leu Gly
            1460                1465                1470

Asn Ala

<210> SEQ ID NO 4
<211> LENGTH: 930
<212> TYPE: PRT
<213> ORGANISM: Homo Sapiens

<400> SEQUENCE: 4

Met Lys Pro Pro Arg Pro Val Arg Thr Cys Ser Lys Val Leu Val Leu
1               5                   10                  15

Leu Ser Leu Leu Ala Ile His Gln Thr Thr Ala Glu Lys Asn Gly
            20                  25                  30

Ile Asp Ile Tyr Ser Leu Thr Val Asp Ser Arg Val Ser Ser Arg Phe
        35                  40                  45

Ala His Thr Val Val Thr Ser Arg Val Val Asn Arg Ala Asn Thr Val
    50                  55                  60

Gln Glu Ala Thr Phe Gln Met Glu Leu Pro Lys Lys Ala Phe Ile Thr
65                  70                  75                  80

Asn Phe Ser Met Asn Ile Asp Gly Met Thr Tyr Pro Gly Ile Ile Lys
                85                  90                  95

Glu Lys Ala Glu Ala Gln Ala Gln Tyr Ser Ala Ala Val Ala Lys Gly
            100                 105                 110

Lys Ser Ala Gly Leu Val Lys Ala Thr Gly Arg Asn Met Glu Gln Phe
        115                 120                 125

Gln Val Ser Val Ser Val Ala Pro Asn Ala Lys Ile Thr Phe Glu Leu
    130                 135                 140

Val Tyr Glu Glu Leu Leu Lys Arg Arg Leu Gly Val Tyr Glu Leu Leu
145                 150                 155                 160

Leu Lys Val Arg Pro Gln Gln Leu Val Lys His Leu Gln Met Asp Ile
                165                 170                 175

His Ile Phe Glu Pro Gln Gly Ile Ser Phe Leu Glu Thr Glu Ser Thr

-continued

```
                180                 185                 190
Phe Met Thr Asn Gln Leu Val Asp Ala Leu Thr Thr Trp Gln Asn Lys
            195                 200                 205
Thr Lys Ala His Ile Arg Phe Lys Pro Thr Leu Ser Gln Gln Gln Lys
            210                 215                 220
Ser Pro Glu Gln Gln Glu Thr Val Leu Asp Gly Asn Leu Ile Ile Arg
225                 230                 235                 240
Tyr Asp Val Asp Arg Ala Ile Ser Gly Gly Ser Ile Gln Ile Glu Asn
            245                 250                 255
Gly Tyr Phe Val His Tyr Phe Ala Pro Glu Gly Leu Thr Thr Met Pro
            260                 265                 270
Lys Asn Val Val Phe Val Ile Asp Lys Ser Gly Ser Met Ser Gly Arg
            275                 280                 285
Lys Ile Gln Gln Thr Arg Glu Ala Leu Ile Lys Ile Leu Asp Asp Leu
            290                 295                 300
Ser Pro Arg Asp Gln Phe Asn Leu Ile Val Phe Ser Thr Glu Ala Thr
305                 310                 315                 320
Gln Trp Arg Pro Ser Leu Val Pro Ala Ser Ala Glu Asn Val Asn Lys
            325                 330                 335
Ala Arg Ser Phe Ala Ala Gly Ile Gln Ala Leu Gly Gly Thr Asn Ile
            340                 345                 350
Asn Asp Ala Met Leu Met Ala Val Gln Leu Leu Asp Ser Ser Asn Gln
            355                 360                 365
Glu Glu Arg Leu Pro Glu Gly Ser Val Ser Leu Ile Ile Leu Leu Thr
            370                 375                 380
Asp Gly Asp Pro Thr Val Gly Glu Thr Asn Pro Arg Ser Ile Gln Asn
385                 390                 395                 400
Asn Val Arg Glu Ala Val Ser Gly Arg Tyr Ser Leu Phe Cys Leu Gly
            405                 410                 415
Phe Gly Phe Asp Val Ser Tyr Ala Phe Leu Glu Lys Leu Ala Leu Asp
            420                 425                 430
Asn Gly Gly Leu Ala Arg Arg Ile His Glu Asp Ser Asp Ser Ala Leu
            435                 440                 445
Gln Leu Gln Asp Phe Tyr Gln Glu Val Ala Asn Pro Leu Leu Thr Ala
            450                 455                 460
Val Thr Phe Glu Tyr Pro Ser Asn Ala Val Glu Val Thr Gln Asn
465                 470                 475                 480
Asn Phe Arg Leu Leu Phe Lys Gly Ser Glu Met Val Val Ala Gly Lys
            485                 490                 495
Leu Gln Asp Arg Gly Pro Asp Val Leu Thr Ala Thr Val Ser Gly Lys
            500                 505                 510
Leu Pro Thr Gln Asn Ile Thr Phe Gln Thr Glu Ser Ser Val Ala Glu
            515                 520                 525
Gln Glu Ala Glu Phe Gln Ser Pro Lys Tyr Ile Phe His Asn Phe Met
            530                 535                 540
Glu Arg Leu Trp Ala Tyr Leu Thr Ile Gln Gln Leu Leu Glu Gln Thr
545                 550                 555                 560
Val Ser Ala Ser Asp Ala Asp Gln Gln Ala Leu Arg Asn Gln Ala Leu
            565                 570                 575
Asn Leu Ser Leu Ala Tyr Ser Phe Val Thr Pro Leu Thr Ser Met Val
            580                 585                 590
Val Thr Lys Pro Asp Asp Gln Glu Gln Ser Gln Val Ala Glu Lys Pro
            595                 600                 605
```

```
Met Glu Gly Glu Ser Arg Asn Arg Asn Val His Ser Gly Ser Thr Phe
    610                 615                 620
Phe Lys Tyr Tyr Leu Gln Gly Ala Lys Ile Pro Lys Pro Glu Ala Ser
625                 630                 635                 640
Phe Ser Pro Arg Arg Gly Trp Asn Arg Gln Ala Gly Ala Ala Gly Ser
                645                 650                 655
Arg Met Asn Phe Arg Pro Gly Val Leu Ser Ser Arg Gln Leu Gly Leu
            660                 665                 670
Pro Gly Pro Pro Asp Val Pro Asp His Ala Ala Tyr His Pro Phe Arg
        675                 680                 685
Arg Leu Ala Ile Leu Pro Ala Ser Ala Pro Pro Ala Thr Ser Asn Pro
    690                 695                 700
Asp Pro Ala Val Ser Arg Val Met Asn Met Lys Ile Glu Glu Thr Thr
705                 710                 715                 720
Met Thr Thr Gln Thr Pro Ala Pro Ile Gln Ala Pro Ser Ala Ile Leu
                725                 730                 735
Pro Leu Pro Gly Gln Ser Val Glu Arg Leu Cys Val Asp Pro Arg His
            740                 745                 750
Arg Gln Gly Pro Val Asn Leu Leu Ser Asp Pro Glu Gln Gly Val Glu
        755                 760                 765
Val Thr Gly Gln Tyr Glu Arg Glu Lys Ala Gly Phe Ser Trp Ile Glu
    770                 775                 780
Val Thr Phe Lys Asn Pro Leu Val Trp Val His Ala Ser Pro Glu His
785                 790                 795                 800
Val Val Val Thr Arg Asn Arg Ser Ser Ala Tyr Lys Trp Lys Glu
                805                 810                 815
Thr Leu Phe Ser Val Met Pro Gly Leu Lys Met Thr Met Asp Lys Thr
            820                 825                 830
Gly Leu Leu Leu Leu Ser Asp Pro Asp Lys Val Thr Ile Gly Leu Leu
        835                 840                 845
Phe Trp Asp Gly Arg Gly Glu Gly Leu Arg Leu Leu Leu Arg Asp Thr
    850                 855                 860
Asp Arg Phe Ser Ser His Val Gly Gly Thr Leu Gly Gln Phe Tyr Gln
865                 870                 875                 880
Glu Val Leu Trp Gly Ser Pro Ala Ala Ser Asp Asp Gly Arg Arg Thr
                885                 890                 895
Leu Arg Val Gln Gly Asn Asp His Ser Ala Thr Arg Glu Arg Arg Leu
            900                 905                 910
Asp Tyr Gln Glu Gly Pro Pro Gly Val Glu Ile Ser Cys Trp Ser Val
        915                 920                 925
Glu Leu
    930

<210> SEQ ID NO 5
<211> LENGTH: 1663
<212> TYPE: PRT
<213> ORGANISM: Homo Sapiens

<400> SEQUENCE: 5

Met Gly Pro Thr Ser Gly Pro Ser Leu Leu Leu Leu Leu Thr His
  1               5                  10                  15
Leu Pro Leu Ala Leu Gly Ser Pro Met Tyr Ser Ile Ile Thr Pro Asn
                20                  25                  30
Ile Leu Arg Leu Glu Ser Glu Glu Thr Met Val Leu Glu Ala His Asp
            35                  40                  45
```

-continued

```
Ala Gln Gly Asp Val Pro Val Thr Val Thr Val His Asp Phe Pro Gly
 50                  55                  60
Lys Lys Leu Val Leu Ser Ser Glu Lys Thr Val Leu Thr Pro Ala Thr
 65                  70                  75                  80
Asn His Met Gly Asn Val Thr Phe Thr Ile Pro Ala Asn Arg Glu Phe
                     85                  90                  95
Lys Ser Glu Lys Gly Arg Asn Lys Phe Val Thr Val Gln Ala Thr Phe
                100                 105                 110
Gly Thr Gln Val Val Glu Lys Val Leu Val Ser Leu Gln Ser Gly
                115                 120                 125
Tyr Leu Phe Ile Gln Thr Asp Lys Thr Ile Tyr Thr Pro Gly Ser Thr
130                 135                 140
Val Leu Tyr Arg Ile Phe Thr Val Asn His Lys Leu Leu Pro Val Gly
145                 150                 155                 160
Arg Thr Val Met Val Asn Ile Glu Asn Pro Glu Gly Ile Pro Val Lys
                    165                 170                 175
Gln Asp Ser Leu Ser Ser Gln Asn Gln Leu Gly Val Leu Pro Leu Ser
                180                 185                 190
Trp Asp Ile Pro Glu Leu Val Asn Met Gly Gln Trp Lys Ile Arg Ala
            195                 200                 205
Tyr Tyr Glu Asn Ser Pro Gln Gln Val Phe Ser Thr Glu Phe Glu Val
        210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                    245                 250                 255
Ala Arg Phe Leu Tyr Gly Lys Lys Val Glu Gly Thr Ala Phe Val Ile
                260                 265                 270
Phe Gly Ile Gln Asp Gly Glu Gln Arg Ile Ser Leu Pro Glu Ser Leu
            275                 280                 285
Lys Arg Ile Pro Ile Glu Asp Gly Ser Gly Glu Val Val Leu Ser Arg
        290                 295                 300
Lys Val Leu Leu Asp Gly Val Gln Asn Leu Arg Ala Glu Asp Leu Val
305                 310                 315                 320
Gly Lys Ser Leu Tyr Val Ser Ala Thr Val Ile Leu His Ser Gly Ser
                    325                 330                 335
Asp Met Val Gln Ala Glu Arg Ser Gly Ile Pro Ile Val Thr Ser Pro
                340                 345                 350
Tyr Gln Ile His Phe Thr Lys Thr Pro Lys Tyr Phe Lys Pro Gly Met
            355                 360                 365
Pro Phe Asp Leu Met Val Phe Val Thr Asn Pro Asp Gly Ser Pro Ala
        370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                    405                 410                 415
Gln Lys Pro Leu Ser Ile Thr Val Arg Thr Lys Lys Gln Glu Leu Ser
                420                 425                 430
Glu Ala Glu Gln Ala Thr Arg Thr Met Gln Ala Leu Pro Tyr Ser Thr
            435                 440                 445
Val Gly Asn Ser Asn Asn Tyr Leu His Leu Ser Val Leu Arg Thr Glu
        450                 455                 460
Leu Arg Pro Gly Glu Thr Leu Asn Val Asn Phe Leu Leu Arg Met Asp
465                 470                 475                 480
```

```
Arg Ala His Glu Ala Lys Ile Arg Tyr Tyr Thr Tyr Leu Ile Met Asn
            485                 490                 495
Lys Gly Arg Leu Leu Lys Ala Gly Arg Gln Val Arg Glu Pro Gly Gln
            500                 505                 510
Asp Leu Val Val Leu Pro Leu Ser Ile Thr Thr Asp Phe Ile Pro Ser
            515                 520                 525
Phe Arg Leu Val Ala Tyr Tyr Thr Leu Ile Gly Ala Ser Gly Gln Arg
            530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
            565                 570                 575
Pro Gly Gln Gln Met Thr Leu Lys Ile Glu Gly Asp His Gly Ala Arg
            580                 585                 590
Val Val Leu Val Ala Val Asp Lys Gly Val Phe Val Leu Asn Lys Lys
            595                 600                 605
Asn Lys Leu Thr Gln Ser Lys Ile Trp Asp Val Val Glu Lys Ala Asp
            610                 615                 620
Ile Gly Cys Thr Pro Gly Ser Gly Lys Asp Tyr Ala Gly Val Phe Ser
625                 630                 635                 640
Asp Ala Gly Leu Thr Phe Thr Ser Ser Gly Gln Gln Thr Ala Gln
            645                 650                 655
Arg Ala Glu Leu Gln Cys Pro Gln Pro Ala Ala Arg Arg Arg Arg Ser
            660                 665                 670
Val Gln Leu Thr Glu Lys Arg Met Asp Lys Val Gly Lys Tyr Pro Lys
            675                 680                 685
Glu Leu Arg Lys Cys Cys Glu Asp Gly Met Arg Glu Asn Pro Met Arg
            690                 695                 700
Phe Ser Cys Gln Arg Arg Thr Arg Phe Ile Ser Leu Gly Glu Ala Cys
705                 710                 715                 720
Lys Lys Val Phe Leu Asp Cys Cys Asn Tyr Ile Thr Glu Leu Arg Arg
            725                 730                 735
Gln His Ala Arg Ala Ser His Leu Gly Leu Ala Arg Ser Asn Leu Asp
            740                 745                 750
Glu Asp Ile Ile Ala Glu Glu Asn Ile Val Ser Arg Ser Glu Phe Pro
            755                 760                 765
Glu Ser Trp Leu Trp Asn Val Glu Asp Leu Lys Glu Pro Pro Lys Asn
770                 775                 780
Gly Ile Ser Thr Lys Leu Met Asn Ile Phe Leu Lys Asp Ser Ile Thr
785                 790                 795                 800
Thr Trp Glu Ile Leu Ala Val Ser Met Ser Asp Lys Lys Gly Ile Cys
            805                 810                 815
Val Ala Asp Pro Phe Glu Val Thr Val Met Gln Asp Phe Phe Ile Asp
            820                 825                 830
Leu Arg Leu Pro Tyr Ser Val Val Arg Asn Glu Gln Val Glu Ile Arg
            835                 840                 845
Ala Val Leu Tyr Asn Tyr Arg Gln Asn Gln Glu Leu Lys Val Arg Val
            850                 855                 860
Glu Leu Leu His Asn Pro Ala Phe Cys Ser Leu Ala Thr Thr Lys Arg
865                 870                 875                 880
Arg His Gln Gln Thr Val Thr Ile Pro Pro Lys Ser Ser Leu Ser Val
            885                 890                 895
Pro Tyr Val Ile Val Pro Leu Lys Thr Gly Leu Gln Glu Val Glu Val
```

```
                900                 905                 910
Lys Ala Ala Val Tyr His His Phe Ile Ser Asp Gly Val Arg Lys Ser
            915                 920                 925

Leu Lys Val Val Pro Glu Gly Ile Arg Met Asn Lys Thr Val Ala Val
            930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
            995                1000                1005

Gly Cys Gly Glu Gln Asn Met Ile Gly Met Thr Pro Thr Val Ile Ala
           1010                1015                1020

Val His Tyr Leu Asp Glu Thr Glu Gln Trp Glu Lys Phe Gly Leu Glu
1025                1030                1035                1040

Lys Arg Gln Gly Ala Leu Glu Leu Ile Lys Lys Gly Tyr Thr Gln Gln
           1045                1050                1055

Leu Ala Phe Arg Gln Pro Ser Ser Ala Phe Ala Ala Glu Val Lys Arg
           1060                1065                1070

Ala Pro Ser Thr Trp Leu Thr Ala Tyr Val Val Lys Val Phe Ser Leu
           1075                1080                1085

Ala Val Asn Leu Ile Ala Ile Asp Ser Gln Val Leu Cys Gly Ala Val
           1090                1095                1100

Lys Trp Leu Ile Leu Glu Lys Gln Lys Pro Asp Gly Val Phe Gln Glu
1105                1110                1115                1120

Asp Ala Pro Val Ile His Gln Glu Met Ile Gly Gly Leu Arg Asn Asn
           1125                1130                1135

Asn Glu Lys Asp Met Ala Leu Thr Ala Phe Val Leu Ile Ser Leu Gln
           1140                1145                1150

Glu Ala Lys Asp Ile Cys Glu Glu Gln Val Asn Ser Leu Pro Gly Ser
           1155                1160                1165

Ile Thr Lys Ala Gly Asp Phe Leu Glu Ala Asn Tyr Met Asn Leu Gln
           1170                1175                1180

Arg Ser Tyr Thr Val Ala Ile Ala Gly Tyr Ala Leu Ala Gln Met Gly
1185                1190                1195                1200

Arg Leu Lys Gly Pro Leu Leu Asn Lys Phe Leu Thr Thr Ala Lys Asp
           1205                1210                1215

Lys Asn Arg Trp Glu Asp Pro Gly Lys Gln Leu Tyr Asn Val Glu Ala
           1220                1225                1230

Thr Ser Tyr Ala Leu Leu Ala Leu Leu Gln Leu Lys Asp Phe Asp Phe
           1235                1240                1245

Val Pro Pro Val Val Arg Trp Leu Asn Glu Gln Arg Tyr Tyr Gly Gly
           1250                1255                1260

Gly Tyr Gly Ser Thr Gln Ala Thr Phe Met Val Phe Gln Ala Leu Ala
1265                1270                1275                1280

Gln Tyr Gln Lys Asp Ala Pro Asp His Gln Glu Leu Asn Leu Asp Val
           1285                1290                1295

Ser Leu Gln Leu Pro Ser Arg Ser Ser Lys Ile Thr His Arg Ile His
           1300                1305                1310

Trp Glu Ser Ala Ser Leu Leu Arg Ser Glu Glu Thr Lys Glu Asn Glu
           1315                1320                1325
```

-continued

```
Gly Phe Thr Val Thr Ala Glu Gly Lys Gly Gln Gly Thr Leu Ser Val
    1330                1335                1340

Val Thr Met Tyr His Ala Lys Ala Lys Asp Gln Leu Thr Cys Asn Lys
1345                1350                1355                1360

Phe Asp Leu Lys Val Thr Ile Lys Pro Ala Pro Glu Thr Glu Lys Arg
                1365                1370                1375

Pro Gln Asp Ala Lys Asn Thr Met Ile Leu Glu Ile Cys Thr Arg Tyr
            1380                1385                1390

Arg Gly Asp Gln Asp Ala Thr Met Ser Ile Leu Asp Ile Ser Met Met
        1395                1400                1405

Thr Gly Phe Ala Pro Asp Thr Asp Leu Lys Gln Leu Ala Asn Gly
    1410                1415                1420

Val Asp Arg Tyr Ile Ser Lys Tyr Glu Leu Asp Lys Ala Phe Ser Asp
1425                1430                1435                1440

Arg Asn Thr Leu Ile Ile Tyr Leu Asp Lys Val Ser His Ser Glu Asp
                1445                1450                1455

Asp Cys Leu Ala Phe Lys Val His Gln Tyr Phe Asn Val Glu Leu Ile
            1460                1465                1470

Gln Pro Gly Ala Val Lys Val Tyr Ala Tyr Tyr Asn Leu Glu Glu Ser
        1475                1480                1485

Cys Thr Arg Phe Tyr His Pro Glu Lys Glu Asp Gly Lys Leu Asn Lys
    1490                1495                1500

Leu Cys Arg Asp Glu Leu Cys Arg Cys Ala Glu Glu Asn Cys Phe Ile
1505                1510                1515                1520

Gln Lys Ser Asp Asp Lys Val Thr Leu Glu Glu Arg Leu Asp Lys Ala
                1525                1530                1535

Cys Glu Pro Gly Val Asp Tyr Val Tyr Lys Thr Arg Leu Val Lys Val
            1540                1545                1550

Gln Leu Ser Asn Asp Phe Asp Glu Tyr Ile Met Ala Ile Glu Gln Thr
        1555                1560                1565

Ile Lys Ser Gly Ser Asp Glu Val Gln Val Gly Gln Gln Arg Thr Phe
    1570                1575                1580

Ile Ser Pro Ile Lys Cys Arg Glu Ala Leu Lys Leu Glu Glu Lys Lys
1585                1590                1595                1600

His Tyr Leu Met Trp Gly Leu Ser Ser Asp Phe Trp Gly Glu Lys Pro
                1605                1610                1615

Asn Leu Ser Tyr Ile Ile Gly Lys Asp Thr Trp Val Glu His Trp Pro
            1620                1625                1630

Glu Glu Asp Glu Cys Gln Asp Glu Asn Gln Lys Gln Cys Gln Asp
        1635                1640                1645

Leu Gly Ala Phe Thr Glu Ser Met Val Val Phe Gly Cys Pro Asn
    1650                1655                1660

<210> SEQ ID NO 6
<211> LENGTH: 449
<212> TYPE: PRT
<213> ORGANISM: Homo Sapiens

<400> SEQUENCE: 6

Met Met Lys Thr Leu Leu Leu Phe Val Gly Leu Leu Leu Thr Trp Glu
  1               5                  10                  15

Ser Gly Gln Val Leu Gly Asp Gln Thr Val Ser Asp Asn Glu Leu Gln
             20                  25                  30

Glu Met Ser Asn Gln Gly Ser Lys Tyr Val Asn Lys Glu Ile Gln Asn
         35                  40                  45
```

Ala Val Asn Gly Val Lys Gln Ile Lys Thr Leu Ile Glu Lys Thr Asn
            50                  55                  60

Glu Glu Arg Lys Thr Leu Leu Ser Asn Leu Glu Ala Lys Lys Lys
 65                  70                  75                  80

Lys Glu Asp Ala Leu Asn Glu Thr Arg Glu Ser Glu Thr Lys Leu Lys
                    85                  90                  95

Glu Leu Pro Gly Val Cys Asn Glu Thr Met Met Ala Leu Trp Glu Glu
                100                 105                 110

Cys Lys Pro Cys Leu Lys Gln Thr Cys Met Lys Phe Tyr Ala Arg Val
            115                 120                 125

Cys Arg Ser Gly Ser Gly Leu Val Gly Arg Gln Leu Glu Glu Phe Leu
130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
            195                 200                 205

Phe Ser Leu Pro His Arg Arg Pro His Phe Phe Pro Lys Ser Arg
210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
            275                 280                 285

Arg His Asn Ser Thr Gly Cys Leu Arg Met Lys Asp Gln Cys Asp Lys
            290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
                340                 345                 350

Leu Asn Thr Ser Ser Leu Leu Glu Gln Leu Asn Glu Gln Phe Asn Trp
            355                 360                 365

Val Ser Arg Leu Ala Asn Leu Thr Gln Gly Glu Asp Gln Tyr Tyr Leu
370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
                405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
                435                 440                 445

Glu

<210> SEQ ID NO 7
<211> LENGTH: 1744

```
<212> TYPE: PRT
<213> ORGANISM: Homo Sapiens

<400> SEQUENCE: 7

Met Arg Leu Leu Trp Gly Leu Ile Trp Ala Ser Ser Phe Phe Thr Leu
 1               5                  10                  15

Ser Leu Gln Lys Pro Arg Leu Leu Phe Ser Pro Ser Val Val His
             20                  25                  30

Leu Gly Val Pro Leu Ser Val Gly Val Gln Leu Gln Asp Val Pro Arg
             35                  40                  45

Gly Gln Val Val Lys Gly Ser Val Phe Leu Arg Asn Pro Ser Arg Asn
 50                  55                  60

Asn Val Pro Cys Ser Pro Lys Val Asp Phe Thr Leu Ser Ser Glu Arg
65                  70                  75                  80

Asp Phe Ala Leu Leu Ser Leu Gln Val Pro Leu Lys Asp Ala Lys Ser
                 85                  90                  95

Cys Gly Leu His Gln Leu Leu Arg Gly Pro Glu Val Gln Leu Val Ala
            100                 105                 110

His Ser Pro Trp Leu Lys Asp Ser Leu Ser Arg Thr Thr Asn Ile Gln
            115                 120                 125

Gly Ile Asn Leu Leu Phe Ser Ser Arg Arg Gly His Leu Phe Leu Gln
        130                 135                 140

Thr Asp Gln Pro Ile Tyr Asn Pro Gly Gln Arg Val Arg Tyr Arg Val
145                 150                 155                 160

Phe Ala Leu Asp Gln Lys Met Arg Pro Ser Thr Asp Thr Ile Thr Val
                165                 170                 175

Met Val Glu Asn Ser His Gly Leu Arg Val Arg Lys Lys Glu Val Tyr
            180                 185                 190

Met Pro Ser Ser Ile Phe Gln Asp Asp Phe Val Ile Pro Asp Ile Ser
        195                 200                 205

Glu Pro Gly Thr Trp Lys Ile Ser Ala Arg Phe Ser Asp Gly Leu Glu
210                 215                 220

Ser Asn Ser Ser Thr Gln Phe Glu Val Lys Lys Tyr Val Leu Pro Asn
225                 230                 235                 240

Phe Glu Val Lys Ile Thr Pro Gly Lys Pro Tyr Ile Leu Thr Val Pro
                245                 250                 255

Gly His Leu Asp Glu Met Gln Leu Asp Ile Gln Ala Arg Tyr Ile Tyr
            260                 265                 270

Gly Lys Pro Val Gln Gly Val Ala Tyr Val Arg Phe Gly Leu Leu Asp
        275                 280                 285

Glu Asp Gly Lys Lys Thr Phe Phe Arg Gly Leu Glu Ser Gln Thr Lys
290                 295                 300

Leu Val Asn Gly Gln Ser His Ile Ser Leu Ser Lys Ala Glu Phe Gln
305                 310                 315                 320

Asp Ala Leu Glu Lys Leu Asn Met Gly Ile Thr Asp Leu Gln Gly Leu
                325                 330                 335

Arg Leu Tyr Val Ala Ala Ala Ile Ile Glu Ser Pro Gly Gly Glu Met
            340                 345                 350

Glu Glu Ala Glu Leu Thr Ser Trp Tyr Phe Val Ser Ser Pro Phe Ser
        355                 360                 365

Leu Asp Leu Ser Lys Thr Lys Arg His Leu Val Pro Gly Ala Pro Phe
    370                 375                 380

Leu Leu Gln Ala Leu Val Arg Glu Met Ser Gly Ser Pro Ala Ser Gly
385                 390                 395                 400
```

-continued

```
Ile Pro Val Lys Val Ser Ala Thr Val Ser Ser Pro Gly Ser Val Pro
            405                 410                 415
Glu Val Gln Asp Ile Gln Asn Thr Asp Gly Ser Gly Gln Val Ser
        420                 425                 430
Ile Pro Ile Ile Ile Pro Gln Thr Ile Ser Glu Leu Gln Leu Ser Val
            435                 440                 445
Ser Ala Gly Ser Pro His Pro Ala Ile Ala Arg Leu Thr Val Ala Ala
    450                 455                 460
Pro Pro Ser Gly Gly Pro Gly Phe Leu Ser Ile Glu Arg Pro Asp Ser
465                 470                 475                 480
Arg Pro Pro Arg Val Gly Asp Thr Leu Asn Leu Asn Leu Arg Ala Val
                485                 490                 495
Gly Ser Gly Ala Thr Phe Ser His Tyr Tyr Tyr Met Ile Leu Ser Arg
            500                 505                 510
Gly Gln Ile Val Phe Met Asn Arg Glu Pro Lys Arg Thr Leu Thr Ser
        515                 520                 525
Val Ser Val Phe Val Asp His His Leu Ala Pro Ser Phe Tyr Phe Val
    530                 535                 540
Ala Phe Tyr Tyr His Gly Asp His Pro Val Ala Asn Ser Leu Arg Val
545                 550                 555                 560
Asp Val Gln Ala Gly Ala Cys Glu Gly Lys Leu Glu Leu Ser Val Asp
                565                 570                 575
Gly Ala Lys Gln Tyr Arg Asn Gly Glu Ser Val Lys Leu His Leu Glu
            580                 585                 590
Thr Asp Ser Leu Ala Leu Val Ala Leu Gly Ala Leu Asp Thr Ala Leu
        595                 600                 605
Tyr Ala Ala Gly Ser Lys Ser His Lys Pro Leu Asn Met Gly Lys Val
    610                 615                 620
Phe Glu Ala Met Asn Ser Tyr Asp Leu Gly Cys Gly Pro Gly Gly Gly
625                 630                 635                 640
Asp Ser Ala Leu Gln Val Phe Gln Ala Ala Gly Leu Ala Phe Ser Asp
                645                 650                 655
Gly Asp Gln Trp Thr Leu Ser Arg Lys Arg Leu Ser Cys Pro Lys Glu
            660                 665                 670
Lys Thr Thr Arg Lys Lys Arg Asn Val Asn Phe Gln Lys Ala Ile Asn
        675                 680                 685
Glu Lys Leu Gly Gln Tyr Ala Ser Pro Thr Ala Lys Arg Cys Cys Gln
    690                 695                 700
Asp Gly Val Thr Arg Leu Pro Met Met Arg Ser Cys Glu Gln Arg Ala
705                 710                 715                 720
Ala Arg Val Gln Gln Pro Asp Cys Arg Glu Pro Phe Leu Ser Cys Cys
                725                 730                 735
Gln Phe Ala Glu Ser Leu Arg Lys Lys Ser Arg Asp Lys Gly Gln Ala
            740                 745                 750
Gly Leu Gln Arg Ala Leu Glu Ile Leu Gln Glu Asp Leu Ile Asp
        755                 760                 765
Glu Asp Asp Ile Pro Val Arg Ser Phe Phe Pro Glu Asn Trp Leu Trp
    770                 775                 780
Arg Val Glu Thr Val Asp Arg Phe Gln Ile Leu Thr Leu Trp Leu Pro
785                 790                 795                 800
Asp Ser Leu Thr Thr Trp Glu Ile His Gly Leu Ser Leu Ser Lys Thr
                805                 810                 815
Lys Gly Leu Cys Val Ala Thr Pro Val Gln Leu Arg Val Phe Arg Glu
            820                 825                 830
```

```
Phe His Leu His Leu Arg Leu Pro Met Ser Val Arg Arg Phe Glu Gln
            835                 840                 845

Leu Glu Leu Arg Pro Val Leu Tyr Asn Tyr Leu Asp Lys Asn Leu Thr
850                 855                 860

Val Ser Val His Val Ser Pro Val Glu Gly Leu Cys Leu Ala Gly Gly
865                 870                 875                 880

Gly Gly Leu Ala Gln Gln Val Leu Val Pro Ala Gly Ser Ala Arg Pro
                885                 890                 895

Val Ala Phe Ser Val Val Pro Thr Ala Ala Ala Val Ser Leu Lys
            900                 905                 910

Val Val Ala Arg Gly Ser Phe Glu Phe Pro Val Gly Asp Ala Val Ser
            915                 920                 925

Lys Val Leu Gln Ile Glu Lys Glu Gly Ala Ile His Arg Glu Glu Leu
            930                 935                 940

Val Tyr Glu Leu Asn Pro Leu Asp His Arg Gly Arg Thr Leu Glu Ile
945                 950                 955                 960

Pro Gly Asn Ser Asp Pro Asn Met Ile Pro Asp Gly Asp Glu Asn Ser
                965                 970                 975

Tyr Val Arg Val Thr Ala Ser Asp Pro Leu Asp Thr Leu Gly Ser Glu
            980                 985                 990

Gly Ala Leu Ser Pro Gly Gly Val Ala Ser Leu Leu Arg Leu Pro Arg
            995                 1000                1005

Gly Cys Gly Glu Gln Thr Met Ile Tyr Leu Ala Pro Thr Leu Ala Ala
    1010                1015                1020

Ser Arg Tyr Leu Asp Lys Thr Glu Gln Trp Ser Thr Leu Pro Pro Glu
1025                1030                1035                1040

Thr Lys Asp His Ala Val Asp Leu Ile Gln Lys Gly Tyr Met Arg Ile
            1045                1050                1055

Gln Gln Phe Arg Lys Ala Asp Gly Ser Tyr Ala Ala Trp Leu Ser Arg
    1060                1065                1070

Asp Ser Ser Thr Trp Leu Thr Ala Phe Val Leu Lys Val Leu Ser Leu
    1075                1080                1085

Ala Gln Glu Gln Val Gly Gly Ser Pro Glu Lys Leu Gln Glu Thr Ser
    1090                1095                1100

Asn Trp Leu Leu Ser Gln Gln Gln Ala Asp Gly Ser Phe Gln Asp Pro
1105                1110                1115                1120

Cys Pro Val Leu Asp Arg Ser Met Gln Gly Gly Leu Val Gly Asn Asp
                1125                1130                1135

Glu Thr Val Ala Leu Thr Ala Phe Val Thr Ile Ala Leu His His Gly
            1140                1145                1150

Leu Ala Val Phe Gln Asp Glu Gly Ala Glu Pro Leu Lys Gln Arg Val
            1155                1160                1165

Glu Ala Ser Ile Ser Lys Ala Asn Ser Phe Leu Gly Glu Lys Ala Ser
            1170                1175                1180

Ala Gly Leu Leu Gly Ala His Ala Ala Ile Thr Ala Tyr Ala Leu
1185                1190                1195                1200

Ser Leu Thr Lys Ala Pro Val Asp Leu Leu Gly Val Ala His Asn Asn
            1205                1210                1215

Leu Met Ala Met Ala Gln Glu Thr Gly Asp Asn Leu Tyr Trp Gly Ser
            1220                1225                1230

Val Thr Gly Ser Gln Ser Asn Ala Val Ser Pro Thr Pro Ala Pro Arg
            1235                1240                1245

Asn Pro Ser Asp Pro Met Pro Gln Ala Pro Ala Leu Trp Ile Glu Thr
```

-continued

```
            1250                1255                1260

Thr Ala Tyr Ala Leu Leu His Leu Leu His Glu Gly Lys Ala Glu
1265                1270                1275                1280

Met Ala Asp Gln Ala Ser Ala Trp Leu Thr Arg Gln Gly Ser Phe Gln
                1285                1290                1295

Gly Gly Glu Arg Ser Thr Gln Asp Thr Val Ile Ala Leu Asp Ala Leu
            1300                1305                1310

Ser Ala Tyr Trp Ile Ala Ser His Thr Thr Glu Glu Arg Gly Leu Asn
            1315                1320                1325

Val Thr Leu Ser Ser Thr Gly Arg Asn Gly Phe Lys Ser His Ala Leu
            1330                1335                1340

Gln Leu Asn Asn Arg Gln Ile Arg Gly Leu Glu Glu Glu Leu Gln Phe
1345                1350                1355                1360

Ser Leu Gly Ser Lys Ile Asn Val Lys Val Gly Gly Asn Ser Lys Gly
                1365                1370                1375

Thr Leu Lys Val Leu Arg Thr Tyr Asn Val Leu Asp Met Lys Asn Thr
            1380                1385                1390

Thr Cys Gln Asp Leu Gln Ile Glu Val Thr Val Lys Gly His Val Glu
            1395                1400                1405

Tyr Thr Met Glu Ala Asn Glu Asp Tyr Glu Asp Tyr Glu Tyr Asp Glu
            1410                1415                1420

Leu Pro Ala Lys Asp Asp Pro Asp Ala Pro Leu Gln Pro Val Thr Pro
1425                1430                1435                1440

Leu Gln Leu Phe Glu Gly Arg Arg Asn Arg Arg Arg Glu Ala Pro
                1445                1450                1455

Lys Val Val Glu Glu Gln Glu Ser Arg Val His Tyr Thr Val Cys Ile
            1460                1465                1470

Trp Arg Asn Gly Lys Val Gly Leu Ser Gly Met Ala Ile Ala Asp Val
            1475                1480                1485

Thr Leu Leu Ser Gly Phe His Ala Leu Arg Ala Asp Leu Glu Lys Leu
            1490                1495                1500

Thr Ser Leu Ser Asp Arg Tyr Val Ser His Phe Glu Thr Glu Gly Pro
1505                1510                1515                1520

His Val Leu Leu Tyr Phe Asp Ser Val Pro Thr Ser Arg Glu Cys Val
                1525                1530                1535

Gly Phe Glu Ala Val Gln Glu Val Pro Val Gly Leu Val Gln Pro Ala
            1540                1545                1550

Ser Ala Thr Leu Tyr Asp Tyr Tyr Asn Pro Glu Arg Arg Cys Ser Val
            1555                1560                1565

Phe Tyr Gly Ala Pro Ser Lys Ser Arg Leu Leu Ala Thr Leu Cys Ser
            1570                1575                1580

Ala Glu Val Cys Gln Cys Ala Glu Gly Lys Cys Pro Arg Gln Arg Arg
1585                1590                1595                1600

Ala Leu Glu Arg Gly Leu Gln Asp Glu Asp Gly Tyr Arg Met Lys Phe
                1605                1610                1615

Ala Cys Tyr Tyr Pro Arg Val Glu Tyr Gly Phe Gln Val Lys Val Leu
            1620                1625                1630

Arg Glu Asp Ser Arg Ala Ala Phe Arg Leu Phe Glu Thr Lys Ile Thr
            1635                1640                1645

Gln Val Leu His Phe Thr Lys Asp Val Lys Ala Ala Ala Asn Gln Met
            1650                1655                1660

Arg Asn Phe Leu Val Arg Ala Ser Cys Arg Leu Arg Leu Glu Pro Gly
1665                1670                1675                1680
```

-continued

```
Lys Glu Tyr Leu Ile Met Gly Leu Asp Gly Ala Thr Tyr Asp Leu Glu
                1685                1690                1695

Gly His Pro Gln Tyr Leu Leu Asp Ser Asn Ser Trp Ile Glu Met
            1700                1705                1710

Pro Ser Glu Arg Leu Cys Arg Ser Thr Arg Gln Arg Ala Ala Cys Ala
        1715                1720                1725

Gln Leu Asn Asp Phe Leu Gln Glu Tyr Gly Thr Gln Gly Cys Gln Val
        1730                1735                1740

<210> SEQ ID NO 8
<211> LENGTH: 375
<212> TYPE: PRT
<213> ORGANISM: Homo Sapiens

<400> SEQUENCE: 8

Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

Leu Thr Glu Arg Gly Tyr Ser Phe Thr Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320
```

```
Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
                340                 345                 350

Gln Gln Met Trp Ile Ser Lys Gln Glu Tyr Asp Glu Ser Gly Pro Ser
            355                 360                 365

Ile Val His Arg Lys Cys Phe
        370                 375

<210> SEQ ID NO 9
<211> LENGTH: 406
<212> TYPE: PRT
<213> ORGANISM: Homo Sapiens

<400> SEQUENCE: 9

Met Ser Ala Leu Gly Ala Val Ile Ala Leu Leu Leu Trp Gly Gln Leu
  1               5                  10                  15

Phe Ala Val Asp Ser Gly Asn Asp Val Thr Asp Ile Ala Asp Asp Gly
                 20                  25                  30

Cys Pro Lys Pro Pro Glu Ile Ala His Gly Tyr Val Glu His Ser Val
             35                  40                  45

Arg Tyr Gln Cys Lys Asn Tyr Tyr Lys Leu Arg Thr Glu Gly Asp Gly
         50                  55                  60

Val Tyr Thr Leu Asn Asp Lys Lys Gln Trp Ile Asn Lys Ala Val Gly
 65                  70                  75                  80

Asp Lys Leu Pro Glu Cys Glu Ala Asp Asp Gly Cys Pro Lys Pro Pro
                 85                  90                  95

Glu Ile Ala His Gly Tyr Val Glu His Ser Val Arg Tyr Gln Cys Lys
            100                 105                 110

Asn Tyr Tyr Lys Leu Arg Thr Glu Gly Asp Gly Val Tyr Thr Leu Asn
        115                 120                 125

Asn Glu Lys Gln Trp Ile Asn Lys Ala Val Gly Asp Lys Leu Pro Glu
    130                 135                 140

Cys Glu Ala Val Cys Gly Lys Pro Lys Asn Pro Ala Asn Pro Val Gln
145                 150                 155                 160

Arg Ile Leu Gly Gly His Leu Asp Ala Lys Gly Ser Phe Pro Trp Gln
                165                 170                 175

Ala Lys Met Val Ser His His Asn Leu Thr Thr Gly Ala Thr Leu Ile
                180                 185                 190

Asn Glu Gln Trp Leu Leu Thr Thr Ala Lys Asn Leu Phe Leu Asn His
            195                 200                 205

Ser Glu Asn Ala Thr Ala Lys Asp Ile Ala Pro Thr Leu Thr Leu Tyr
        210                 215                 220

Val Gly Lys Lys Gln Leu Val Glu Ile Glu Lys Val Val Leu His Pro
225                 230                 235                 240

Asn Tyr Ser Gln Val Asp Ile Gly Leu Ile Lys Leu Lys Gln Lys Val
                245                 250                 255

Ser Val Asn Glu Arg Val Met Pro Ile Cys Leu Pro Ser Lys Asp Tyr
                260                 265                 270

Ala Glu Val Gly Arg Val Gly Tyr Val Ser Gly Trp Gly Arg Asn Ala
            275                 280                 285

Asn Phe Lys Phe Thr Asp His Leu Lys Tyr Val Met Leu Pro Val Ala
        290                 295                 300

Asp Gln Asp Gln Cys Ile Arg His Tyr Glu Gly Ser Thr Val Pro Glu
305                 310                 315                 320
```

-continued

```
Lys Lys Thr Pro Lys Ser Pro Val Gly Val Gln Pro Ile Leu Asn Glu
            325             330             335

His Thr Phe Cys Ala Gly Met Ser Lys Tyr Gln Glu Asp Thr Cys Tyr
            340             345             350

Gly Asp Ala Gly Ser Ala Phe Ala Val His Asp Leu Glu Glu Asp Thr
            355             360             365

Trp Tyr Ala Thr Gly Ile Leu Ser Phe Asp Lys Ser Cys Ala Val Ala
            370             375             380

Glu Tyr Gly Val Tyr Val Lys Val Thr Ser Ile Gln Asp Trp Val Gln
385             390             395             400

Lys Thr Ile Ala Glu Asn
            405
```